(12) United States Patent
Valliant et al.

(10) Patent No.: US 7,335,347 B2
(45) Date of Patent: Feb. 26, 2008

(54) METHODS FOR PURIFYING RADIOLABELLED COMPOUNDS

(75) Inventors: John F. Valliant, Ancaster (CA); Peter Dorff, Glen Hills, PA (US); Raman Chirakal, Brantford (CA)

(73) Assignee: McMaster University (CA)

( * ) Notice: Subject to any disclaimer, the term of this patent is extended or adjusted under 35 U.S.C. 154(b) by 399 days.

(21) Appl. No.: 10/686,950

(22) Filed: Oct. 16, 2003

(65) Prior Publication Data
US 2004/0260073 A1 Dec. 23, 2004

Related U.S. Application Data

(60) Provisional application No. 60/419,739, filed on Oct. 18, 2002.

(51) Int. Cl.
*A61K 51/00* (2006.01)
*A61M 36/14* (2006.01)

(52) U.S. Cl. .................. 424/1.11; 424/1.65; 424/1.81; 424/1.89

(58) Field of Classification Search ............... 424/1.89, 424/1.11, 1.65, 1.81, 1.85
See application file for complete search history.

(56) References Cited

U.S. PATENT DOCUMENTS

| | | | |
|---|---|---|---|
| 4,025,567 A | 5/1977 | Hutchinson et al. ......... 260/616 |
| 4,401,646 A | 8/1983 | Rhodes ........................... 414/1 |
| 4,599,455 A | 7/1986 | Maruyama et al. .......... 568/411 |
| 4,783,529 A | 11/1988 | Lavallee et al. ............. 540/145 |
| 5,312,935 A | 5/1994 | Mayer et al. ................ 554/182 |
| 5,438,129 A | 8/1995 | Woodard et al. .......... 536/25.4 |
| 5,574,148 A | 11/1996 | Kassis et al. ............ 536/28.52 |
| 5,606,046 A | 2/1997 | Woodard et al. .......... 536/25.4 |
| 5,610,290 A | 3/1997 | Woodard et al. .......... 536/25.4 |
| 5,625,054 A | 4/1997 | Woodard et al. .......... 536/25.4 |
| 5,648,462 A | 7/1997 | Funakoshi et al. .......... 530/344 |
| 5,720,935 A | 2/1998 | Kassis et al. .............. 424/1.73 |
| 5,736,123 A | 4/1998 | Carroll ....................... 424/1.85 |
| 5,777,121 A * | 7/1998 | Curran et al. .................... 546/2 |
| 5,789,534 A | 8/1998 | Koike et al. ................. 528/401 |
| 5,994,588 A | 11/1999 | Funakoshi et al. ............. 568/30 |
| 6,072,020 A | 6/2000 | Arcella et al. ............... 528/176 |
| 6,281,374 B1 | 8/2001 | Schultz ........................ 554/226 |
| 6,409,988 B1 | 6/2002 | Dhonoa et al. ............. 424/1.81 |
| 6,437,159 B1 | 8/2002 | Schultz ........................ 554/188 |
| 6,461,585 B1 * | 10/2002 | Hunter et al. ............... 424/1.85 |
| 6,723,236 B2 | 4/2004 | Fisk et al. ................ 210/198.2 |
| 2002/0087016 A1 | 7/2002 | Schultz ........................ 554/188 |
| 2002/0115893 A1 | 8/2002 | Okamoto et al. ............ 568/842 |
| 2002/0155063 A1 | 10/2002 | Wilson et al. .............. 424/1.11 |
| 2003/0069454 A1 | 4/2003 | Okamoto et al. ............ 568/842 |
| 2003/0120035 A1 | 6/2003 | Gao et al. .................... 530/333 |
| 2003/0178370 A1 | 9/2003 | Fisk et al. .................. 210/656 |
| 2003/0232978 A1 | 12/2003 | Seeberger et al. ......... 536/25.3 |
| 2004/0127755 A1 | 7/2004 | Gladysz et al. | |

OTHER PUBLICATIONS

International Search Report mailed May 28, 2004.

* cited by examiner

*Primary Examiner*—Michael G. Hartley
*Assistant Examiner*—Jagadishwar Samala
(74) *Attorney, Agent, or Firm*—Michel Morency; James F. Ewing; Foley & Lardner LLP

(57) ABSTRACT

One aspect of the present invention relates to a method of purifying radiolabelled compounds comprising a) loading onto a fluorous polymer a radiolabelled compound precursor comprising a fluoroalkyl tin moiety; b) reacting the radiolabelled compound precursor with a radiolabel delivering compound to give a radiolabelled compound, wherein the fluoroalkyl tin moiety is replaced by a radiolabel; and c) eluting the radiolabelled compound from the fluorous polymer.

18 Claims, 40 Drawing Sheets

US 7,335,347 B2

METHODS FOR PURIFYING RADIOLABELLED COMPOUNDS

RELATED APPLICATIONS

This application claims the benefit of priority to U.S. Provisional Patent Application Ser. No. 60/419,739, filed Oct. 18, 2002.

BACKGROUND OF THE INVENTION

The application of radiolabelled peptides, monoclonal antibodies (MoAbs), and oligodeoxynucleotides for diagnostic imaging has heralded a new era for nuclear medicine.[1] Because of their specificity, these compounds allow for functional imaging of specific receptor mediated biochemical processes. Synthetic oligopeptides have been particularly attractive because they can be readily synthesised, and their pharmacokinetic properties are often ideal for nuclear medicine application. For example, an indium-111 labelled somatostatin analogue consisting of 8 amino acids is now used routinely to localise and image neuroendocrine tumours.[2]

SUMMARY OF THE INVENTION

In one embodiment, the present invention is drawn to a method of purifying radiolabelled compounds comprising: a) loading onto a fluorous polymer a radiolabelled compound precursor comprising a fluoroalkyl tin moiety; b) reacting the radiolabelled compound precursor with a radiolabel delivering compound to give a radiolabelled compound, wherein the fluoroalkyl tin moiety is replaced by a radiolabel; and c) eluting the radiolabelled compound from the fluorous polymer.

In a further embodiment, the radiolabelled compound comprises an aryl moiety.

In a further embodiment, the radiolabelled compound comprises an aryl acid.

In a further embodiment, the radiolabelled compound is a benzoic acid.

In a further embodiment, the radiolabelled compound is a benzamide.

In a further embodiment, the benzamide is an N-(2-diethylaminoethyl)benzamide.

In a further embodiment, the radiolabelled compound is a benzylamine.

In a further embodiment, the radiolabelled compound is a benzylguanidine.

In a further embodiment, the radiolabelled compound is a benzylamine-GFLM(f).

In a further embodiment, the fluoroalkyl tin moiety is tris(perfluorohexylethyl)tin.

In a further embodiment, the fluorous polymer is a fluorous silica.

In a further embodiment, the radiolabel is selected from the group consisting of $^{99m}$Tc, $^{94m}$Tc, $^{186}$Re, $^{105}$Rh, $^{18}$F, $^{11}$C, $^{125}$I, $^{123}$I, $^{131}$I, $^{76}$Br, and $^{111}$At.

In a further embodiment, the radiolabel is selected from the group consisting of $^{18}$F, $^{125}$I, $^{123}$I, and $^{131}$I.

In a further embodiment, the radiolabelled compound is a benzoic acid, the fluoroalkyl tin moiety is tris(perfluorohexylethyl)tin, the fluorous polymer is fluorous silica, and the radiolabel is $^{18}$F.

In a further embodiment, the radiolabelled compound is a benzoic acid, the fluoroalkyl tin moiety is tris(perfluorohexylethyl)tin, the fluorous polymer is fluorous silica, and the radiolabel is $^{125}$I.

In a further embodiment, the radiolabelled compound is an N-(2-diethylaminoethyl)benzamide, the fluoroalkyl tin moiety is a tris(perfluorohexylethyl)tin, the fluorous polymer is fluorous silica, and the radiolabel is $^{123}$I.

In a further embodiment, the radiolabelled compound is benzylamine, the fluoroalkyl tin moiety is tris(perfluorohexylethyl)tin, the fluorous polymer is fluorous silica, and the radiolabel is selected from the group consisting of $^{123}$I and $^{131}$I.

In a further embodiment, the radiolabelled compound is a benzylguanidine, the fluoroalkyl tin moiety is tris(perfluorohexylethyl)tin, the fluorous polymer is fluorous silica, and the radiolabel is selected from the group consisting of $^{123}$I and $^{131}$I.

In a further embodiment, the radiolabelled compound is a benzylamine-GFLM(f), the fluoroalkyl tin moiety is tris(perfluorohexylethyl)tin, the fluorous polymer is fluorous silica, and the radiolabel is selected from the group consisting of $^{123}$I and $^{131}$I.

DETAILED DESCRIPTION OF THE INVENTION

Figure 1:
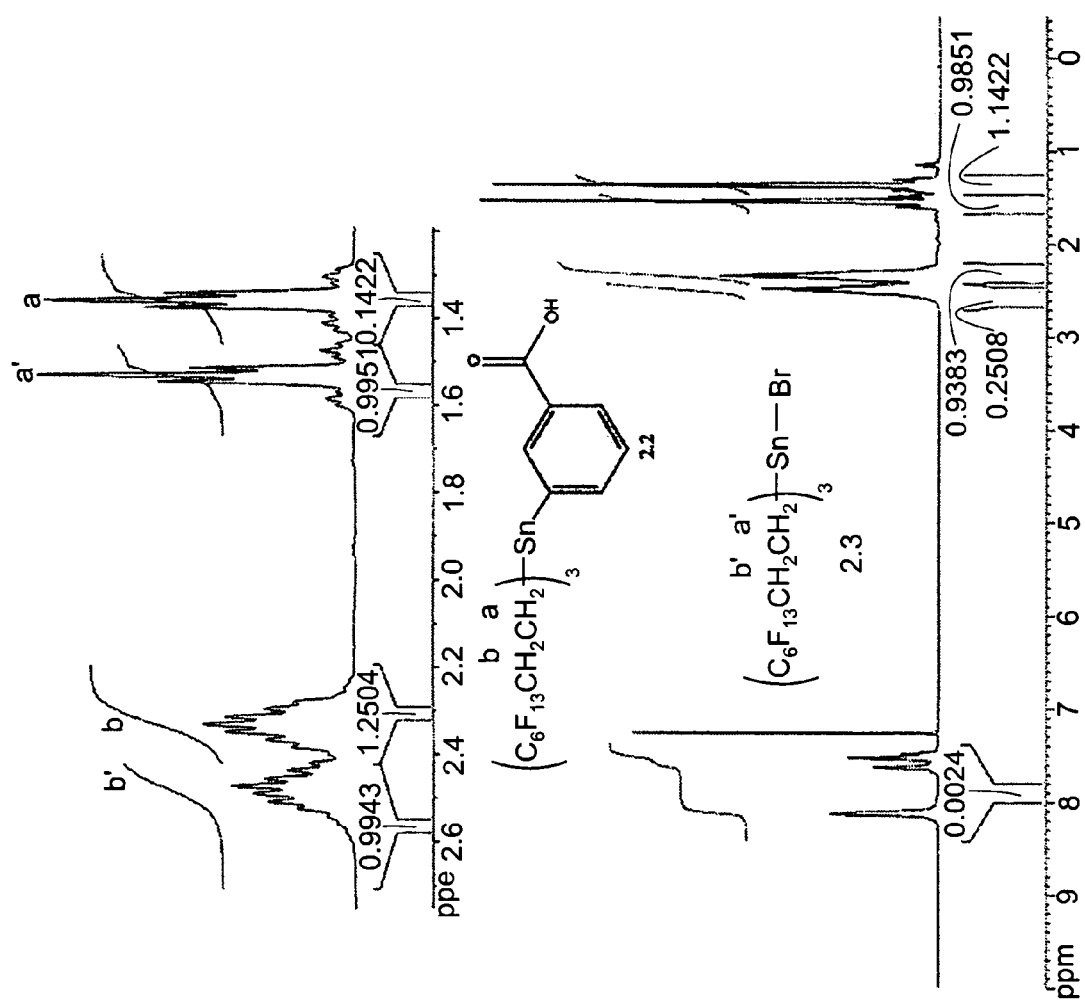
FIG. 1 depicts an $^1$H-NMR [CDCl$_3$, 500 MHz] spectrum of derivatization of 2.2

Labelling Benzoic Acid and Benzamide Using Fluorous Chemistry

There are two main approaches for incorporating radiohalogens into peptides. The first approach is direct labelling of the parent molecule. Tyrosine residues, for example, can be labelled through electrophilic iodination[3], iodogen[4], or with the Bolton-Hunter reagent.[5] The main disadvantage of these strategies is that the regioselectivity and stoichiometry of the labelling reaction is often hard to control.

The second approach involves reaction of a labelled precursor bearing an activated ester functionality, which will react with pendent amino groups on the peptide. When attention is paid to reaction conditions, the resulting amide bonds can be formed regioselectively. Two of the most common labelling agents are, N-succinimidyl 4-[$^{18}$F]fluorobenzoate ([$^{18}$F]SFB) and N-succinimidyl 3-[$^{131}$I]iodobenzoate (SIB).[6,7] The $^{18}$F- and $^{125}$I-derivatives are typically synthesised by nucleophilic substitution and destannylation reactions, respectively (Scheme 1).

Scheme 1.
Synthesis and conjugation of [$^{18}$F]SFB and [$^{125}$I]SIB

N-succinimidyl 4-[$^{18}$F]fluorobenzoate

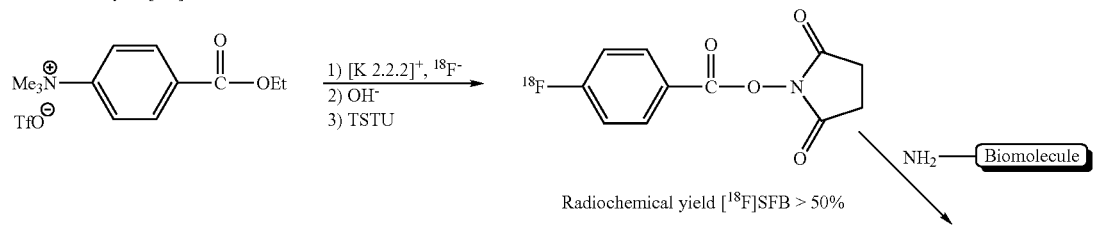

Radiochemical yield [$^{18}$F]SFB > 50%

N-succinimidyl-3-[$^{125}$I]iodobenzoate

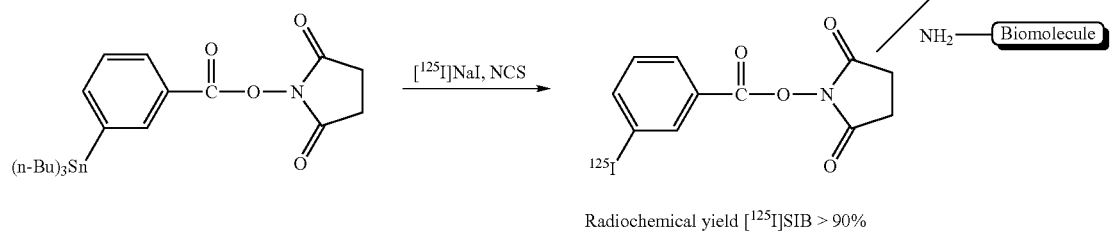

Radiochemical yield [$^{125}$I]SIB > 90%

In order to best illustrate the utility of the fluorous synthesis approach for radiopharmaceutical development, a model compound, which was both useful and amenable to different labelling approaches, was chosen. In this way, the target compound became tris(perfluorohexylethyl)tin-3 or 4-benzoic acid (Compound 2.1 or 2.2).

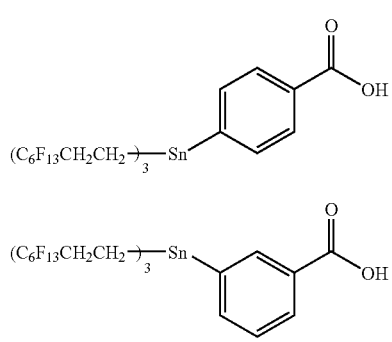

It was hoped that 2.1 and/or 2.2 would facilitate labelling with a variety of isotopes including ([$^{18}$F]F$_2$ and [$^{125}$I]I$_2$), and permit conjugation to a variety of amino terminated compounds and biomolecules both prior to and after labelling.

The "fluorous tag"

The "fluorous tag" used throughout this research was bromo[tris(2-perfluorohexylethyl)tin] (2.3), which was prepared following the method of Curran et al.[8] Compound 2.3 was synthesised via the arylstannyl, 2.4, which in turn was prepared using a Grignard reaction of phenyltintrichloride and 2-perfluorohexyl-1-iodoethane (Scheme 2). Removal of the homocoupled impurity by vacuum distillation and subsequent column chromatography yielded 2.4 in 75% yield. The $^1$H NMR of 2.4 in CDCl$_3$ showed a singlet at 7.33 ppm (5H, aromatic) along with the triplet at 1.23 ppm (with Sn satellites $^2J_{Sn,H}$=51.7 Hz) and multiplet at 2.24 ppm corresponding to the methylene protons α and β to the tin. The $^{13}$C NMR shows three aromatic signals at 129.06 ppm, 129.65 ppm, 136.08 ppm. The $^{13}$C NMR resonances at −1.49 ppm and triplet at 27.74 ppm ($^3J_{F,C}$=23.5 Hz) correspond to the carbons α and β to tin respectively. The negative ion electrospray mass spectrum of compound 2.4 gave peaks at m/z=1297 [M+OAc-H]$^-$ and m/z=1283.0 [M+OAc-CH$_3$]$^-$. In addition, the IR spectrum reveals strong absorbances corresponding to the aromatic ring at 2962, 2928, 2874, and 2862 cm. These findings are consistent with literature values.[8]

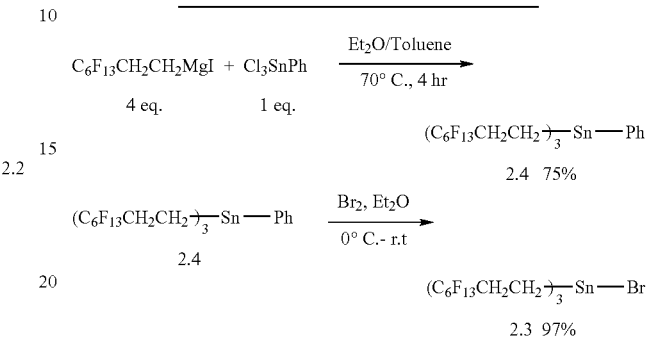

Compound 2.4 was subsequently reacted with excess bromine and 2.3 was purified through vacuum distillation, yielding the desired product in 97% yield. Conversion of 2.4 to 2.3 was confirmed through disappearance of aromatic resonances in $^1$H and $^{13}$C NMR spectra. In addition, substitution of the electronegative bromine shifts $^1$H and $^{13}$C signals for the nuclei α to the tin to lower field. The effect is quite dramatic; the $^1$H$_\alpha$ chemical shift increases from 1.23 ppm to 1.57 ppm with Sn satellites ($^2J_{Sn,H}$=54.1 Hz), while the $^{13}$C$_\alpha$ signal shifts from −1.49 ppm to 6.11 ppm. The $^{13}$C resonances for the fluorine bearing carbon atoms appear as highly coupled multiplets from 108.86 ppm to 121.71 ppm. The negative ion electrospray mass spectrum for 2.3 gave a single peak at m/z=1279.5 [M+OAc]$^-$. These results are also consistent with literature findings.[8]

Synthesis of tris(perfluorohexylethyl)tin-3 or 4-benzoic acid (2.1, 2.2)

Four strategies for the synthesis of 2.1 were undertaken (Scheme 3). Each involves nucleophilic attack of an organometallic reagent onto the tin-bromide compound (2.3).

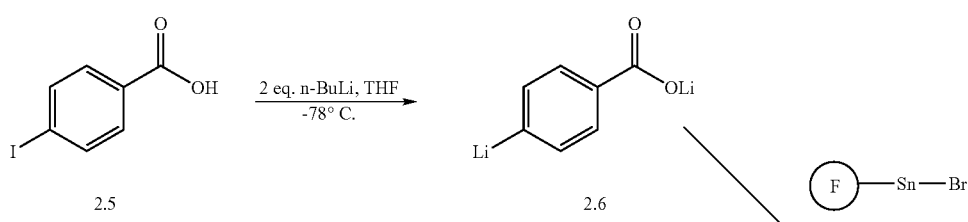

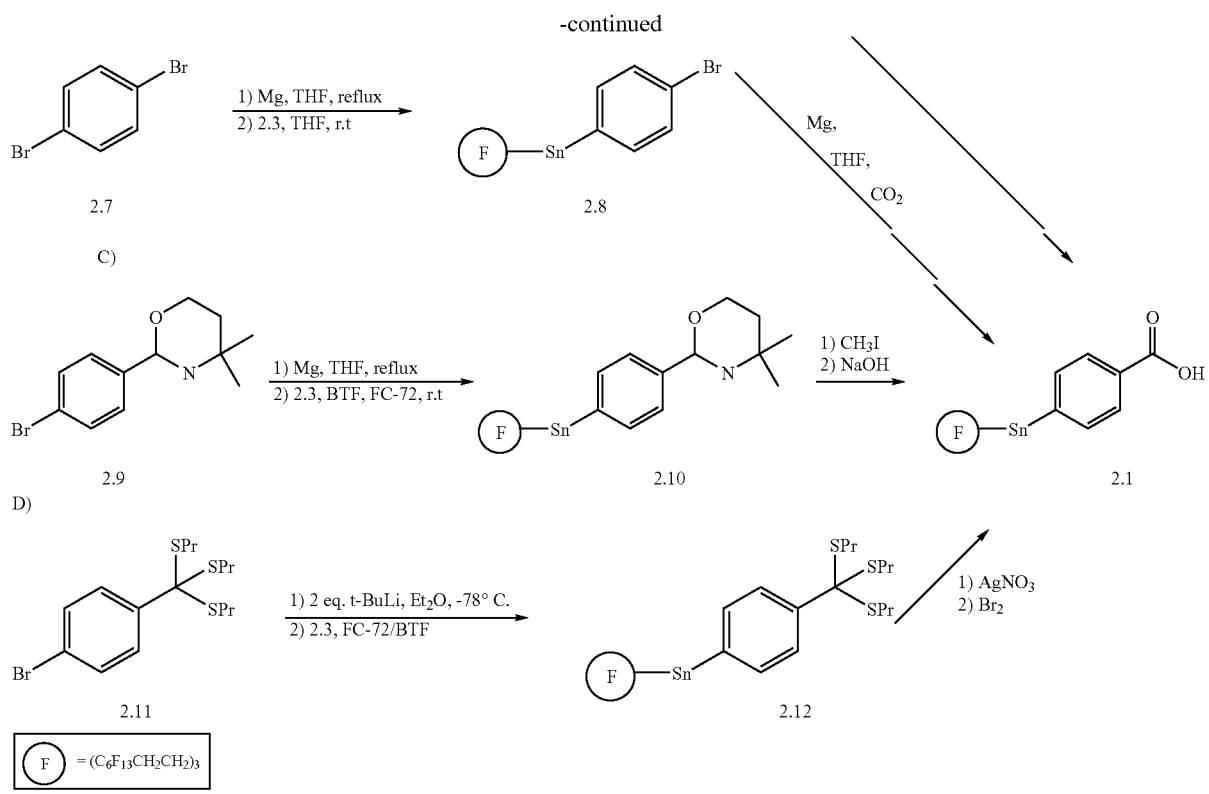

In the first approach, A, the procedure of Zalutsky et al.[4], which was used to prepare N-succinimidyl-3-(tri-n-butyl-stannyl)benzoate, was employed. Reaction of 2.3 with excess of the dilithiated species (2.6) successfully generated 2.1. Purification of the fluorous material was facilitated through a triphasic extraction into FC-72® from dichloromethane and water. Unfortunately, the extent of benzoic acid incorporation into the final product was consistently <35% of total available sites. The extent of product (arylstannane) formation vs. unreacted starting material (bromostannane) was determined using $^1$H NMR. Integration of $^1H_{\alpha,\beta}$ signals for the two different chemical environments, with respect to one another and to the aromatic protons provides a reasonable assessment of the extent of incorporation (FIG. 1). Purification was attempted though column chromatography in accordance with the methods described by Curran et al.[9] Due to the similarity in $R_f$ values between 2.1 and 2.3, no level of separation could be attained.

Approach B involved modifying the procedure described by Lequan et al. for the synthesis of p-(phenylmethylisopropylstannyl)benzoic acid.[10] The mono-anion of p-dibromobenzene was reacted with 2.3, yielding 2.8 quantitatively. Unfortunately, repeated attempts to lithiate 2.8 were unsuccessful, preventing the successive reaction with $CO_2$.

Approach C was based on the method reported by Milius et al. for the synthesis of 4-tri-n-butylstannyl-benzoic acid oxazoline.[11] The appeal of the oxazoline protecting group was its stability to Grignard reaction conditions, and, more importantly, its ability to be deprotected under mild, non acidic conditions. The precursor, compound 2.9, was synthesised by treatment of p-bromobenzoic acid with thionyl chloride to give the acid chloride. The acid chloride was subsequently reacted with 2-amino-2-methyl-propanol to afford the amide. Treatment of the amide with thionyl chloride in the absence of solvent induced cyclization to the oxazoline ring, generating 2.9 in 95% yield.

$^1$H NMR of compound 2.9 showed a singlet at 1.42 ppm (6H), singlet at 4.17 ppm (2H) and doublets at 7.56 (2H) and 7.87 ppm (2H). The $^{13}$C NMR and the electron impact mass spectrum (m/z=254) for 2.9 also agree well with the literature.[12]

Formation of the Grignard was sluggish, and necessitated the addition of 1,2-dibromoethane in order to promote the reaction. Eventually, 2.3 was quantitatively converted to 2.10, which was purified through a triphasic extraction and isolated in a 90% yield.

The $^1$H NMR of 2.10 showed the typical shift in $H_{\alpha,\beta}$ to higher field. The $^1$H NMR also revealed peaks at 1.40 ppm and 4.14 ppm from the oxazoline group, and aromatic signals at 7.44 ppm and 7.97 ppm. Similarly, the $^{13}$C NMR showed the $C_\alpha$ signal shift to a higher field of −1.25 ppm, in addition to the appearance of methyl carbons at 28.5 ppm and aromatic resonances at 128.4 ppm and 136.0 ppm. The negative ion electrospray mass spectrum gave a peak at m/z=1394 [M+OAc]$^−$.

In order to facilitate cleavage of the oxazoline group under basic conditions, it was necessary to convert the oxazoline to the oxazolinium ion. In all instances, reaction with methyliodide under mild reaction conditions yielded none of the desired quaternerized product. Alternatively, under the vigorous reaction conditions suggested by literature, cleavage of the aryl-stannyl bond occurred.[13]

Approach D required the initial synthesis of a thiol protected intermediate, tripropyl 4-bromoorthothiobenzoate 2.11. The reaction pathway for D (Scheme 4) was applied originally to the synthesis of the analogous silicon fluorous compound.[9] The synthesis of the precursor 2.11 involved reaction of p-bromobenzoic acid with thionyl chloride to generate the acid chloride, which was then reacted with excess propane thiol in the presence of AlCl$_3$. Despite the fact that a great deal of attention was paid to ensuring reagent quality (AlCl$_3$ was freshly sublimed and propane thiol was freshly distilled), the crude reaction product consisted of only one or two condensed propane thiol groups. The orthothiobenzoate was never observed as it was described in the paper by Studer et al.[9]

The successful methodology, approach E (Scheme 4), entailed adaptation of research by Xizhen, Z et al., who established the feasibility of synthesising arylstannanes using organozinc reagents.[14] The use of the robust organozinc reagents, rather than organolithium reagents, facilitates the incorporation of compounds with electrophilic functionalities, such as esters, nitriles, and ketones.

Excess 3-ethoxycarbonylphenylzinc (2.13), which is commercially available through Rieke Metals Inc., was reacted with 2.3 overnight (Scheme 4). The product was isolated through a biphasic extraction between FC-72® and methanol in excellent yield (99%).

Scheme 4. Synthesis of tris(perfluorohexylethyl)tin-3-benzoic acid (2.2)

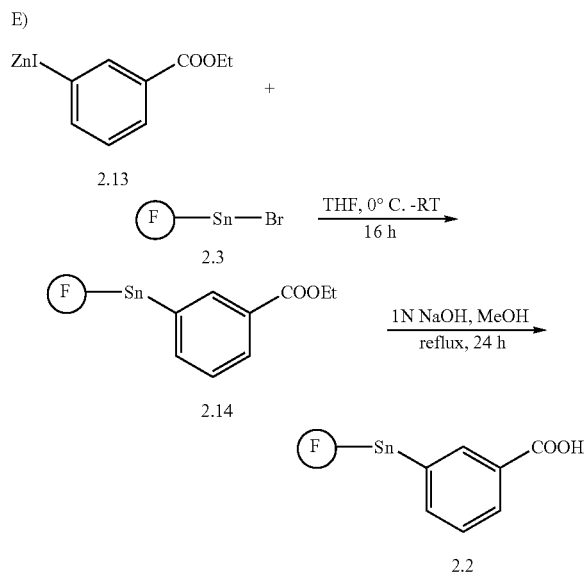

Analysis of $^1$H NMR for compound 2.14 revealed signals corresponding to the ethylene spacer at 1.35 ppm (t, 6H), and 2.33 ppm (m, 6H), in addition to peaks at 1.39 ppm (m, 3H), 4.39 ppm (q, 2H), and a meta-disubstituted aromatic from 7.47-8.07 ppm (m, 4H). The $^{13}$C NMR for 2.14 showed four signals at high field −1.12 ppm, 14.15 ppm, 27.87 ppm ($^2J_{F,C}$=23.3 Hz), and 61.32 ppm. At low field the $^{13}$C NMR had resonances corresponding to carbon atoms with attached fluorines (106.46 ppm to 121.17 ppm) and aromatic resonances, which have yet to be assigned due to difficulty interpreting the spectrum. The negative ion mass spectrum of 2.14 gave peaks at m/z=1279.4 [M-Ethyl] and m/z=1369.5 [M+OAc]$^-$.

Saponification of 2.14 was achieved using excess base, despite the fact that the substrate was immiscible in the reaction solvent (methanol/water 4:1). Small amounts of the transesterification product were occasionally observed; however, this product was removed by way of a second hydrolysis reaction. Isolation of the product from FC-72® following several washings with water yields 2.2, presumably as the sodium salt, in 99% yield. Extraction of the sodium salt of 2.2 between FC-72®, dichloromethane, and a 1N HCl solution, produced the free acid.

The difference in solubility of the salt vs. the acid in CDCl$_3$ was pronounced. The acid dissolves in chloroform-d$_3$ to provide well resolved $^1$H and $^{13}$C NMR spectra, while the sodium salt was only sparingly soluble. The free carboxylic acid, 2.2, unlike the sodium salt, crystallised over several days yielding a white solid.

Figure 2:
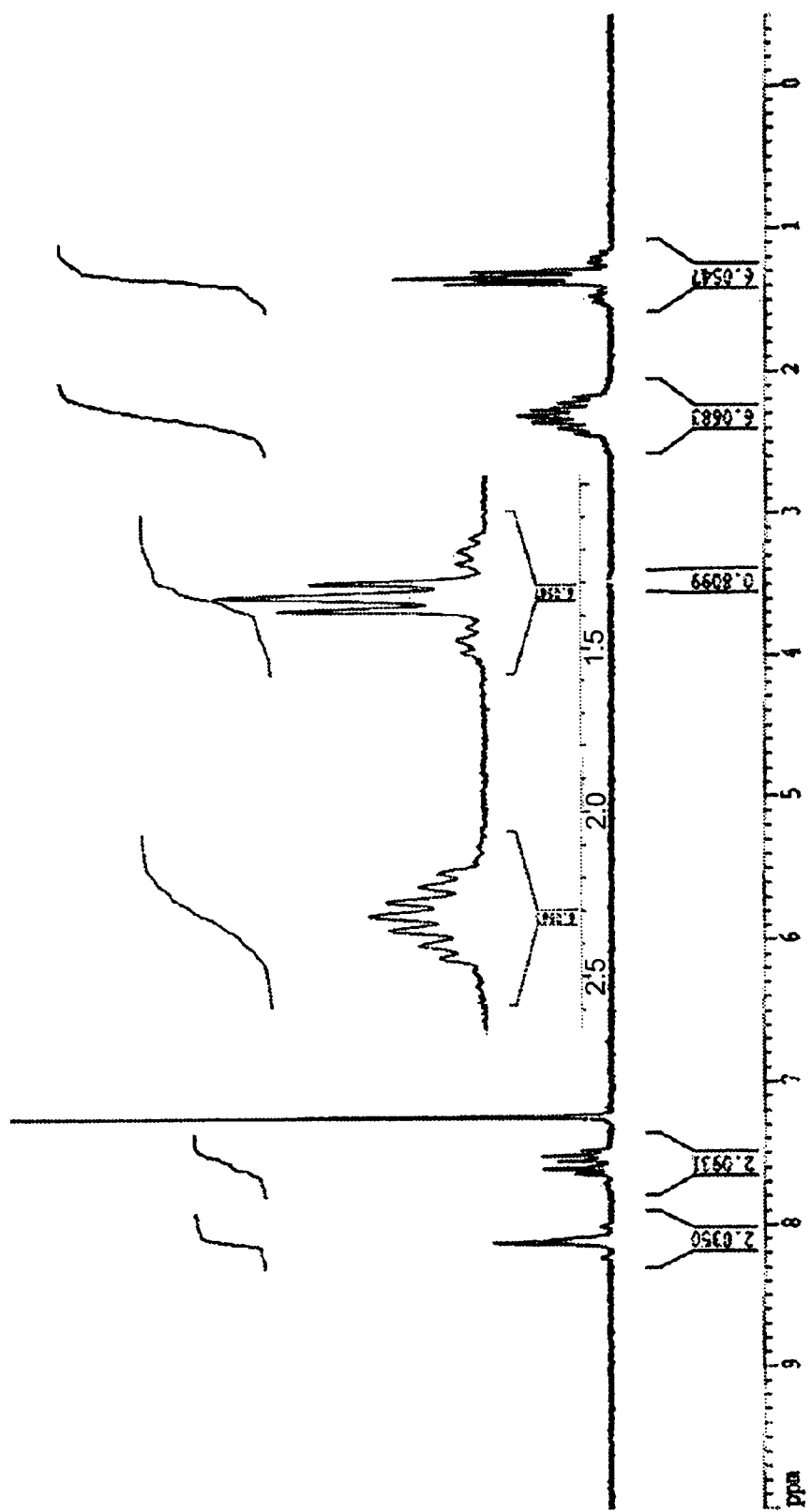
FIG. 2 depicts an $^1$H-NMR [CDCl$_3$, 200 MHz] spectrum of compound 2.2.
Figure 3:
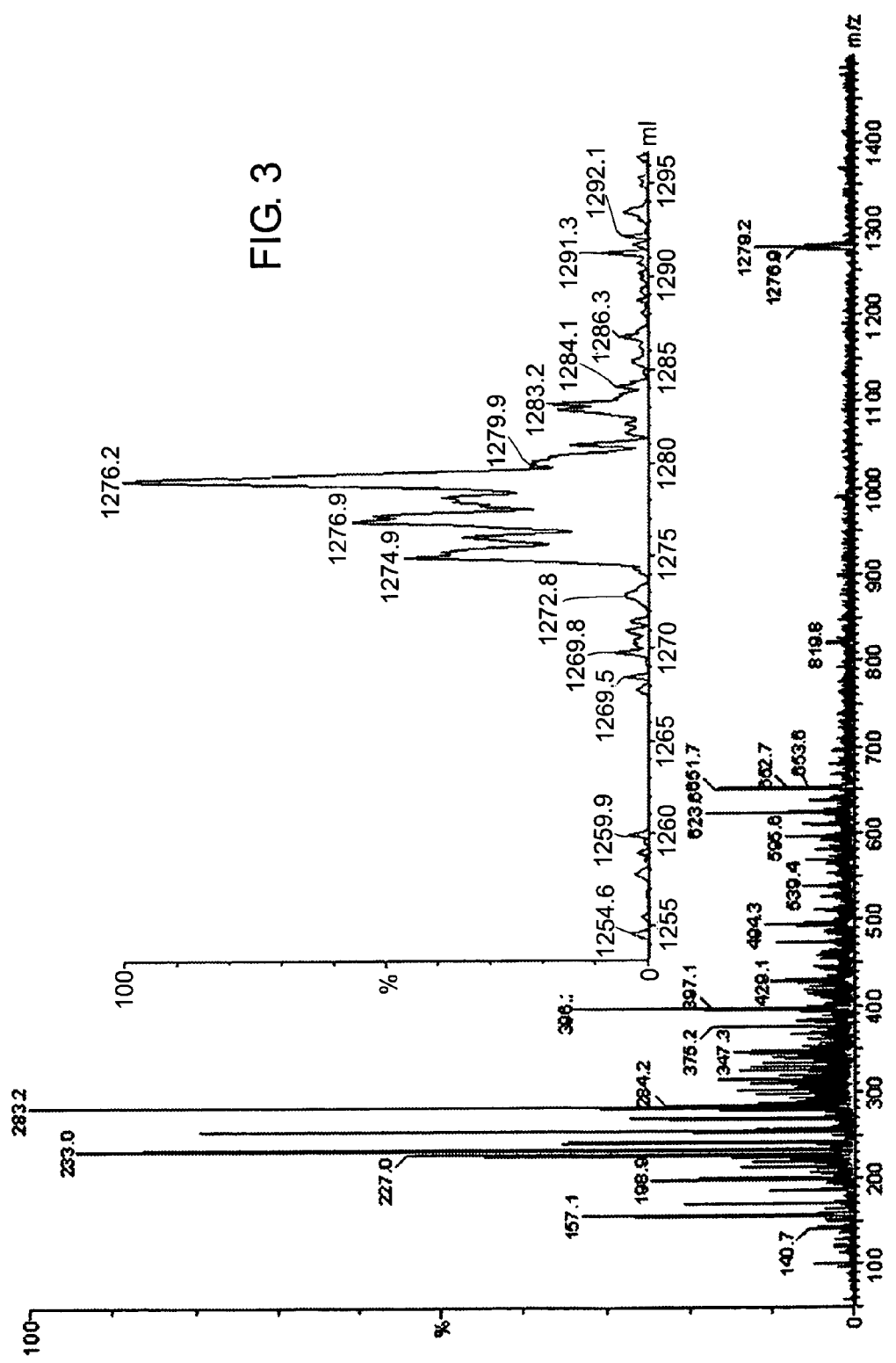
FIG. 3 depicts a negative ion electrospray mass spectrum of compound 2.2.

The $^1$H NMR of compound 2.2 (FIG. 2) showed an absence of the signals corresponding to the ester group, but was otherwise unchanged from 2.14. Similarly, the $^{13}$C NMR lacked the peaks associated with the ester group and had a corresponded shift of the carbonyl carbon to lower field (172.61 ppm and 172.04 ppm). The $^{13}$C peaks all have a small shoulder peak similar to the carbonyl carbon, which is perhaps a reflection of the presence of a small amount of sodium salt of compound 2.2. The negative ion electrospray mass spectrum of compound 2.2 (FIG. 3) shows a peak at m/z=1279 [M-H]$^-$. The IR spectrum of 2.2 importantly showed a strong O—H stretch at 3410 cm$^{-1}$, C=O stretch at 1632 cm$^{-1}$, and an aromatic stretch at 2950 cm$^{-1}$.

Figure 4:
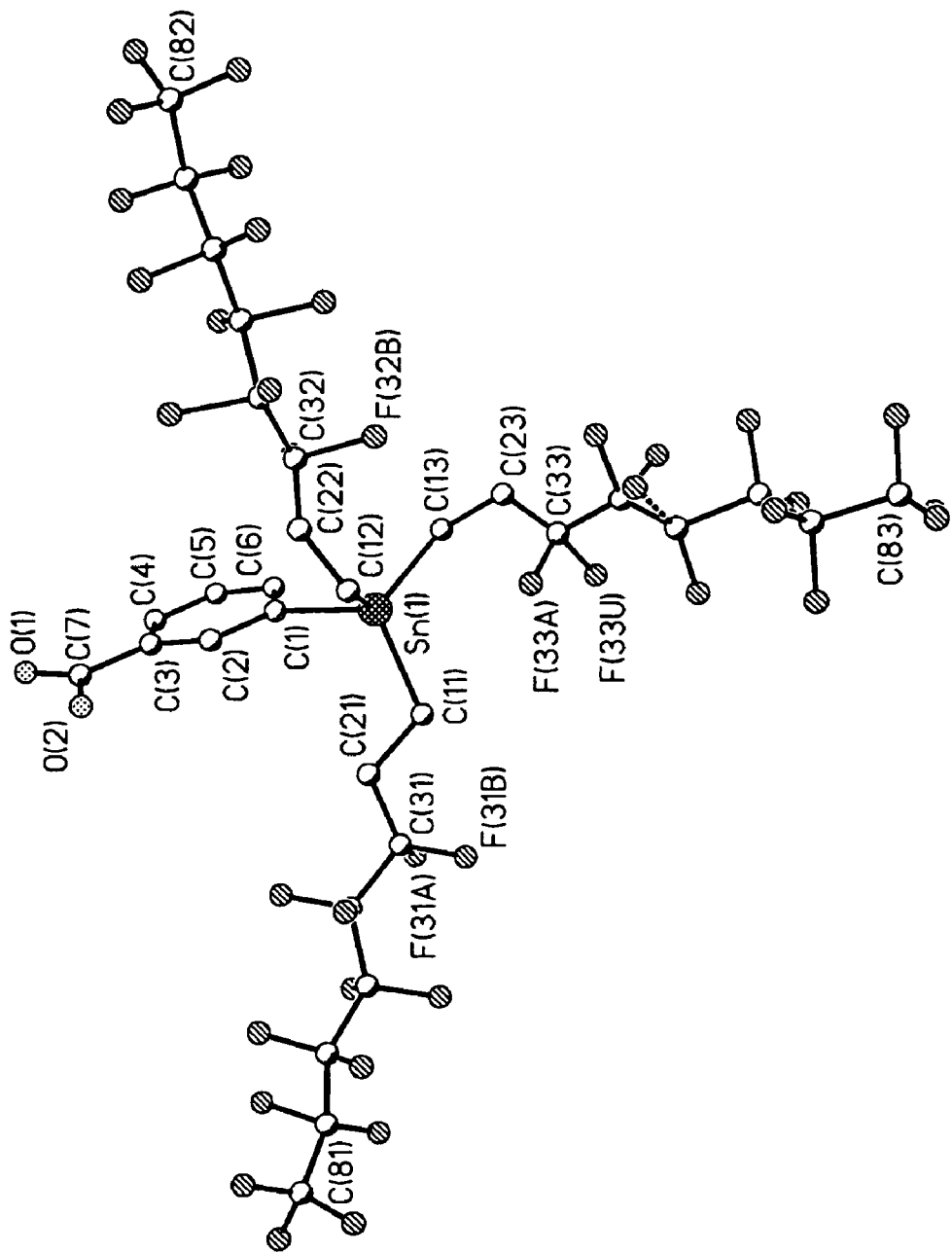
FIG. 4 depicts the X-ray crystal structure of compound 2.2.

Dissolving a small quantity of 2.2 in pentane, followed by its slow evaporation, produced long needle-like crystals from which an X-ray crystal structure was obtained. This is significant, as it represents the first reported crystal structure of a perfluorostannane species of any variety. Compound 2.2 crystallised in the triclinic ρ-1 space group with two independent molecules in the unit cell (Z=4). The structure proved difficult to solve, in large part due to the high level of disorder in one particular perfluorooctyl chain. This is reasonable considering the low barrier of rotation around the C—C bond, which typically leads to the oily property of these compounds. Though additional work is still required prior to publishing the X-ray crystal structure, the current structure verifies the presence of compound 2.2 (FIG. 4).

Synthesis of 3-fluorobenzoic Acid (2.15).

Figure 5:
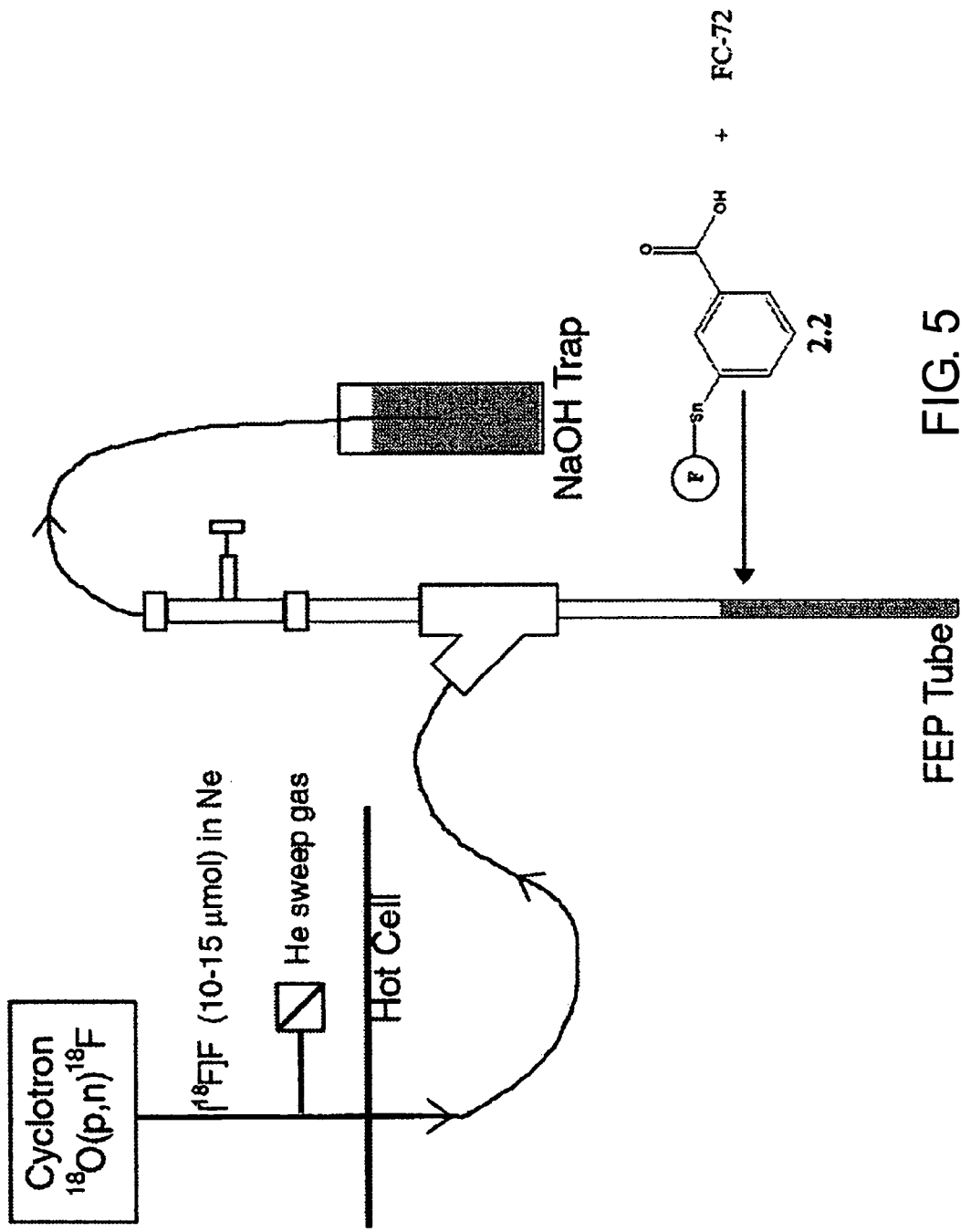
FIG. 5 depicts the fluorination apparatus used in both F$_2$ and [$^{18}$F]F$_2$ reactions.

Fluorination of tris(perfluorohexylethyl)tin-3-benzoic acid (2.2) was initially performed in perfluorinated hexanes (FC-72®), rather than the more commonly employed HF, or freons such as CFCl$_3$. The use of FC-72® is advantageous, since it readily dissolves the precursor, has a suitable freezing and boiling point range (−100° C. and 65° C. respectively) and is not susceptible to degradation by F$_2$. The reaction conditions were worked out and optimised through a number of fluorination reactions, where conditions mimic those of the [$^{18}$F]F$_2$ reaction without having to deal with the risks of radiation-exposure. Scheme 5 and FIG. 5 illustrates the reaction and apparatus used in a general fluorination reaction, respectively.

Scheme 5.
Synthesis of 2.15 from fluorous substrate 2.2.

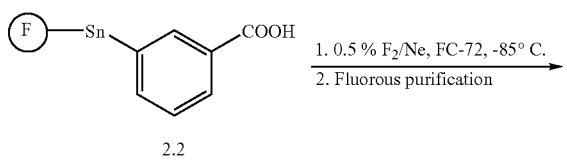

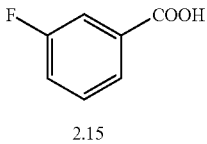

2.15

In general, the substrate 2.2 was diluted in FC-72® (1 mL) and transferred to a dried fluoropolymer vessel. The contents of the vessel were cooled to approximately −85° C. in a MeOH/N$_2$ slush bath, after which 180 psi of a 0.5% F$_2$ in Ne solution were bubbled through the solution over a 20-30 minute period. The solvent was transferred to a vial along with methanol, which was used to rinse the reaction vessel. The entire mixture was evaporated by rotary evaporation, dissolved in acetonitrile:water (1:1) and passed down a fluorous column. Fractions (3×3 mL) were collected and characterised using $^{19}$F NMR, HPLC and MS spectroscopy.

The $^{19}$F NMR of the reaction product 2.15 showed roughly a quartet at −112.00 ppm ($^3J_{F,H}$=5.76 Hz) when run in MeOH:CHCl$_3$, consistent with an authentic m-fluorobenzoic acid standard and literature values.[15,16] The negative ion electrospray mass spectrum of compound 2.15 gave the requisite peak at m/z=139.1 [M−H]$^−$. HPLC of the purified reaction mixture produced a single peak at 4.22 min, consistent with the authentic standard.

The immiscibility of perfluorocarbons with most organic solvents has led to the development of a new approach to synthesis known as the fluorous biphasic system (FBS). In this approach, molecules containing appreciable fluorine content (fluorous compounds) can be selectively separated from non-fluorinated compounds. Common separation techniques include biphasic extraction, triphasic extraction or application of fluorous reversed phase silica gel. The latter technique takes advantage of the tendency of fluorous substrates to interact strongly with the fluorous solid phase thereby dramatically increasing their retention time compared to non-fluorous materials.

The fluorous biphasic approach can be used as a means of preparing radiolabeled substrates in high apparent specific activity. The technique entails binding a substrate to a fluorous-support in such a manner that the fluorous component is released upon reaction with the radionuclide of choice. The target radiochemical can then be readily separated from the fluorous support (and any fluorous byproducts) by passing the material through a plug of fluorous silica, or other suitable solid material, or by liquid-liquid extraction. This approach can yield iodine and fluorine labelled compounds in high chemical and radiochemical yields in a time and resource efficient manner. In particular, the fluorous approach can be used to prepare iodo and fluoro-labelled benzoic acids, which are important substrates for labelling proteins.

Initially in this research, fluorous silica synthesised in our laboratory was used in the purification process. It proved, however, to be less effective at retaining fluorous material than commercially available fluorous modified silica manufactured by Silicycle®. The improved retention of the commercial variety, which was attributed to improved loadings, facilitated a more rapid purification. In the case of the "home-made" and commercial fluorous silica we also observed that the use of alcoholic solvents as a mobile phase resulted in substantial breakthough of the fluorous impurities. In order to remedy this, an acetonitrile:water (1:1) eluent system was used, and appears to have prevented any migration of the perfluorotin impurity. Elution of the product 2.15, however occurs rapidly and is obtained (>99%) within the first 9 mL of eluent.

In the initial reaction mixtures, two extraneous peaks were consistently found in the $^{19}$F NMR spectrum (−74 ppm and −153 ppm), in addition to the product peak at −112 ppm. Initially, it was believed that these additional peaks were the result of FC-72®, which is composed of multiple isomers of perfluorinated hexanes. However, subjecting FC-72® to the same fluorination and purification conditions yielded no observable peaks in the fluorine spectrum.

It was later found that the peak at −74 ppm was not present when medical grade sterile water replaced the laboratories own distilled-deionized water. Further, the peak at −153 ppm was found to originate from the use of Silicycles brand fluorous silica. Replacement of this brand of silica with that prepared by Fluorous technologies® proved to remove this peak from the fluorine spectrum.

The reaction temperature also proved to influence the products generated in these reactions. When the reactions were carried out at higher temperatures, >−65° C., it was found that an occasionally small peak at −105 ppm (unresolved coupling) could be seen in the spectrum. This could be the result of ortho substitution or a di-fluorinated ring, both of which would result in deshielding of the attached fluorine. This small impurity, however, was not seen when the reaction was carried out at lower temperature (−85° C. to −75° C.).

In the course of these cold fluorinations, the yield of m-fluorobenzoic acid was optimised. The ratio of substrate to F$_2$ was varied between 0.7 to 3.0 in all cases, using 180 psi (0.5% F$_2$) which corresponds to 1.18×10$^{-4}$ mol of F$_2$, similar to the amount used in a $^{18}$F[F$_2$] reaction. The percent yield of 2.15 with respect to F$_2$ decreased from 18% to 16% when 0.65 and 2.9 equivalents were used respectively. The yield analysis was based on comparison with calibration curves. It was found that the yield of 2.15 with respect to F$_2$ reached a maximum at approximately 24% when the ratio of substrate to F$_2$ was 1.2:1. Since the reactions were run in equivalent volumes of FC-72®, the decreasing yield may be a result of a visibly increasing viscosity in the more concentrated samples.

Synthesis of 3-[$^{18}$F]fluorobenzoic acid (2.16).

The successful cold labelling and purification of 2.15 using the precursor 2.2 prompted the investigation of [18F] F$_2$ labelling. The reaction scheme is shown in Scheme 6.

Scheme 6.
Synthesis of 3-[$^{18}$F]fluorobenzoic acid 2.16.

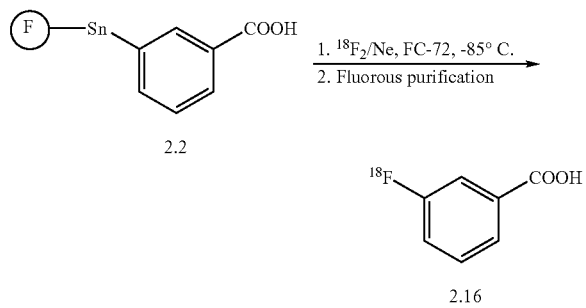

Fluorine-18 was produced at McMaster University Hospital by the $^{18}$O(p,n)$^{18}$F nuclear reaction using a Siemens RDS 112 proton cyclotron operating at 11 MeV by the "double shoot" method.[17] The "double shoot" method entails diluting $^{18}F$, which remains largely bound to the target wall following the $^{18}O(p,n)^{18}F$ reaction with $F_2$. Irradiation results in fluoride exchange and releases 15-20 µmol of carrier-added $^{18}F[F_2]$. The $^{18}F[F_2]$ in neon was carried through a teflon tube and was bubbled through the 1 mL solution of 2.2 in FC-72® at −85° C. The fluorination reaction was carried out in a FEP (perfluoroethylenepropylene co-polymer) tube, and the outlet gas was bubbled through a 0.1 N NaOH solution.

Assessment of $[^{18}F]F_2$ consumed in the reaction was determined by measuring the total radioactivity in the vessel, compared to that in the NaOH trap. Work-up involved transferring the contents of the vessel to another vial using pressure generated by a syringe. The vessel was then rinsed with HPLC grade methanol and the combined solvents were evaporated in a hot water bath under a rapid flow of nitrogen. To the resulting residue was added 3×3 mL of acetonitrile:water (1:1), and each aliquot successively transferred to the fluorous column. Fractions of 3 mL were collected and characterised.

Figure 6:
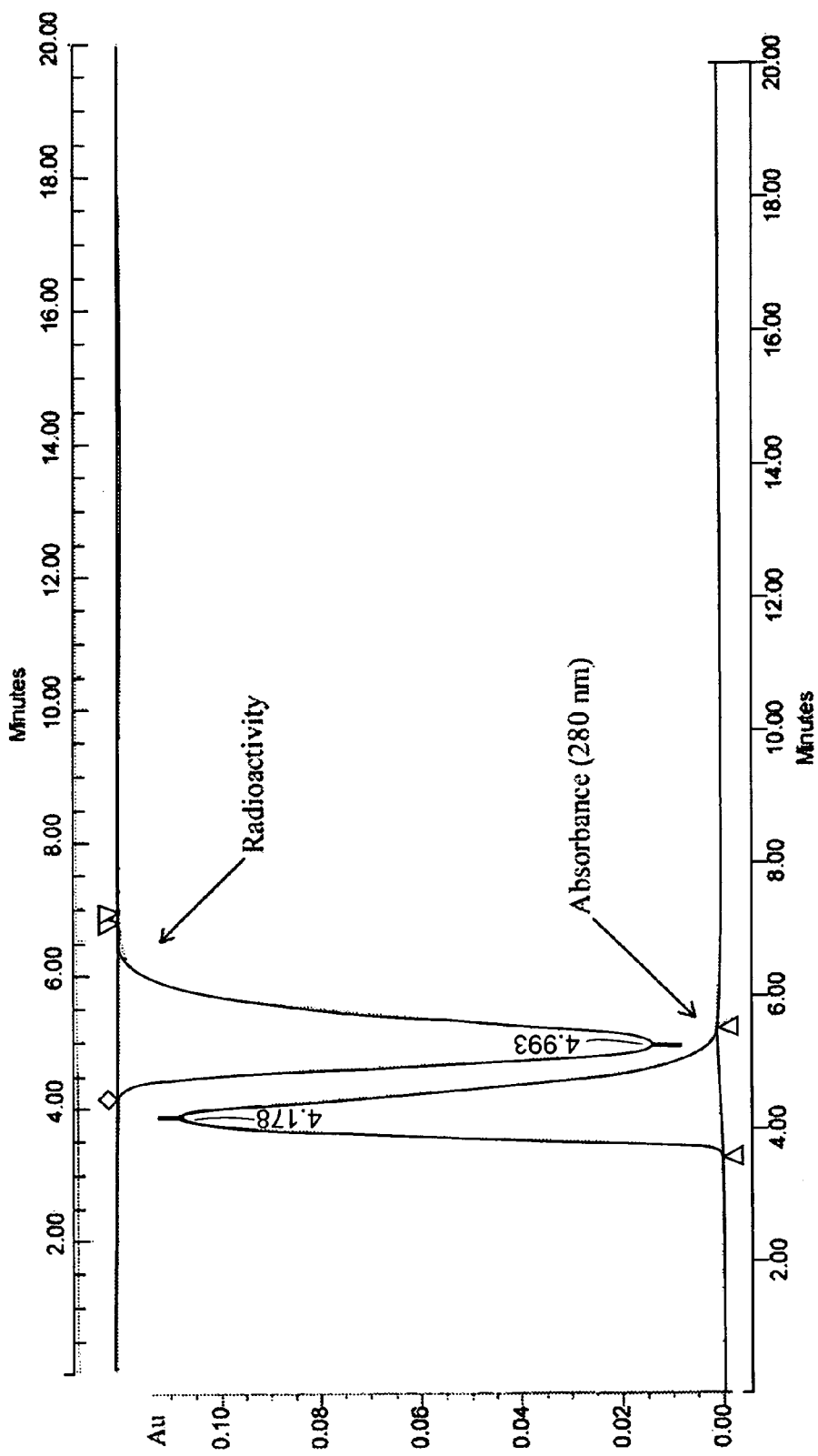
FIG. 6 depicts the UV and radioactivity chromatograms for purified 2.16.

In total, five $[^{18}F]F_2$ fluorinations of 2.2 were carried out. FIG. 6 shows the typical HPLC chromatograms which were generated. Analysis was carried out on a $C_{18}$ analytical column, eluted with a 1:1 acetonitrile:water (0.2% TFA) at 2 mL/min. The UV trace of compound 2.16 generated a single peak eluting at 4.18 minutes, which is identical to that of an authentic standard. Integration of the peak area and comparison to the calibration curve indicates a 19.4% yield of labelled product ($^{18}F$ & $^{19}F$). The radioactive trace for compound 2.16 shows a single peak eluting at 4.99 min. The later elution time is consistent with the time delay between the UV lamp and radiation detector.

In the last two reactions, the radiochemical yield and specific activity of 2.16 was assessed. In these instances, the decay corrected radiochemical yield of 2.16 was 30.2% and 11.2%; the lower yield was attributed to the vial walls not being rinsed effectively prior to purification. The theoretical maximum yield for this synthesis is 50%, as half of the activity is lost as tris(perfluorohexylethyl)tin-$[^{18}F]$fluoride. This is comparable to the $[^{18}F]F_2$ destannylation reactions where 6-$[^{18}F]$fluoro-L-DOPA and 6-$[^{18}F]$fluoro-L-m-tyrosine were generated with radiochemical yields of 33% and 23% respectively. [18,19]

The specific activity of 2.16 following purification in the two experiments was 1966 and 2899 mCi/mmol, respectively. The discrepancy can, in part, be attributed to the shorter purification times of the second vs. the first (27 min. vs 49 min.). The specific activity is dependent on the amount of $F_2$ mixed in the target gas, and as such it is difficult to make a direct comparison to other fluorodestannylation reactions. However, the obtained specific activities are reasonably high when compared to other electrophilic fluorination reactions. For example, various direct electrophilic fluorination approaches to generate 6-$[^{18}F]$fluoro-L-DOPA give specific activities of $\leq$2000 mCi/Mmol.[20,21] Though similar specific activities were obtained, this fluorous approach did not require HPLC purification.

Figure 7:
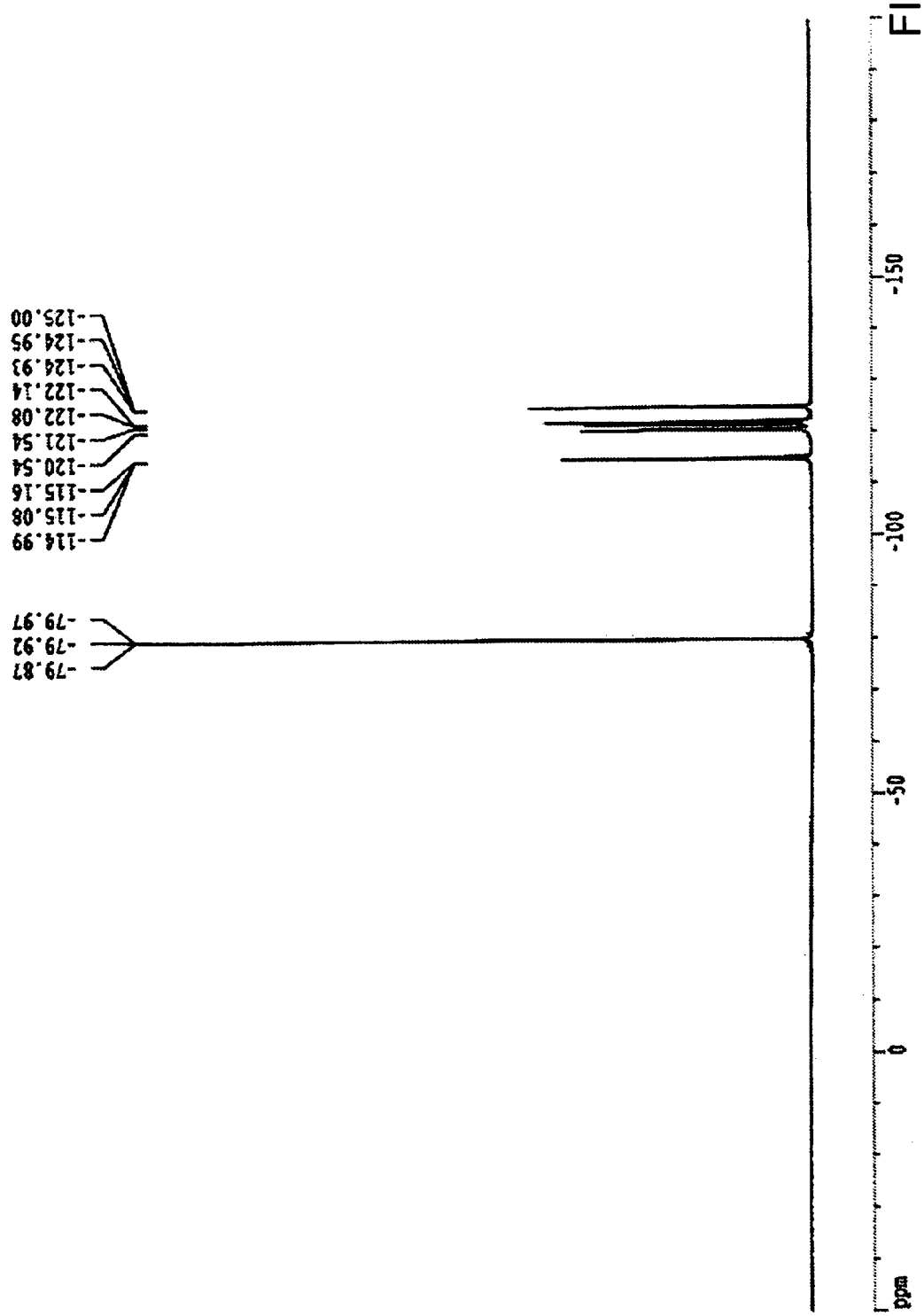
FIG. 7 depicts an $^{19}$F NMR [MeOH:ACN, 188 MHz] spectrum of the crude reaction products.
Figure 8:
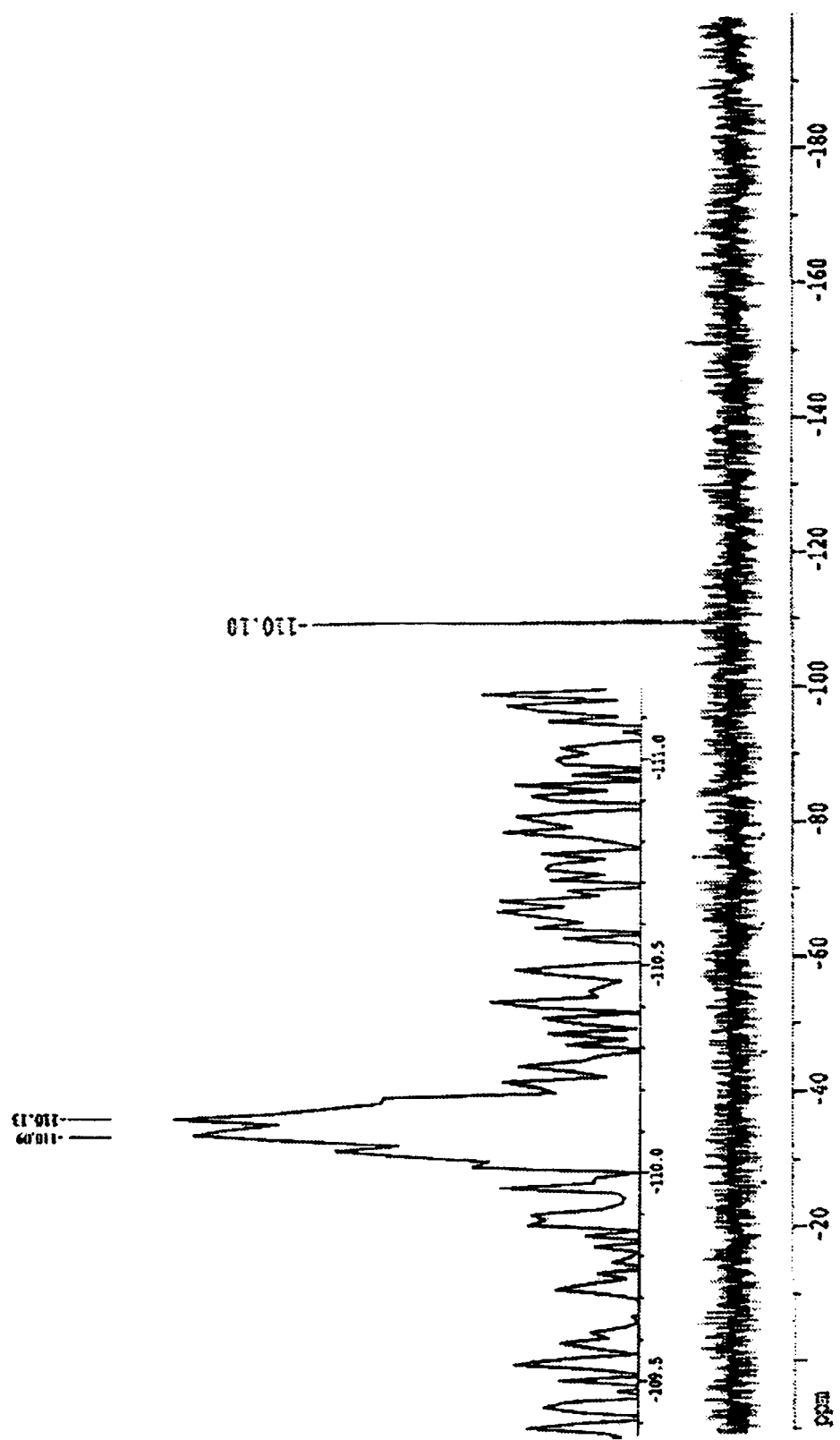
FIG. 8 depicts an $^{19}$F NMR [H$_2$O:ACN, 188 MHz] spectrum of purified 2.16.

The $^{19}F$ NMR spectra of the crude reaction products from an analogous cold fluorination and the purified reaction (2.16) products are shown in FIGS. 7 and 8, respectively. The $^{19}F$ NMR was obtained after allowing sufficient time for decay of $^{18}F$-labeled 2.16. In the $^{19}F$ NMR of crude reaction, the sensitivity of the fluorine nucleus to detection by NMR is evident in the clarity obtained following only a few scans. The crude spectrum shows six clearly resolved peaks corresponding to the six fluorine containing carbons atoms along three equivalent n-octyl chains. There was no discernible shift in these peaks prior to or following the fluorination reaction.

The $^{19}F$ NMR spectrum of the purified reaction (FIG. 8) shows only a single peak at −110.10 ppm ($^3J_{F,H}$=7.24 Hz) when run in acetonitrile:water (1:1). The peak position and coupling is consistent with an authentic standard of m-fluorobenzoic acid in which the $^{19}F$-signal appears at −109.8 ppm, and is also consistent with literature values.[16] Furthermore, it is important to note the absence of peaks associated with the fluorous "tag", which is a testament of the efficiency of the fluorous purification method.

Figure 9:
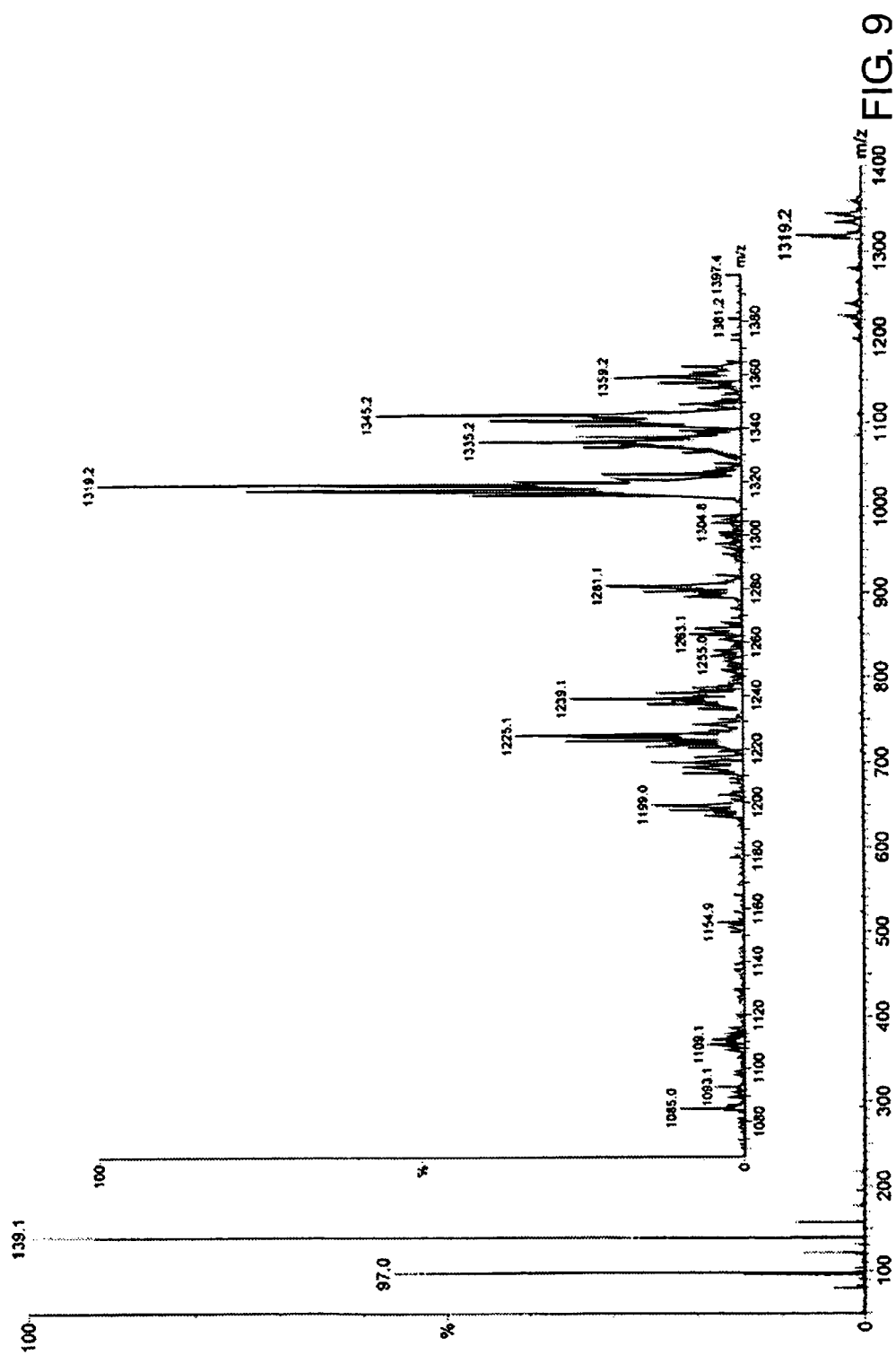
FIG. 9 depicts a negative ion electrospray of fluorinated 2.2 prior to purification.
Figure 10:
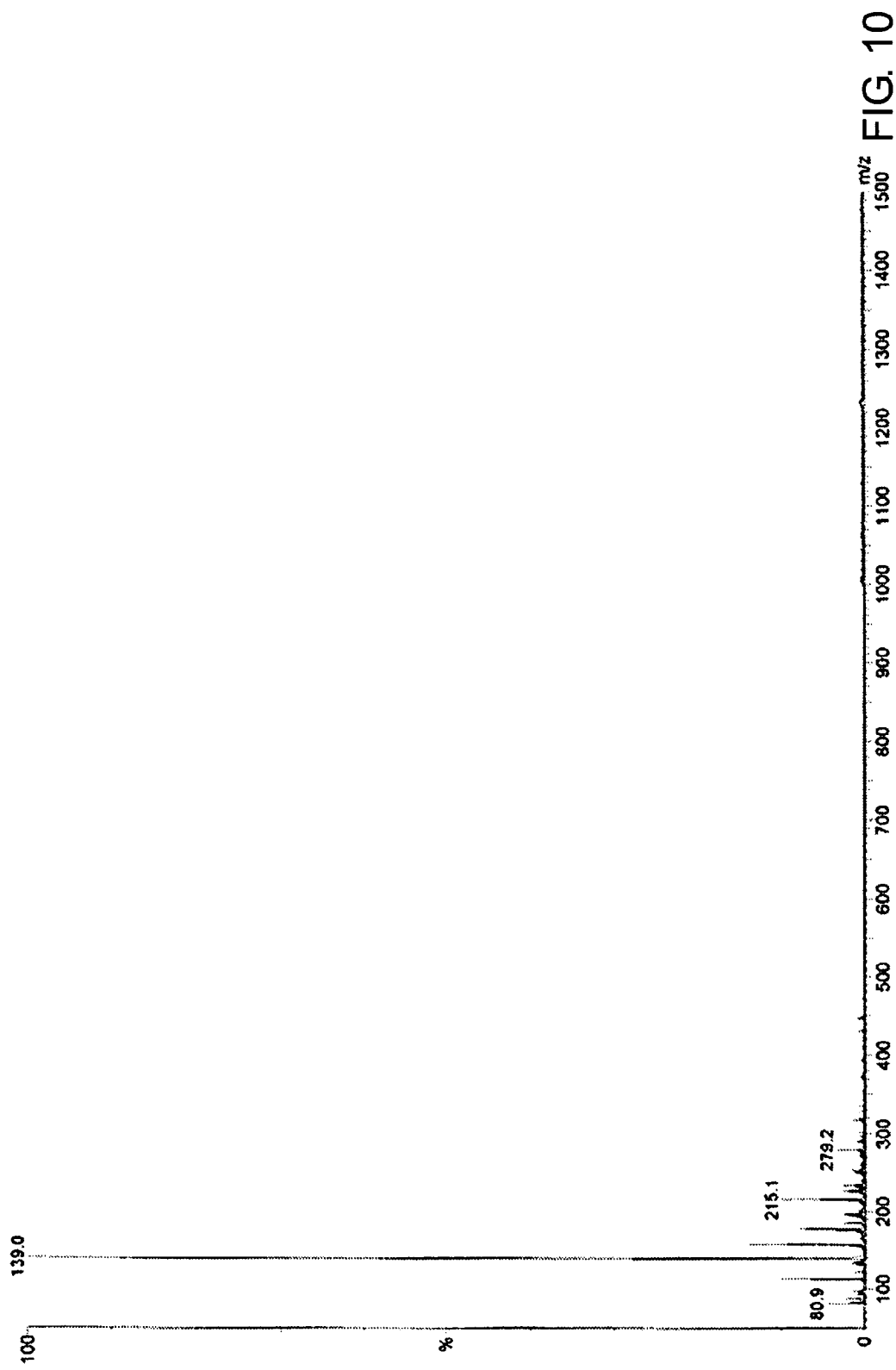
FIG. 10 depicts a negative ion electrospray mass spectrum of 2.16 (post-purification).

The negative ion electrospray mass spectrum of a crude fluorination reaction and the purified reaction of 2.16 are shown in FIG. 9 and FIG. 10, respectively. The electrospray mass spectrum of the reaction mixture prior to purification shows the product peak at m/z=139.1 [M−H]⁻ and the fluorous "tag" impurity around m/z=1319.2, 1345.2. However, the purified reaction (FIG. 10) shows only a single peak corresponding to the product at m/z=139.0 [M−H]⁻, with no trace of any impurity.

As mentioned previously, the highest radiochemical yield (EOB) obtained was 30.2%. However, it should be noted that approximately 20 mCi of radioactivity (or ≈11%) was lost during evaporation of the FC-72® solvent. It is possible that the substitution of H-atoms in FC-72® by $[^{18}F]$fluoride accounts for this loss of activity post evaporation. De Vries et al. observed a 61-73% loss of radioactivity to the reaction solvent when they switched from $CFCl_3$ to the more environmentally appropriate $CHCl_3$ or $CH_3CN$.[18] This reduced the radiochemical yield of 6-$[^{18}F]$fluoro-L-DOPA, obtained through fluorodestannylation, from 33% to 5% ($CHCl_3$) and 17% ($CH_3CN$). It appears, despite the loss of activity, that FC-72® permits higher overall radiochemical yields compared with other reaction solvents.

In developing these $[^{18}F]F_2$ reactions, it quickly became evident that a workup procedure needed to be devised to permit a more "hands-free" or automated approach. The challenge with this work-up is that the fluorophilic solvent (FC-72®/methanol) needed to be exchanged with a fluorophobic solvent (acetonitrile/water). Rotary evaporation required too much manual manipulation. Alternatively, solvent evaporation in a hot water bath under a rapid flow of nitrogen took too long and often dispersed the product.

Figure 11:
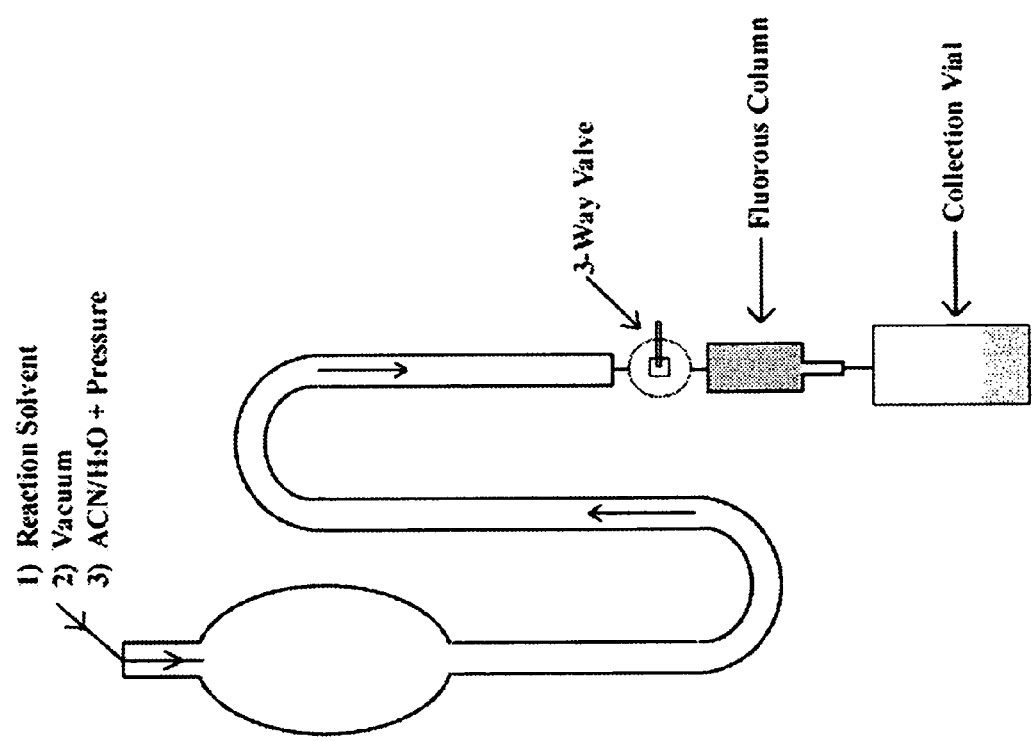
FIG. 11 depicts a novel workup apparatus.

In an attempt to improve upon these procedures, a U-tube like apparatus was constructed (FIG. 11). Following the fluorination reaction, the vessel contents could be transferred to the U-tube via syringe pressure. Applying a weak vacuum to the top of the U-tube facilitated removal of the solvent at room temperature within a couple of minutes. Addition of 3×3 mL of acetonitrile:water (1:1), followed successively with applied syringe pressure, transferred the contents to the fluorous Sep-Pak and into the collection vial. In a trial cold reaction this apparatus appeared to facilitate a more suitable "hands-free" workup.

The facile synthesis and purification of 2.16 demonstrates that the fluorous strategy shows promise as a convenient route for the preparation of $^{18}F[F_2]$ labelled radiopharmaceuticals. There is a complete removal of the fluorous "tag" through a quick and simple fluorous column purification, which requires less than a minute. This approach therefore would be appealing in certain applications, as it avoids time intensive purification, reduces exposure, and can increase overall specific activity when compared to standard methods.

Synthesis of 3-iodobenzoic acid (2.17).

With the success of the fluorination reactions, we explored labelling benzoic acid with iodine. The cold iodinolysis of the fluorous "tagged" model compound (2.2) was carried out in order to assess the capacity for introducing $^{125}$I, $^{131}$I, and $^{123}$I. In addition to being interested in simple product generation, optimising reaction conditions was also an important goal. The iododestannylation reaction of 2.2 using excess iodine is shown in Scheme 7.

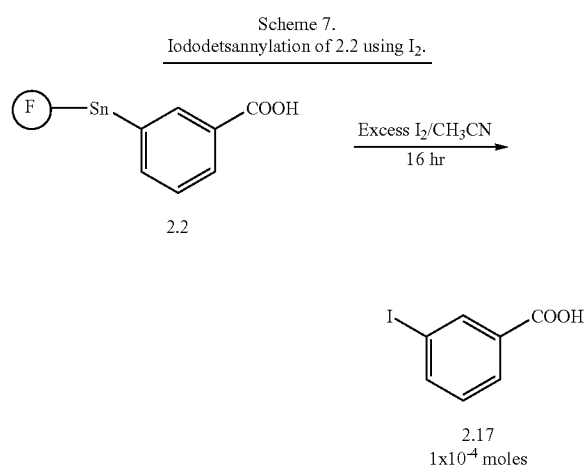

Figure 12:
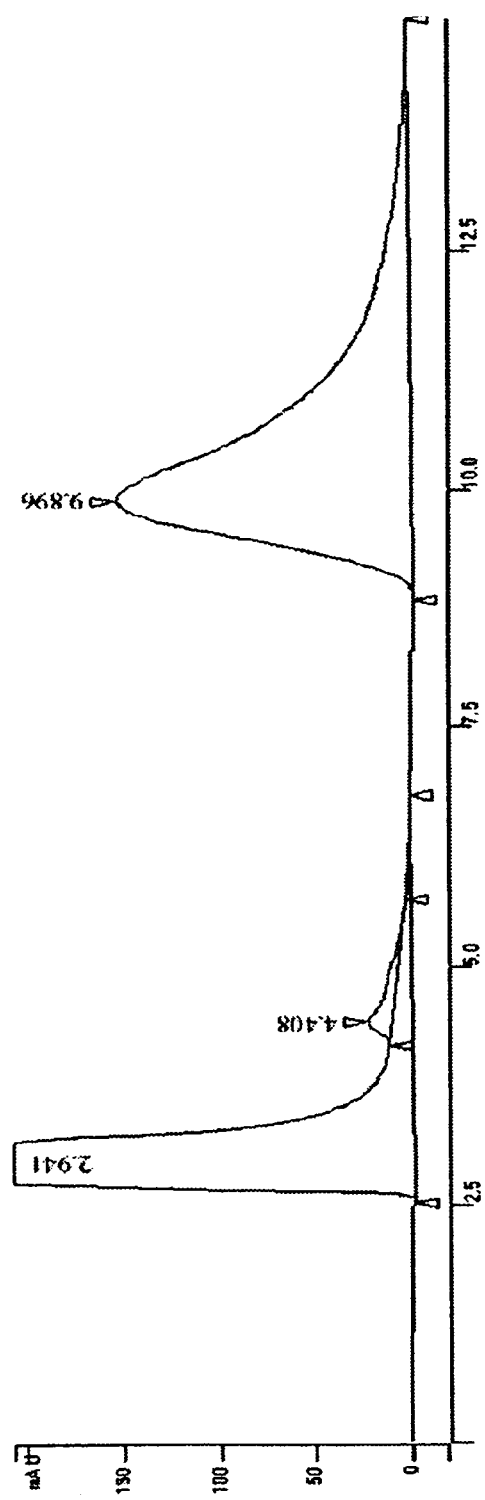
FIG. 12 depicts an HPLC chromatogram of compound 2.17.
Figure 13:
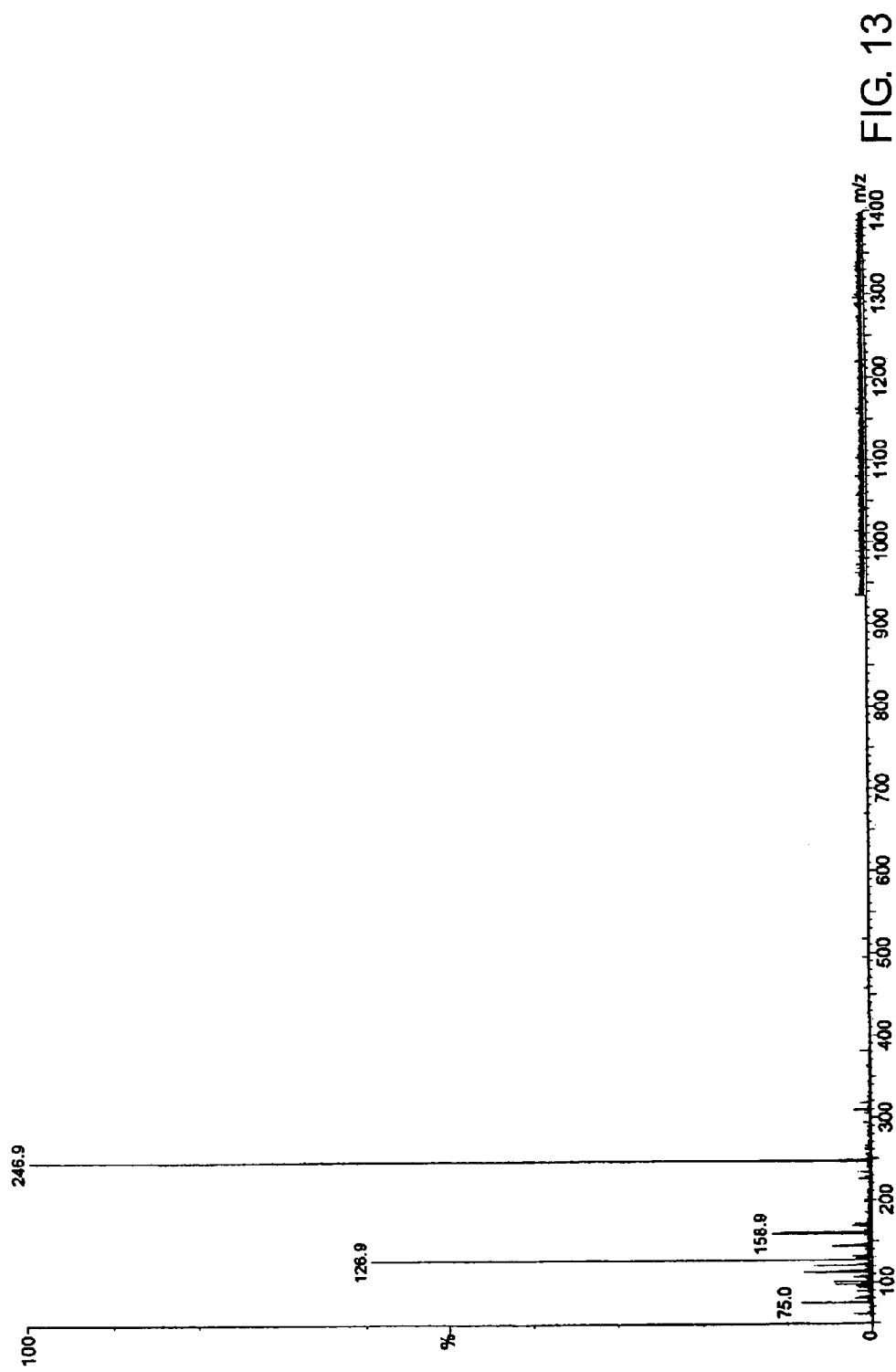
FIG. 13 depicts a negative ion electrospray mass spectrum of compound 2.17.

The iodination reaction was carried out using excess I2 dissolved in methanol, which was added to a sizeable ($1\times10^{-4}$ mol) sample of 2.2. The reaction was allowed to proceed overnight, after which sodium metabisulfite was added to quench any unreacted iodine. Methanol was removed under reduced pressure and the residue was dissolved in 5×5 mL volumes of HPLC grade acetonitrile:water (1:1), and each washing was eluted through a fluorous column. In this case, purification utilised a 3.9 g sample of loose fluorous silica (silicycle®), packed into a 40 cm narrow column. The 5 ml aliquots were assessed for purity through HPLC (FIG. 12) and electrospay mass spectrometry (FIG. 13).

The HPLC chromatogram contained three peaks, corresponding to salts (solvent front) and 2.17 ($t_R$=9.9 min). The peak at 9.9 min was shown to be 2.17 through comparison to a standard sample of 3-iodobenzoic acid.

The negative ion electrospray mass spectrum showed a single peak above background at m/z=246.9 [M−H]$^-$, which is consistent with the formation of 2.17. There was no evidence of the fluorous "tag" which would be seen at m/z>1000.

Iododestannylation of 2.2 using NaI (2.18).

The iodinolysis reactions discussed above used an excess of iodine and $10^{-4}$ moles of substrate, and are therefore not representative of radioiodination reactions. In order to develop a labelling approach towards 2.18, reactions with cold Na $^{127}$I at concentrations that mimic those that would be used with iodine radionuclides were undertaken (Scheme 8).

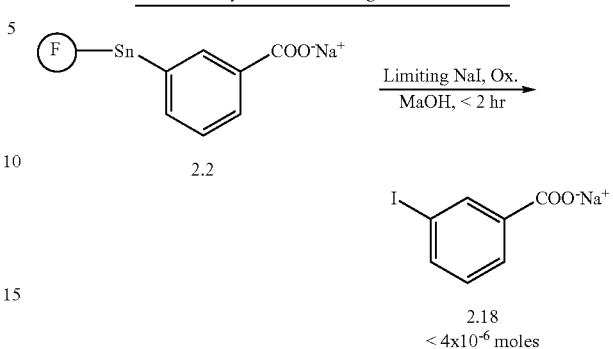

In an attempt to optimise the cold iodination reaction a number of reaction conditions were investigated. First, a wide range of oxidants, which are commonly used in radio-iododestannylation reactions, were screened. These included chloramine-T (N-monochloro-p-toluenesulfonamide), N-chlorosuccinimide, and peracetic acid. Peracetic acid showed the highest conversions, which is consistent with literature reports.[22]

The choice of solvent can also dramatically impact the radiochemical yields. For the most part, methanol was utilised because of its ability to dissolve 2.2 and has been shown to be compatible with the other reagents and reaction conditions. Iodination reactions are also highly dependent on the pH of the solvent, generally being promoted in an acetic medium and sometimes arresting when the pH increases towards neutrality.[23] For this reason, researchers often add small quantities of HCl or acetic acid to the reaction; however, it was found that the oxidant (32% peracetic acid in acetic acid) was adequately acidic to promote the aforementioned reaction.

In addition to optimising the reaction conditions, detection of the very small quantity of product (2.18) being generated necessitated optimising the HPLC conditions. It was found through lengthy trial and error that separation of 2.18 from salts in solution could not be exacted using a C-8 analytical column. This problem was rectified by switching to a C-18 analytical column which facilitated significant separation.

In the end, the optimum reaction involved dissolving compound 2.2 (Na$^+$ salt) ($4\times10^{-6}$ mol) in methanol (200 μL) with stirring. To this solution was added NaI (4 μL, $1.8\times10^{-7}$ mol) in 0.1 N NaOH, which was followed immediately by the addition of freshly prepared peracetic acid solution (2 μL). The reaction was quenched after 2 hours with excess sodium metabisulfite and diluted to 1 mL with distilled deionized water.

Figure 14:
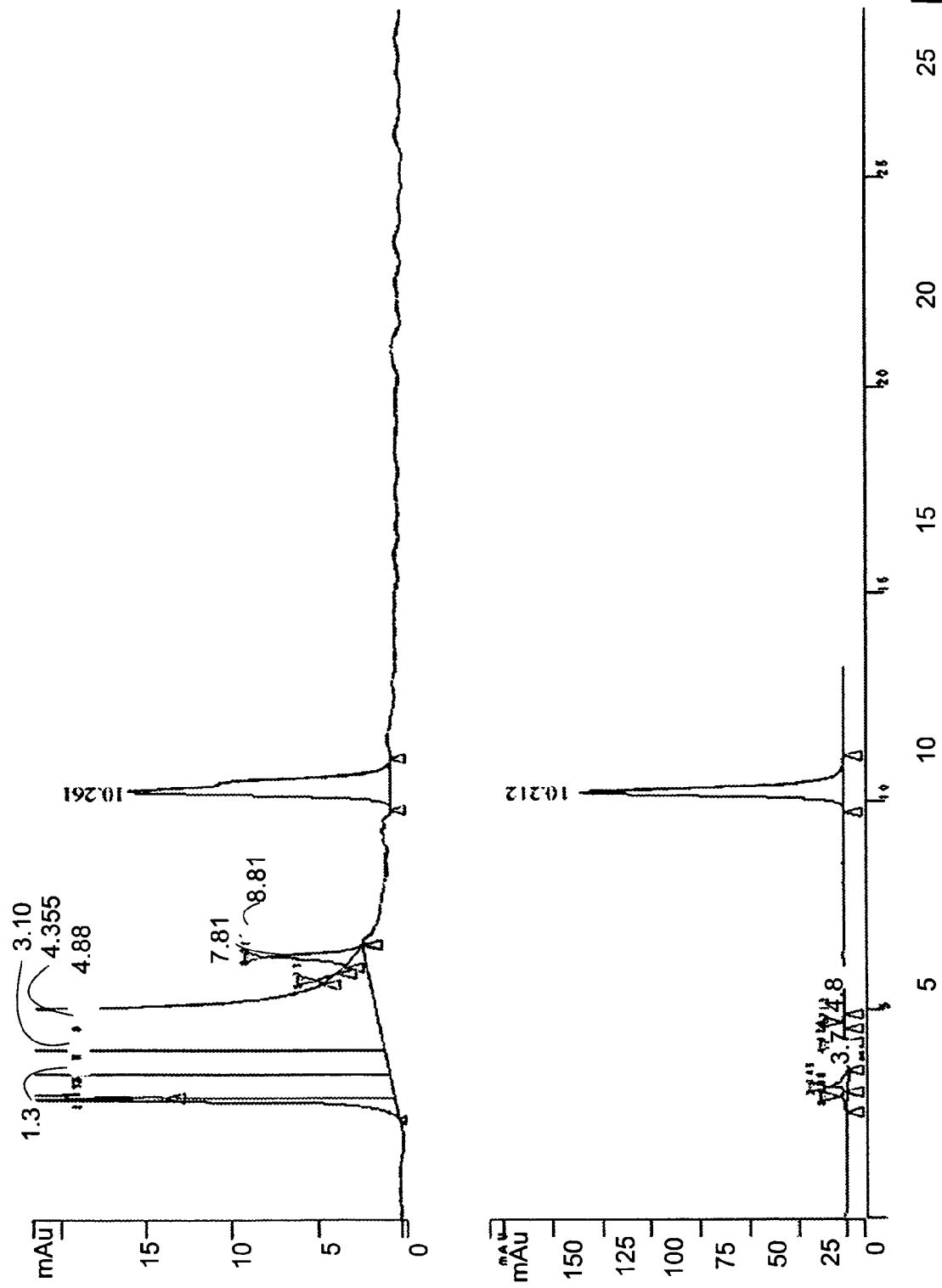
FIG. 14 depicts an HPLC chromatogram of 2.18 (above) and authentic standard (below).

The HPLC chromatogram of compound 2.18 shows two primary peaks with elution times of 4.8-6.3 min. and 10.3 minutes, corresponding to salts (solvent front) and 2.18 respectively (FIG. 14). An authentic standard of 3-iodobenzoic acid under the same elution conditions produced a peak at 10.2 minutes, confirming the peak assignment.

The advantage to developing this chemistry using a cold isotope, similar to the case of fluorine, was that reactions could be conducted and handled without risk of exposure.

However, the difficulty in developing radiochemical labelling procedures with representative quantities of Na $^{127}$I for Na$^{125}$I, was that detection had to be based solely on ultraviolet absorption. Comparatively, the use of 400 µCi (approx. 1.8×10$^{-7}$ mol) Na $^{125}$I would result in an extremely intense peak on a gamma detector, although a very small, if visible, ultraviolet absorbance. Recall that the maximal incorporation of iodine into the target molecule is ≦50% of the total; therefore, in an analogous 400 µCi reaction, the maximum product yield is ≦9×10$^{-8}$ moles.

Synthesis of 3-[$^{125}$I]iodobenzoic acid (2.19)

The successful cold labeling of 2.2 using cold NaI prompted the corresponding radioiododestannylation using Na $^{125}$I (Scheme 9).

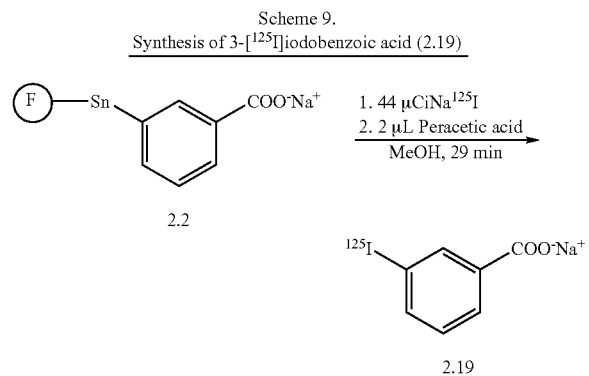

The reaction was conducted in a similar fashion to the cold iododestannylation reactions. Compound 2.2 (Na$^+$ salt) (9×10$^{-4}$ mol) was dissolved in 200 µL of methanol with stirring, prior to the addition of Na$^{125}$I (44 µCi) in approximately 200 µL of 0.1 N NaOH solution, and 2 µL of fresh peracetic acid. The reaction was allowed to stir for 29 min prior to quenching with sodium metabisulfite (100 µL).

Figure 15:
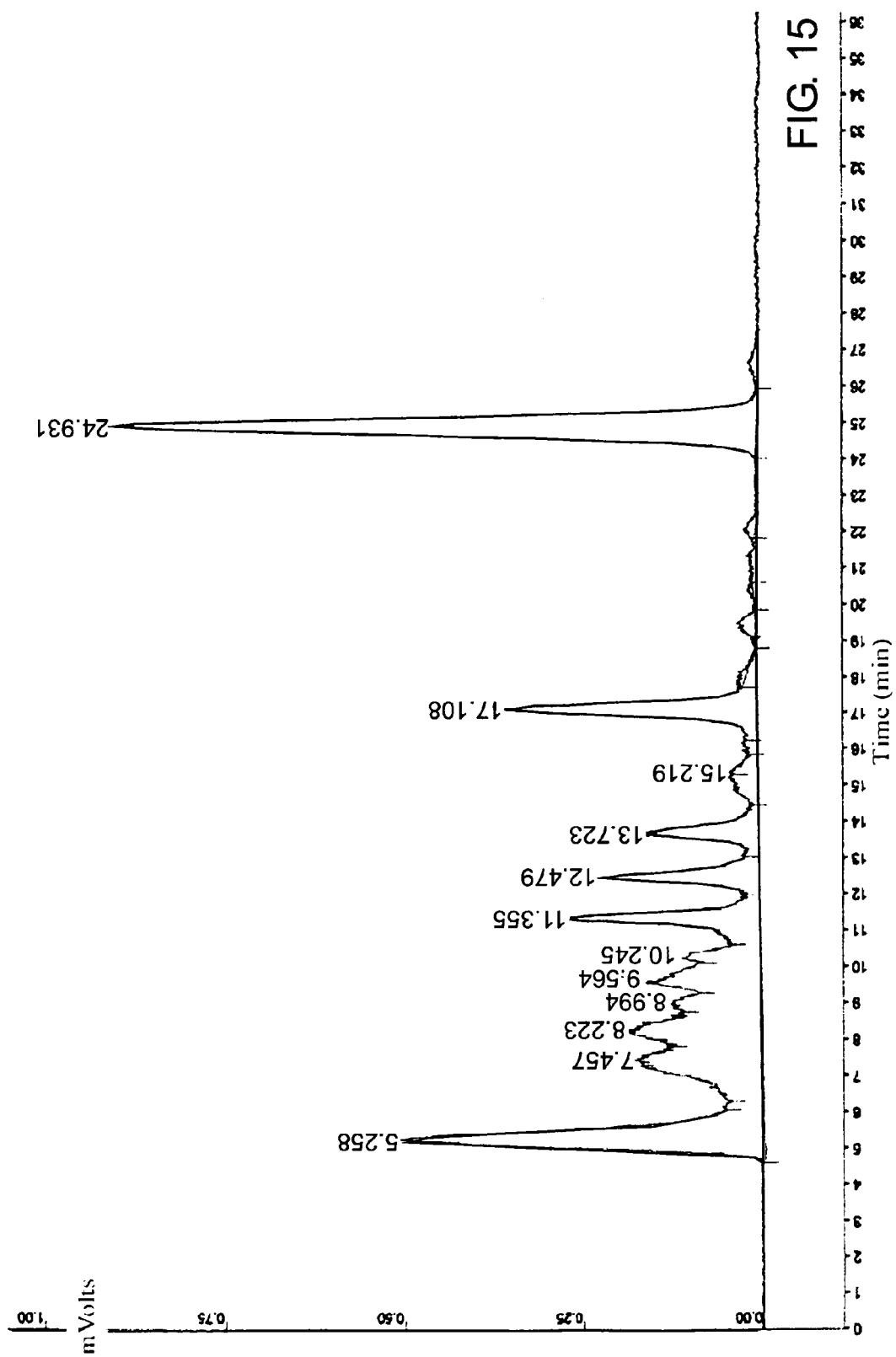
FIG. 15 depicts an HPLC chromatogram of the crude reaction mixture for 2.19.

A 20 µL aliquot of the crude reaction mixture was injected onto the HPLC for analysis. The UV trace revealed only a single peak corresponding to the solvent front, while the radioactivity chromatogram showed several peaks (FIG. 15). The peak at 5.3 min is coincident with the solvent front and presumably represents free $^{125}$I. The peak at 17.1 min was confirmed to be 2.19 through injection of the standard 3-iodobenzoic acid. However, the identity of the other extraneous peaks, particularly the large peak at 24.9 min could not be assigned at the time of the reaction.

Figure 16:
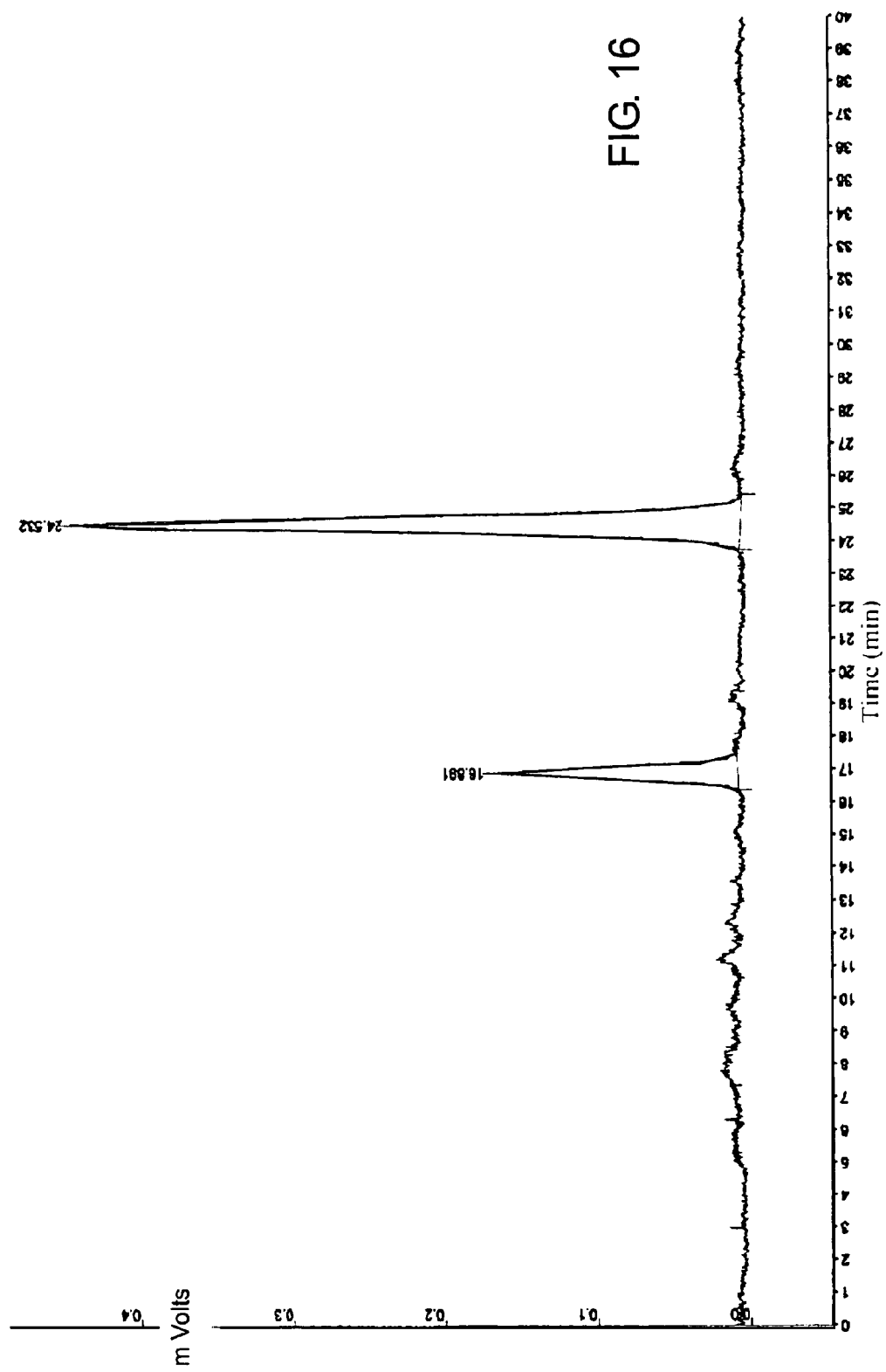
FIG. 16 depicts an HPLC chromatogram 2.19 following Sep-Pak purification.

Although the quality of the crude reaction mixture containing 2.19 is less than ideal, a simple purification was undertaken to illustrate our capacity to remove any unreacted free $^{125}$I in solution. The aforementioned crude reaction mixture was diluted with 500 µL of water and added to a conditioned C18 Sep-Pak. The Sep-Pak was eluted with 2 mL of distilled deionized water to remove unbound $^{125}$I, followed by elution with 1 mL of methanol. HPLC analysis of a 20 µL aliquot of the methanol fraction is shown in FIG. 16. The chromatogram reveals that essentially all of the radioactive impurities up to 2.19 ($t_R$=16.9 min) are removed by washing the column with water. Further, taking into account dilution, most of 2.19 was eluted with the 1 mL of methanol. However, the then unidentified peak at 24.5 minutes was still present.

The less-than favourable results obtained in the above reaction prompted another reaction with a fresh source of Na$^{125}$I. In this reaction, compound 2.2 (Na$^+$ salt) (1.1×10$^{-6}$ mol) was dissolved in 200 µL of methanol with stirring, prior to the addition of Na$^{125}$I (32 µCi) in approximately 5 µL of 0.1 mM NaOH solution, followed by 2 µL of a freshly prepared solution of peracetic acid. The reaction was allowed to stir for 47 min, prior to quenching with excess sodium metabisulfite (20 µL) and dilution with 300 µL of distilled-deionized water.

Figure 17:
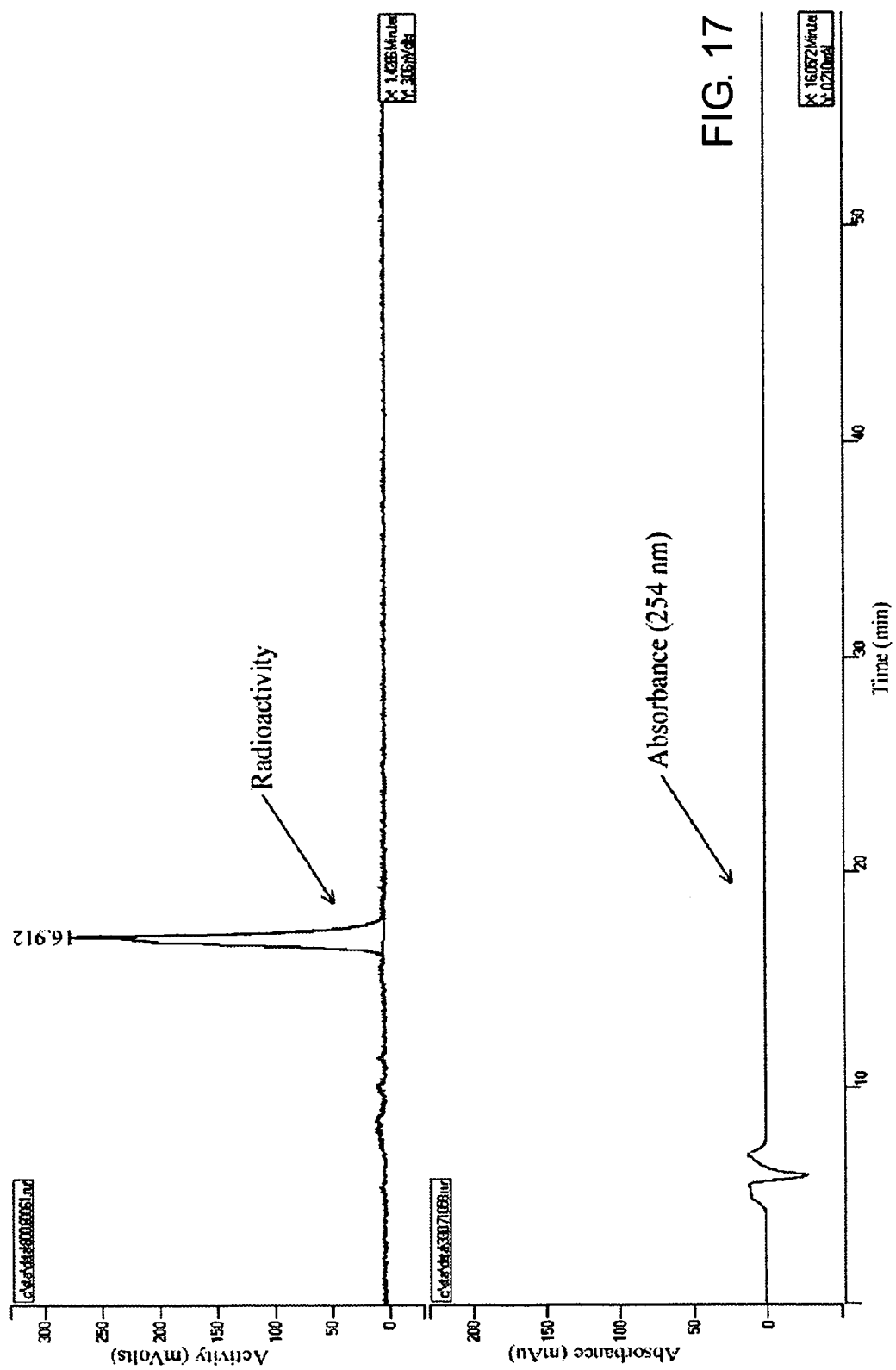
FIG. 17 depicts an HPLC chromatogram of the crude reaction mixture for 2.19.

A 20 µL aliquot of the crude reaction mixture was injected onto the HPLC for analysis. The UV trace revealed only a peak representative of the solvent front, while the radioactivity chromatogram showed a peak with a retention time of 16.91 min (FIG. 17). The peak is consistent with the formation of 2.19, confirmed by injection of 3-iodobenzoic acid, which elutes at 15.86 min. The difference in retention times is a result of the time delay between the UV and radiation detectors.

The radioactivity chromatogram of the crude reaction mixture illustrates that 2.19 was essentially generated in quantitative yield with no significant contribution of unbound/unreacted iodine. The radiochemical purity of crude 2.19 was ≧90%. This level of incorporation and purity in a crude iododestannylation reactions is uncommon, especially given the short reaction time.

Although there is a little evidence for the presence of unbound iodine or radiolabelled salts in the reaction mixture, a short purification was undertaken to indicate that they could in the future be removed from the product. The reaction solution was diluted with approximately 1.5 mL of water and passed down a C$_{18}$ Sep-Pak column, conditioned with methanol. The column was further washed with 1.5 mL of water, and these fractions combined. The Sep-Pak was then eluted with 2 mL of acetonitrile and collected into a separate vial. The acetonitrile faction contained 72% of the activity, and further elution of the column with acetonitrile released only small additional amounts of activity. A total of 4 µCi was bound to the Sep-Pak column, likely the more highly retained and radiolabelled fluorous "tag" (R$_3$Sn$^{125}$I). The other activity was found in the water (3 µCi), the reaction vessel (1 µCi), and in an additional 1 mL washing of the Sep-Pak with acetonitrile (1 µCi). HPLC analysis of the fraction containing the majority of the activity displayed a single peak in the radiochromatogram corresponding to 2.19 at 16.59 minutes. The final radiochemical yield of purified 2.19 was 75% with respect to the total Na$^{125}$I activity utilised. Yields of this magnitude are uncommon, considering that the maximum theoretical radiochemical yield should be less than or equal to 50%. The results of Hunter et al. are fairly representative of a radioiododestannylation reaction. They observed a 50.8% radiochemical yield of [$^{131}$I]MIBG; 44% of the activity was bound to tin and 5.1% was free $^{131}$I$^-$ in solution.[23]

Figure 18:
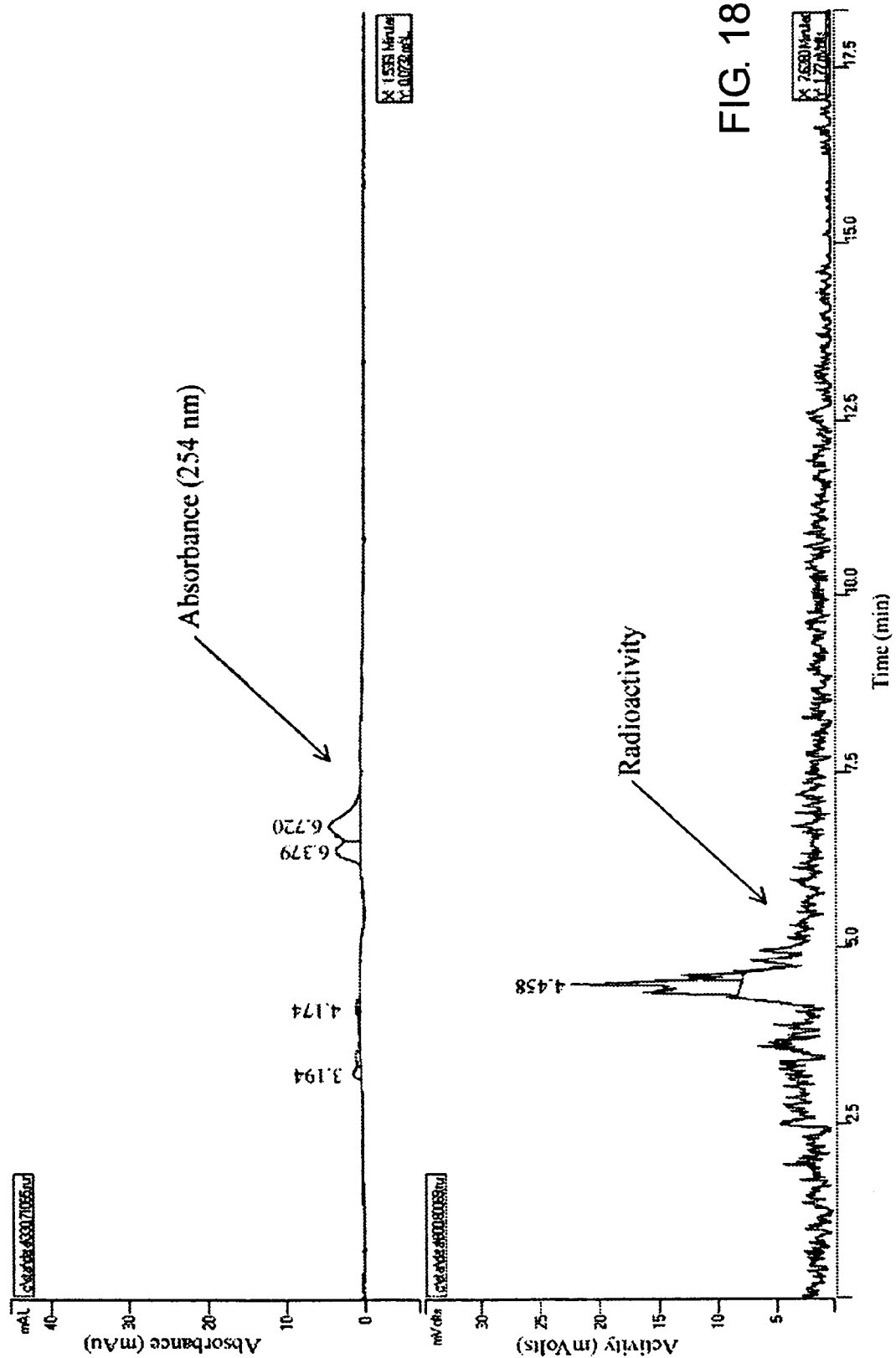
FIG. 18 depicts an HPLC chromatogram of 2.19 following Sep-Pak purification.

Given the high radiochemical yield, it became important to quantify the purity of [$^{125}$I]-3-iodobenzoic acid with regards to any labelled or unlabelled precursor 2.2. As mass spectrometry and $^{19}$F NMR are not feasible for $^{125}$I labelled compounds, we had to rely on HPLC analysis. Elution of the precursor 2.2 on a C$_{18}$ analytical column with 100% acetonitrile generated a UV peak at 6.61 minutes. Similarly HPLC analysis of the Sep-Pak purified faction exhibited peaks at 3.19-4.17 min, corresponding to the solvent front, and 6.38-6.72 min, likely corresponding to 2.2 (FIG. 18). The radioactivity chromatogram showed only a single peak at the solvent front, 4.46 min, corresponding to the 2.19. A radioactivity peak corresponding to a labelled fluorous "tag" product would be predicted to elute in a similar position to 2.2; however, this is not seen. This indicates that our previous radiochemical yield of 75% is accurate, though there appears to be some unreacted 2.2 present in this reaction solution.

Figure 19:
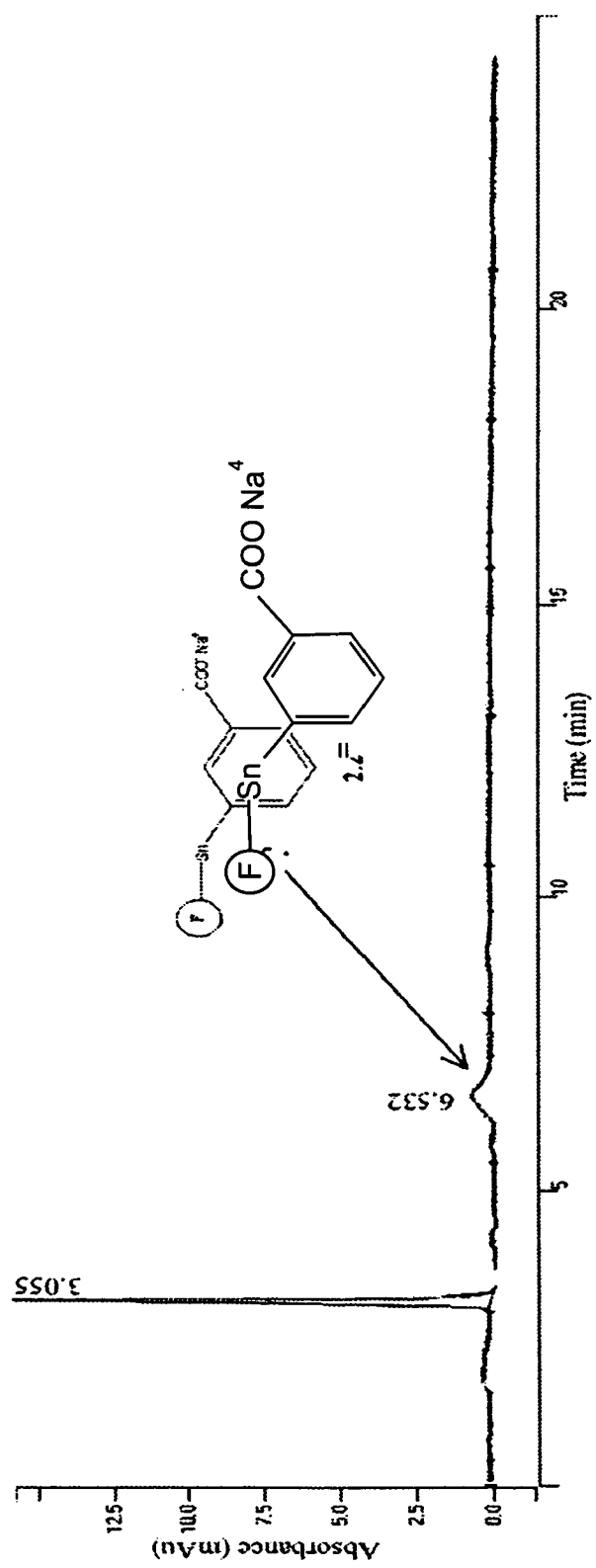
FIG. 19 depicts a UV chromatogram of 2.19 purified down a fluorous column.

It has previously been established that even large quantities (>200 mg) of the "fluorous tag" can readily be removed using a fluorous column and an acetonitrile:water (1:1) mobile phase. This system can therefore readily facilitate the removal of the much smaller quantities of substrate (1.4 mg) used in this and other typical radioiodination reactions. In order to demonstrate this purification approach, 2.19 in acetonitrile was diluted with an equal volume of distilled-deionized water and passed down a conditioned fluorous column. Washing the column with an additional 4 mL of acetonitrile:water (1:1) liberated all the activity (19 µCi). Analysis of an aliquot of this solution showed, upon expansion of the chromatogram, a solvent peak at 3.055 min and a small peak at 6.53 min (FIG. 19).

Because we have shown that the fluorous Sep-Pak can remove large quantities of the fluorous "tag", the peak at 6 minutes likely arose through another source. One possibility is that the fluorous column, which had been recycled from another reaction, might not have been adequately cleaned. Alternatively, since fluorous material is prone to sticking to the HPLC loop, it is possible that accumulated material was released into this injection.

Summary

A method was developed to prepare tris(perfluorohexyl-ethyl)tin-3-benzoic acid and to label this material with fluorine and iodine. The fluorous approach using both hot and cold $F_2$ and $I_2$ was effective in generating the desired products. Additional experiments are needed to optimise the reactions, particularly with respect to purification protocols.

Developing Coupling Procedures—Benzamide Synthesis

Initially, the rationale behind the synthesis of 2.2 lied in permitting the facile radiolabelling of peptides/biomolecules through coupling to labelled benzoic acid. The successful synthesis and labelling of 2.16 and 2.19 encouraged the synthesis of more complex compounds. One such approach that would benefit from, and extend the utility of, compound 2.2 would be its conversion to biologically active derivatives.

Radioiodobenzamide

Radioiodobenzamides, or N-Alkyl-iodobenzamides, constitute a new class of important radiopharmaceuticals.[24] Exhibiting a high affinity towards $\sigma_1$ and $\sigma_2$ receptors, radioiodobenzamides are currently the best known radiopharmaceuticals for the diagnosis of cutaneous melanoma and its metastases.[24] This class of compounds have also been found to bind strongly to dopamine receptors, and are therefore effective imaging agents for diagnosis of Parkinson's and schizophrenia.[25] One of the most clinically relevant compounds is [$^{123}$I]-N-(2-diethylaminoethyl)-4-iodo-benzamide ($^{123}$I-BZA), which possesses ideal properties for melanoma scintigraphy.[26]

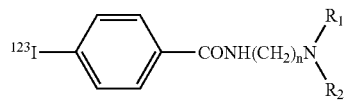

[$^{123}$I]-BZA: n = 2; $R_1$ = $R_2$ = $C_2H_5$
[$^{123}$I]-N-alkyl-p-iodobenzamides and $^{123}$I-BZA.

Currently, the most facile route to $^{123}$I-BZA involves an isotope exchange reaction ($^{123}$I for $^{127}$I). This method affords a carrier-added product resulting in reduced image quality. A more ideal strategy, which would lead to a no-carrier-added product, is radioiododestannylation of a trialkyltin precursor, which has been developed by Moreau et al.[26] With this in mind, the fluorous synthesis approach would seem suited for synthesis of radiolabelled benzamides and would avoid the need for exhaustive purification.

The aim of this project was the synthesis of iodobenzamide, 2.20, through an iododestannylation reaction of a corresponding fluorous "tagged" precursor (2.21) (Scheme 10). The synthesis of 2.20 requires the development of a new coupling methodology.

Scheme 10.
The target compound, N, N-dimethyl-m-iodobenzamide

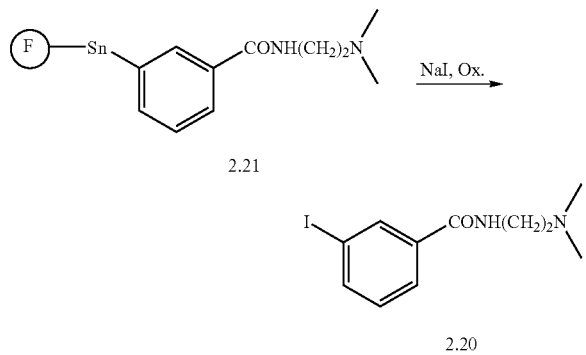

Synthesis of tris(perfluorohexylethyl)tin-3-benzamide (2.21)

The approach towards the synthesis of 2.21 concentrated on adapting traditional peptide synthesis procedures. The success of these reactions was qualified through $^1$H-NMR and electrospray mass spectrometry. Integration of the ethylene protons ($NCH_2CH_2N$) with respect to the protons positioned α and β to tin served to quantify the extent of derivatization. Initially, carbodiimide activating agents such as diisopropylcarbodiimide (DIC) and EDC were employed; however, they led to little detectable product formation. It was difficult to determine if the lack of reaction was due to the reagent or the reaction solvent. In most instances, good solvents for the coupling reagents proved to be poor solvents for 2.2, and visa versa. While coupling reactions were promoted in polar aprotic solvents such as acetonitrile and DMF, compound 2.2 was generally solvated by only extremely non-polar solvents. Solvents such as THF, which solvated both 2.2 and DIC, did not result in conversion to 2.21. EDC had another drawback. EDC contains an ammonium salt which proved acidic enough to result in the cleavage of >30% of the tin aryl bonds.

Successful synthesis of 2.21 employed the use of the coupling reagent HBTU (2-(1H-Benzotriazol-lyl)-1,1,3,3-tertramethyluronium hexaflurophosphate) in DMF (Scheme 11). HBTU promotes couplings by readily generating an activated intermediate concurrent with the formation of a urea byproduct. This activated complex reacts with amines with the subsequent loss of 1-hydroxybenzotriazole (HOBt) (Scheme 12).

Scheme 11.
Mechanism of HBTU promoted peptide coupling.

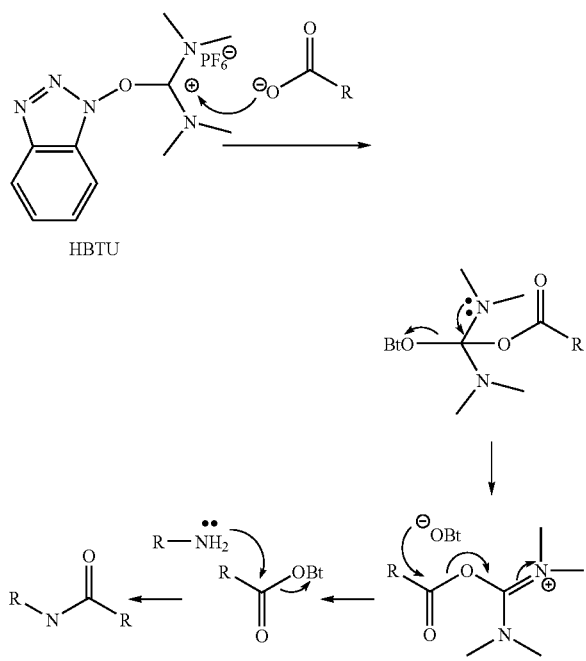

Scheme 12.
Synthesis of perfluorotin-3-benzamide (2.21) using HBTU.

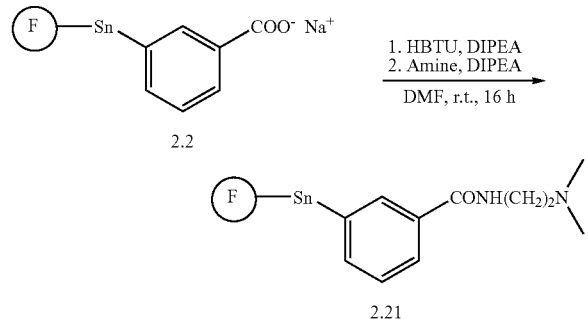

Reaction of HBTU and compound 2.2 (Na⁺ salt) was carried out in DMF in the presence of DIPEA for 5 min, prior to addition of the amine. Experiments have shown that this incubation leads to a dramatic improvement in coupling rates and yields.[27] Following addition of excess N,N-dimethylethylenediamine in an equivalent of DIPEA, the reaction was allowed to stir for 16 hours.

Due to the high solubility of 2.21 in DMF, water was added to facilitate extraction of fluorous compounds into dichloromethane and FC-72®. The more organic 2.21 could then be selectively extracted into dichloromethane from FC-72®. Several more extractions into dichloromethane yielded pure 2.21, while unreacted 2.2 remained in FC-72®. Compound 2.21, a dark yellow oil, was obtained in satisfactory yield (74%). The substantial difference in $R_f$ values between 2.21 and 2.2 (0;0.21), suggests that chromatographic purification would likely be a more appropriate and higher yielding purification method for the future.

Figure 20:
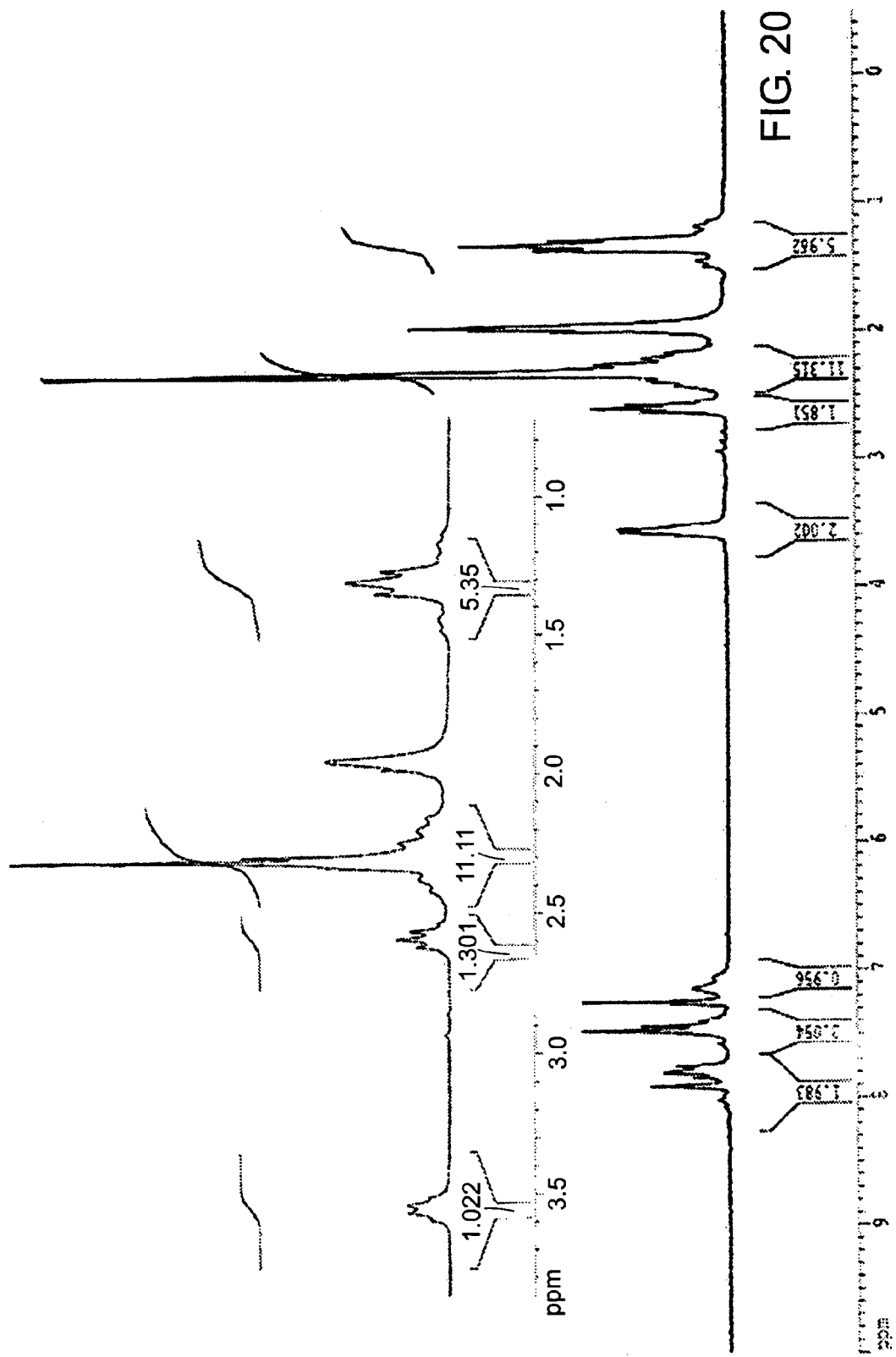
FIG. 20 depicts an $^1$H NMR [CDCl$_3$, 200 MHz] of compound 2.21.
Figure 21:
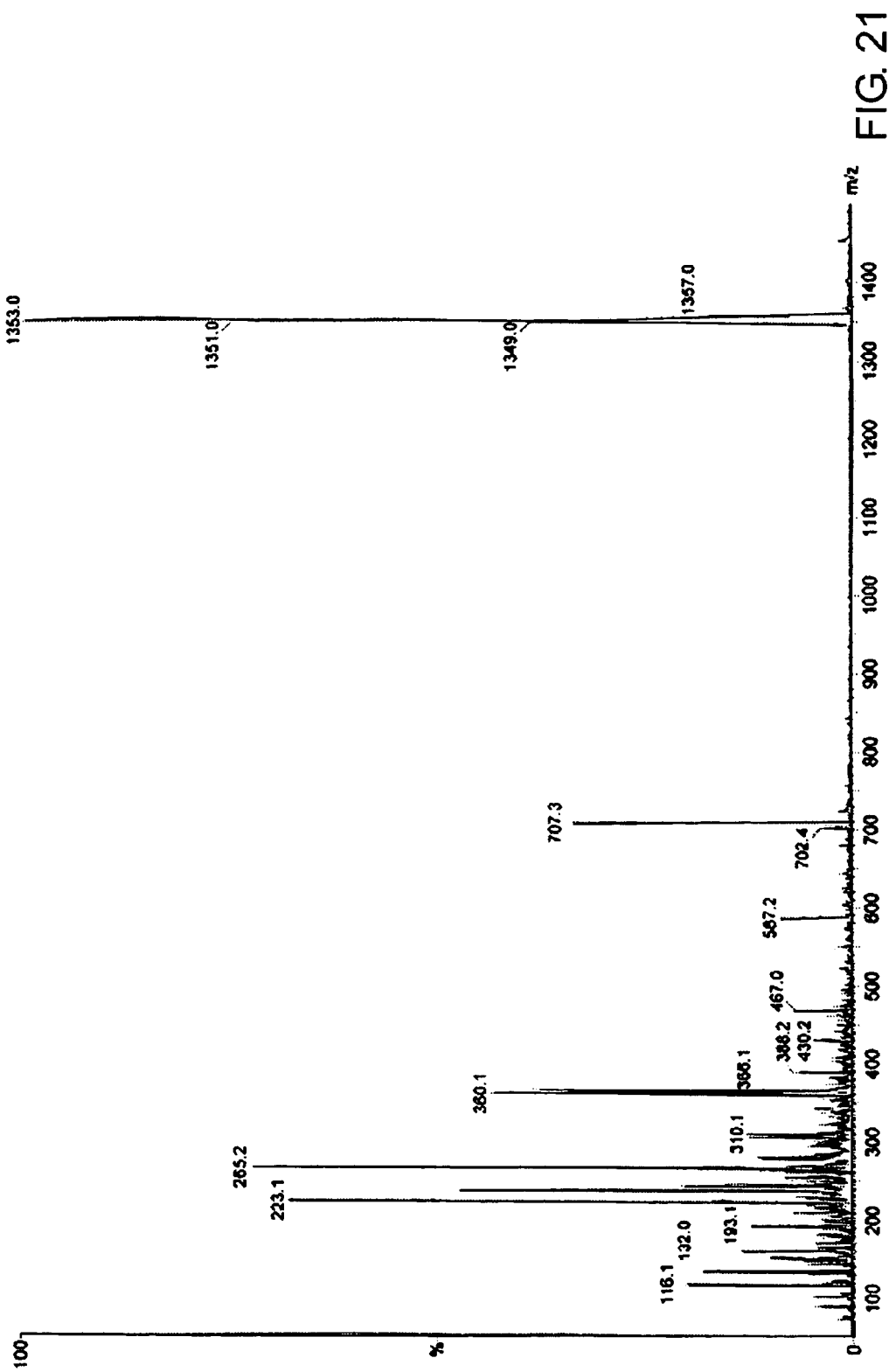
FIG. 21 depicts a positive ion electrospray mass spectrum of compound 2.21.

The ¹H NMR spectrum of compound 2.21 (FIG. 20) revealed a triplet at 1.31 ppm with Sn s atellites ($^2J_{Sn,H}$=54.8Hz) and a partially obstructed multiplet at approximately 2.33 ppm, corresponding to the protons positioned α and β to the tin respectively. In addition, the ¹H NMR showed a broad singlet at 2.31 ppm (6H), a pseudo triplet at 2.59 ppm (2H), a pseudo quartet at 3.55 ppm (2H), and the expected aromatic peaks from 7.39-8.01 ppm (4H). The ¹³C NMR of 2.21 showed at low field peaks at −1.43 ppm, 27.55 ppm ($^2J_{F,C}$=23.4 Hz), 37.11 ppm, 44.87 ppm, and 57.75 ppm. The ¹³C NMR at higher field had resonances from 104.80 ppm to 120.03 ppm corresponding to the carbon atoms with attached fluorines and aromatic signals which have yet to be assigned. The IR of compound 2.21 showed aromatic stretches at 2900 cm, in addition to the C=O absorption at 1650 cm⁻¹ and N—H stretch at 3338 cm⁻¹. The mass spectrum of 2.21 (FIG. 21) showed, in the positive ion mode, a single peak at m/z=1353 [M+H]⁺. Importantly, the negative ion mass spectrum of the same compound did not show the precursor peak at m/z=1279 [M-H]⁻

Synthesis of 3-iodobenzamide (2.20)

The iododestannylation of compound 2.21 and purification of the product 2.20 was carried out in a similar manner to that used for compound 2.2 (Scheme 13).

Scheme 13.
Synthesis of 3-iodobenzamide (2.20).

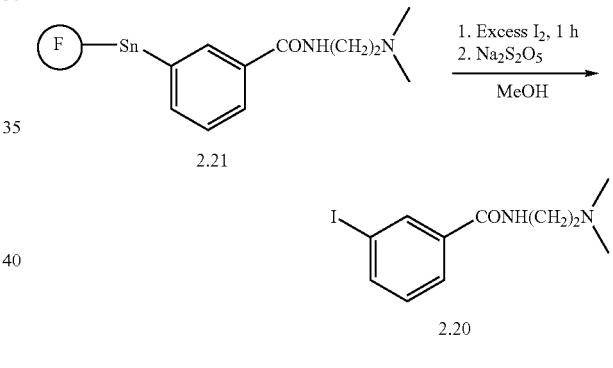

Figure 22:
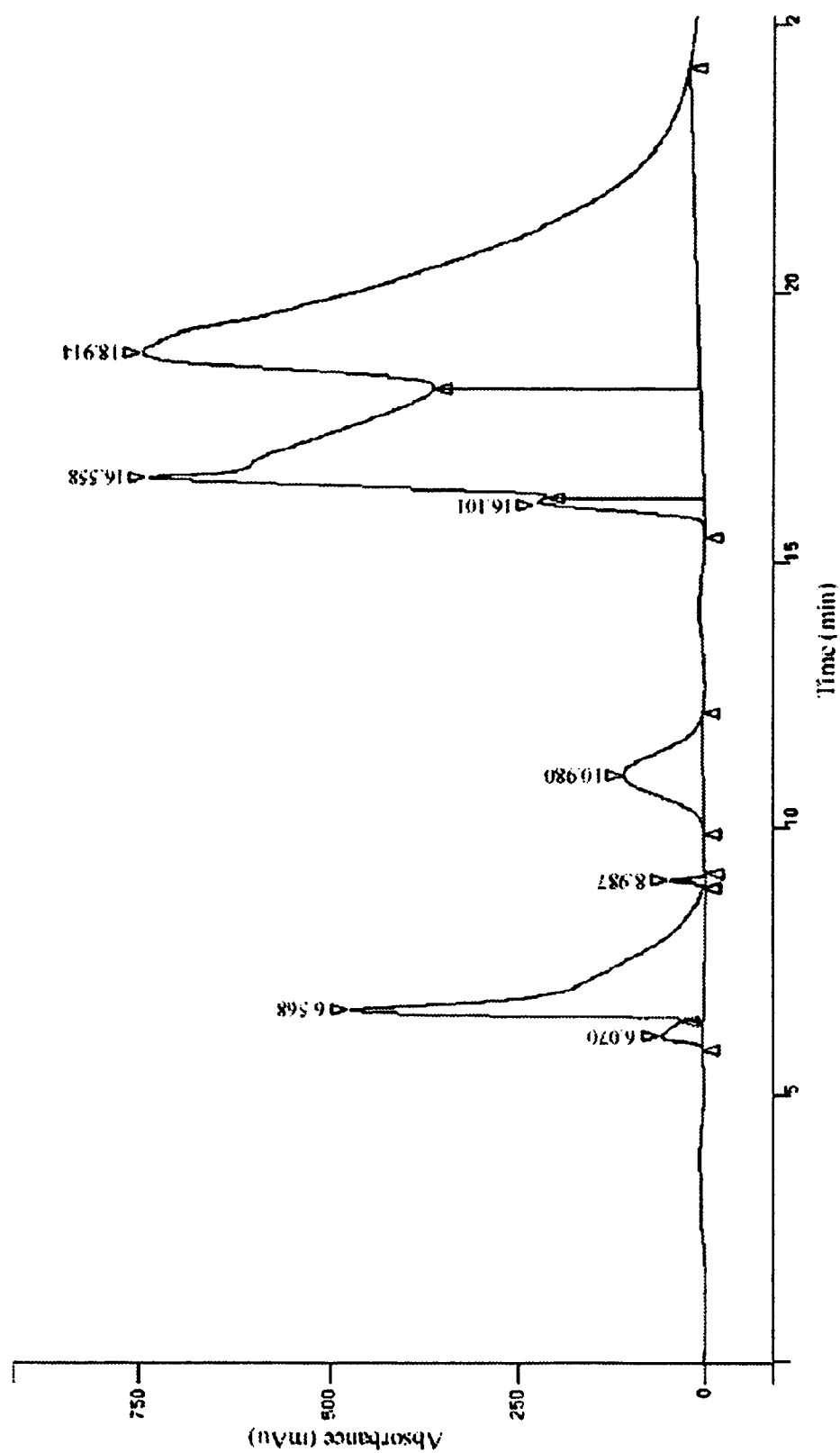
FIG. 22 depicts an HPLC chromatogram of compound 2.20.
Figure 23:
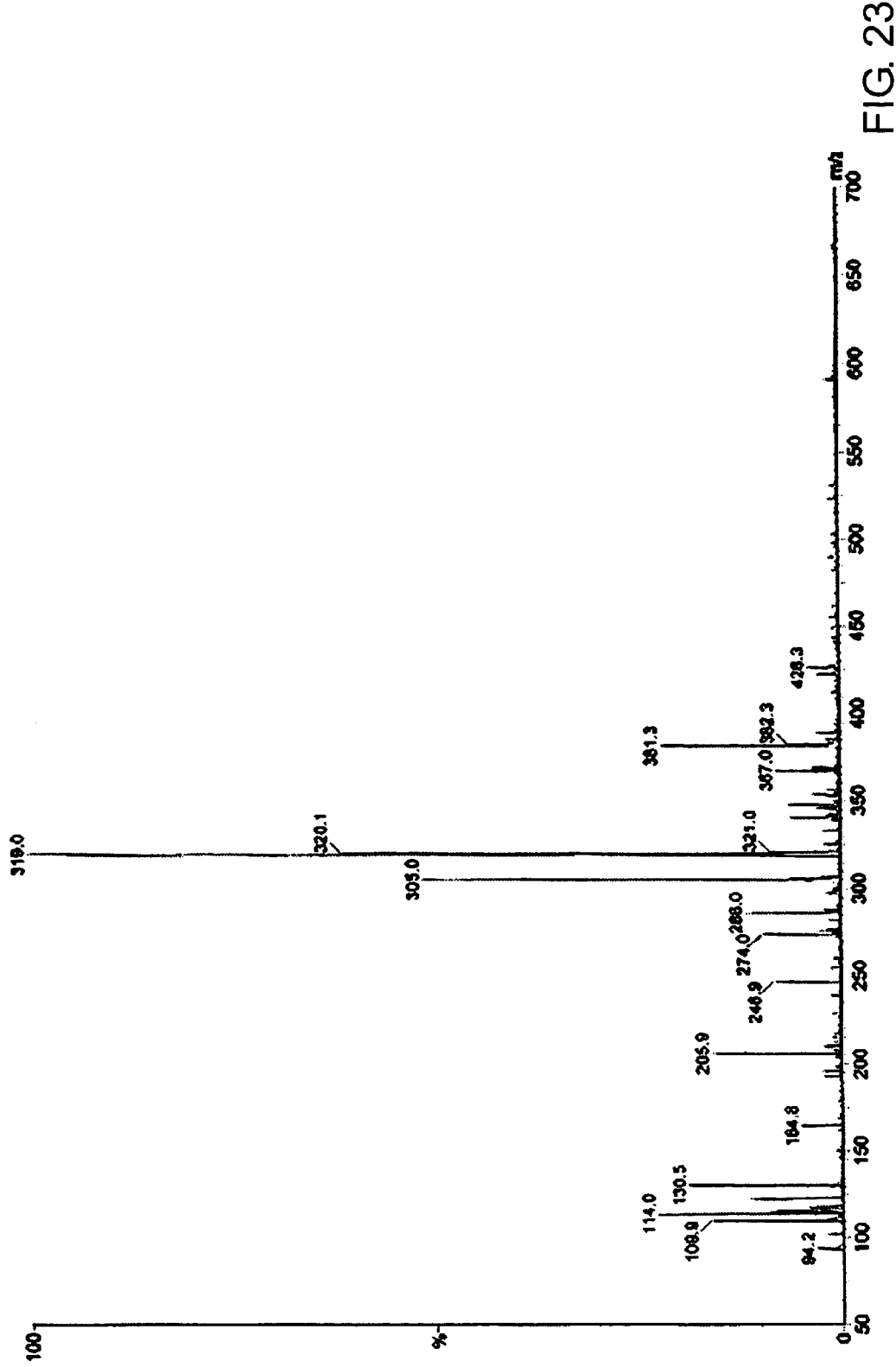
FIG. 23 depicts a positive ion electrospray mass spectrum of compound 2.20.
Figure 24:
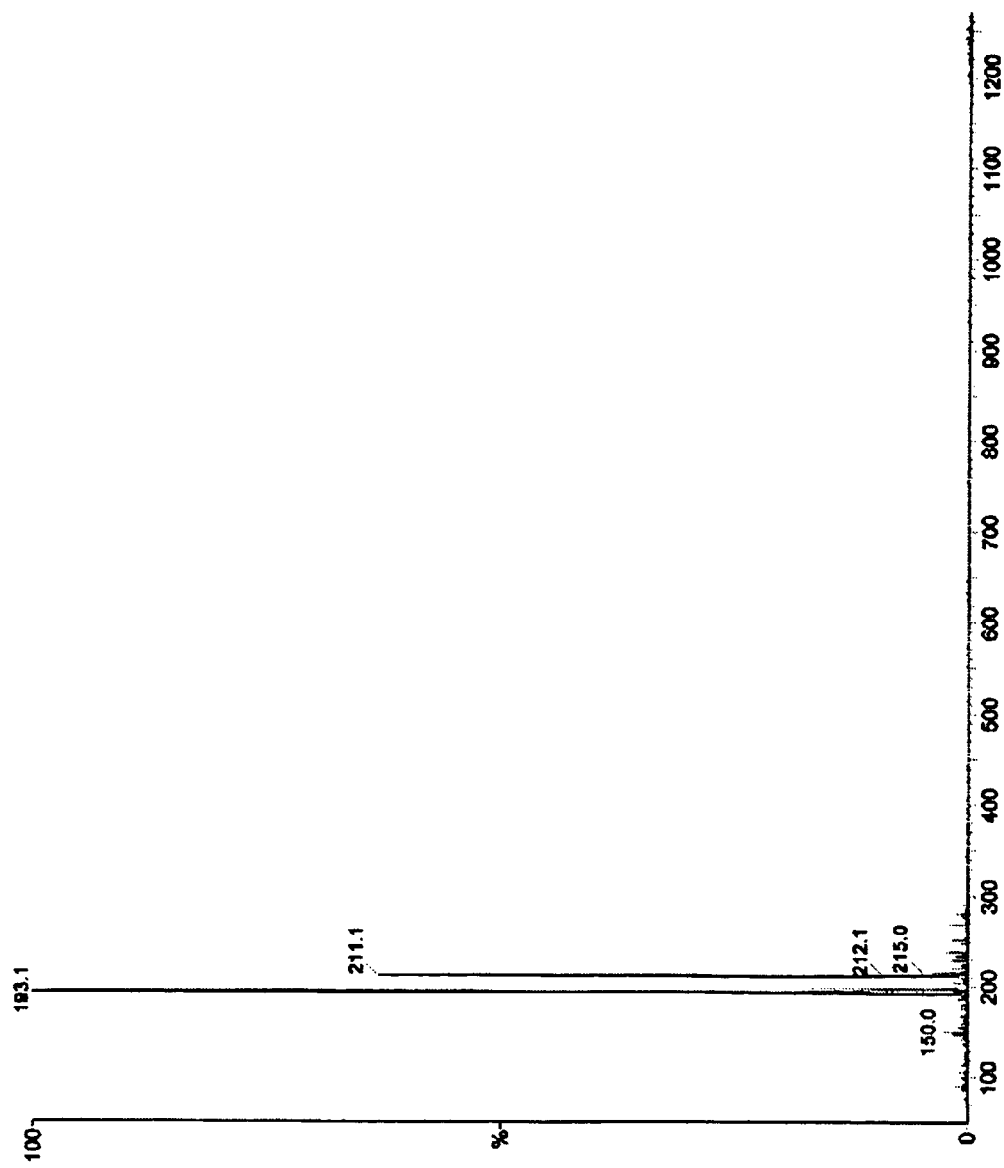
FIG. 24 depicts a positive ion electrospray mass spectrum of 3-fluorobenzamide.

An excess of iodine was added to a small quantity (2.37 µmol) of 2.21 and the reaction was stirred for 1 hour at room temperature. The reaction solution was quenched with sodium metabisulfite and placed on the rotary evaporator to remove methanol. The vial was washed with 1 mL of acetonitrile:water (50:50) and passed down a conditioned fluorous column. An additional 1 mL was used to rinse the vial and added to the column. The combined fractions were analysed through HPLC (FIG. 22) and electrospray mass spectrometry (FIG. 24).

The HPLC chromatogram for compound 2.20 shows three principle peaks eluting at 6.6, 16.6, and 18.9 minutes. The earliest peak was assigned as the solvent front, while the later eluting peaks were presumably the protonated and deprotonated states of 2.20, respectively. The positive ion electrospray mass spectrum of compound 2.20 showed a peak at m/z=319.0 [M+H]⁺. The purity of the 2.20 was again confirmed, as the negative ion mode showed no peak corresponding at m/z=247 [M-H]⁻, which would be present had unreacted 2.2 existed.

The cold fluorination of 2.21 was undertaken in a similar manner employed for 2.2. Preliminary results from the electrospray mass spectrum reveal the product peak m/z=211 [M+H]$^+$ (FIG. 24). The negative ion mode did not reveal any of the possible impurity, 3-fluorobenzoic acid, at m/z=139 (M−H)$^−$.

Summary

These initial cold experiments clearly indicate the potential to label 2.21 with $^{18}$F[F$_2$] and Na$^{125}$I, following the method used to label 2.2. Success would provide a facile route to radiolabelled benzamides for both SPECT and PET, and thereby increase their clinical utility. The development of a coupling procedure will allow us to prepare a diverse array of benzamides and related compounds for future radiolabelling.

Synthesis of Benzylamine and Derivatives

With the success attained at producing labelled benzoic acid and derivatives, we sought to expand the fluorous synthesis method to benzylamines and related derivatives.

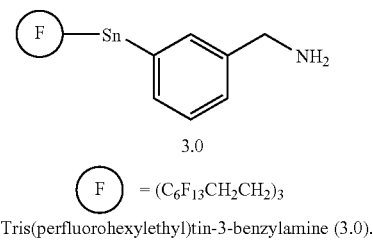

3.0

$\boxed{F}$ = (C$_6$F$_{13}$CH$_2$CH$_2$)$_3$

Tris(perfluorohexylethyl)tin-3-benzylamine (3.0).

This would provide a complementary nucleophilic derivative to the electrophilic halobenzoic acids. In addition it would expand the potential variety of compounds which could be coupled to the fluorous "tag" and then radiolabelled.

Derivatives of benzylamine have been used to label biomolecules,[28] and are precursors to the synthesis of [$^{131}$I] and [$^{123}$I] meta-iodobenzylguanidine (MIBG),[29] which is a valuable but synthetically challenging radiopharmaceutical.

Synthesis of Fluorous "tagged" benzylamine (3.0)

There are scarce examples in the literature describing the synthesis and/or labelling of trialkyltin bound benzylamine. Vaidyanathan, G et al. synthesised 3-(tri-n-butylstannyl) benzylamine in a 30% yield using n-BuLi, 3-bromobenzylamine, and a two-fold excess of tributyltin-chloride.[30] This approach was not considered for the synthesis of 3.0, due to the poor yield obtained and the generation of a large excess of fluorous by-products. Rather, a method reported by Hunter et al for the preparation of a polymer bound 3-benzylamine was adapted for the synthesis of 3.0.[31]

Hunter's method utilised the precursor, 3.1, an azadisilolidine protected derivative of 3-bromobenzylamine. This silicon-based protecting group is stable to n-BuLi, allowing for the synthesis of the corresponding monolithium salt, 3.2.

Synthesis of 3.1 entailed the reaction of 3-bromobenzylamine in triethylamine with 1,1,4,4-tetramethyl-1,4-dichlorosilethylene at room temperature for 1.5 hours (Scheme 14). Pouring the crude solution into aqueous sodium dihydrogen phosphate, followed by distillation of the crude organic extract, provided the product in moderate yield (64%). The $^1$H NMR of compound 3.1 revealed three singlets at 0.00 ppm (12H), 0.78 ppm (4H), and 4.06 ppm (2H), in addition to the aromatic peaks appearing at 7.20-7.48 ppm (4H). The $^{13}$C NMR of 3.1 had resonances at −0.26 ppm, 8.01 ppm, 45.59 ppm, 122.15 ppm, 126.10 ppm, 129.35 ppm, 129.53 ppm, 130.69 ppm, and 146.01 ppm. The electron impact mass spectrum of 3.1 gave a peak at m/z=312. These spectra are consistent with data reported in the literature.[4,32]

Scheme 14.
Precursor synthesis: silicon protected 3-bromobenzylamine (3.1).

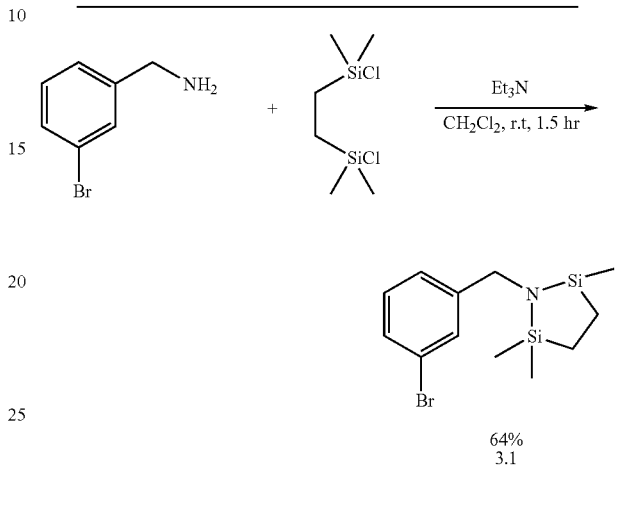

The synthesis of 3.3 (Scheme 15) involved reaction of 3.1 with n-BuLi in THF at −78° C. for a period of 35 minutes to generate 3.2. Compound 2.3 in THF was then added to 3.2 dropwise. The reaction was kept at −78° C. for 2 hours, where upon FC-72® was added and the mixture stirred for 10 minutes. The reaction was subsequently quenched through the addition of methanol (30 mL). Following the addition of methanol, the reaction was extracted with FC-72®, water, and dichloromethane. The FC-72® was removed on the rotary evaporator, providing 3.3 in 89% yield.

Scheme 15.
Synthesis of azadisilolidine protected perfluorotin -3-benzylamine (3.3).

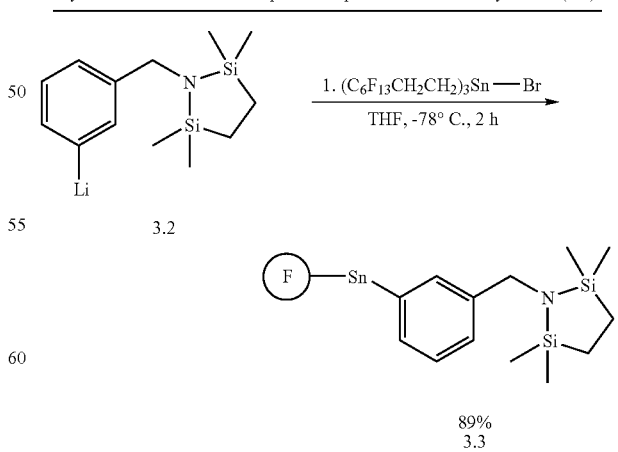

Hydrolysis of 3.3 (Scheme 16) involved stirring the compound overnight in methanol with sufficient 1 M HCl to give a pH≈3. The product was extracted into FC-72®, and concentrated to give 3.0 as a light yellow oil in 97% yield.

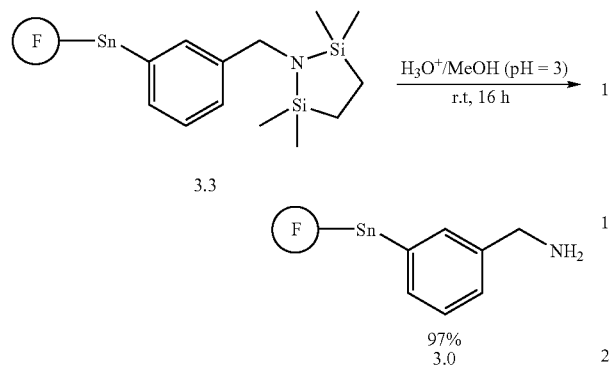

Scheme 16.
Hydrolysis of the silicon protecting group to generate 3.0.

Figure 25:
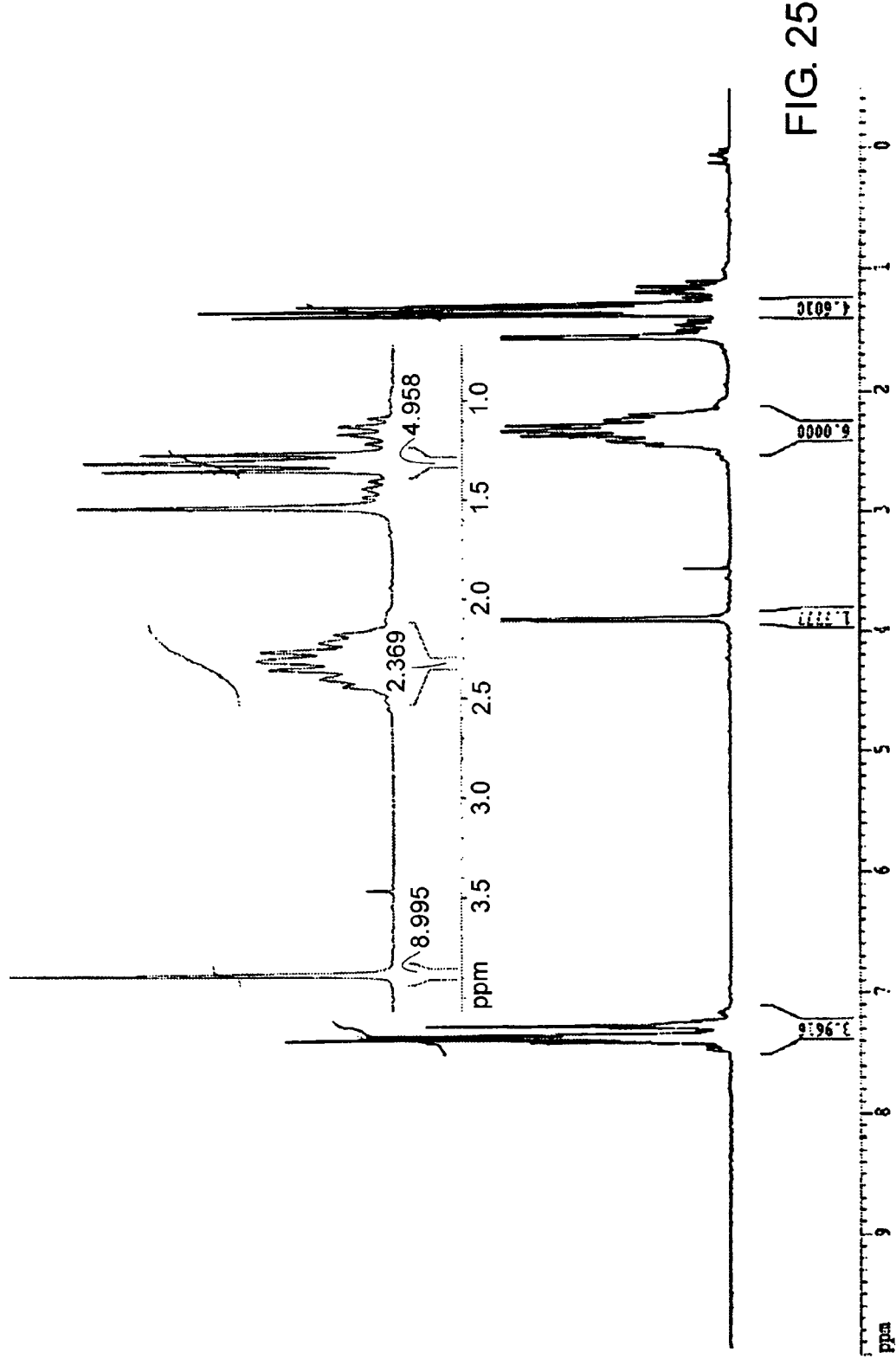
FIG. 25 depicts an $^1$H NMR [CDCl$_3$, 200 MHz] of compound 3.0.
Figure 26:
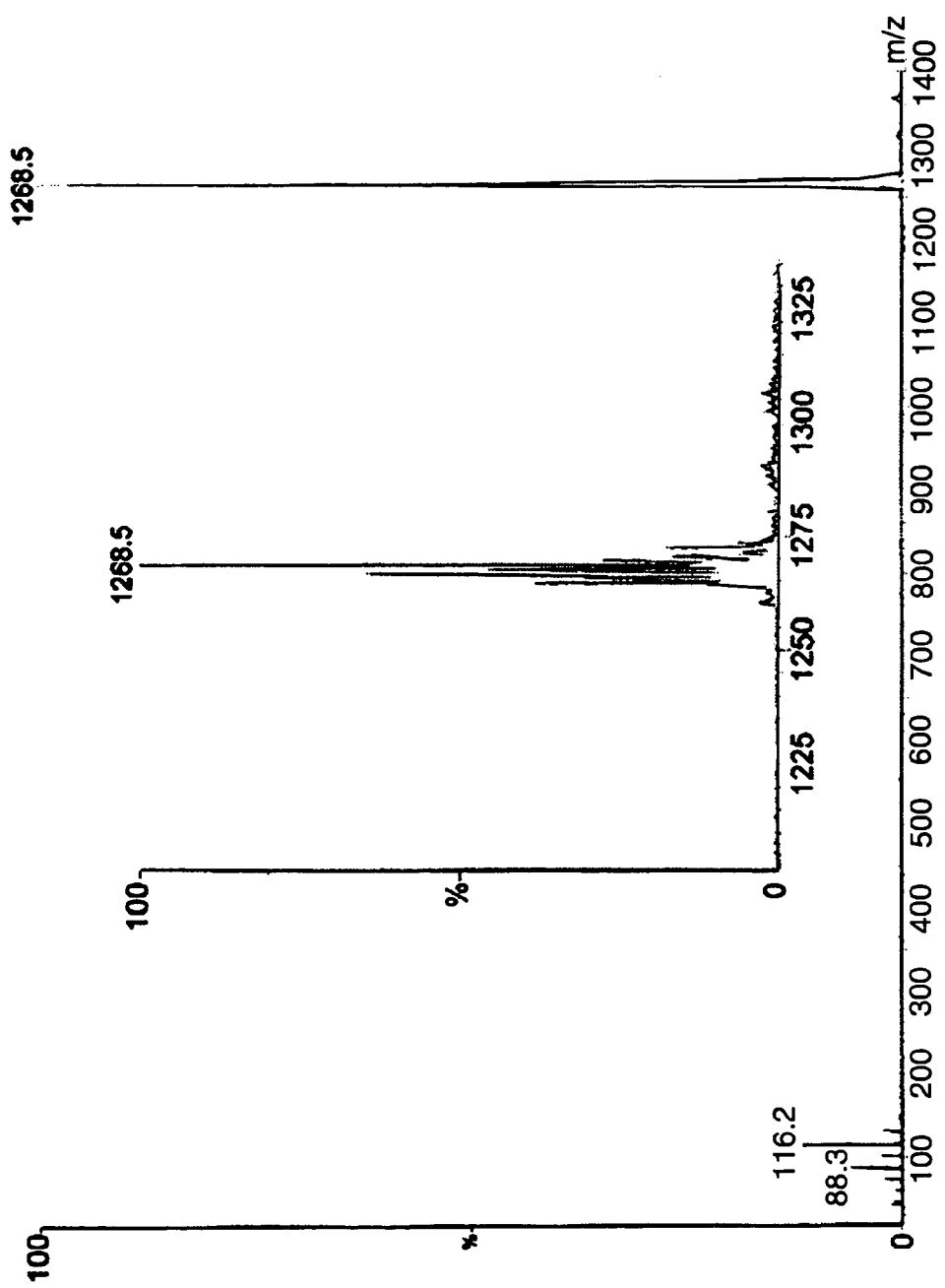
FIG. 26 depicts a positive ion electrospray mass spectrum of compound 3.0.

The $^1$H NMR of compound 3.0 (FIG. 25) showed a triplet at 1.31 ppm (6H) with Sn satellites ($^2J_{Sn,H}$=54.2 Hz), a multiplet at 2.31 ppm (6H), a singlet at 3.88 ppm, and aromatic peaks from 7.22-7.46 ppm. Trace amounts of the silicon protecting group can be seen in the baseline from 0.1-0.2 ppm. The $^{13}$C NMR showed a peak at −1.37 ppm ($^1J_{Sn,C}$=347 Hz), 27.94 ppm (t, $^1J_{F,C}$=23.4 Hz), and 46.62 ppm. The multiplets corresponding to carbon atoms bonded to fluorine were seen from 106.17-121.17 ppm, and the peaks associated with the aromatic region have yet to be definitively assigned. The positive ion electrospray mass spectrum of compound 3.0 (FIG. 26) shows a single peak at m/z=1268.5 [M+H]$^+$. The IR showed strong absorbances corresponding to C—H stretches at 2850 and 2955 cm$^{-1}$, and for the primary amine at 3354 cm$^1$. These results are all consistent with formation of the desired product.

The quantitative conversion of the stannylbromide precursor (2.3) to 3.3 proved extremely difficult. Early on it was appreciated that the azadisilolidine protected 3-bromobenzylamine (3.1) was not particularly stable. Synthesis and purification of 3.1 had to be immediately followed by reaction with n-BuLi to generate 3.2. If these measures were not taken, incomplete conversion of 2.3 would result.

Hunter and coworkers reported that reaction of 3.2 with the chlorostannane polymer for 7 hours at −78° C., followed by stirring at room temperature for 2 hours, resulted in quantitative functionalization of Sn—Cl bonds.$^4$ In contrast with these results, it was found that under similar reaction conditions only 50-67% of Sn—Br sites were converted to product (3.3). Through extensive trials it was appreciated that the product was extremely prone to decomposition if the reaction solution was allowed to warm to room temperature. The complete conversion of 2.3 to 3.3, therefore, could only be facilitated if the reaction was kept at −78° C., prior to immediate extraction into FC-72® and quenching with methanol.

Synthesis of Iodobenzyamine

Iododinolysis of 3.0 was carried out in order to further characterise the product bound to the fluorous tag and to ensure its purity (Scheme 17). Compound 3.0 was reacted with an excess of iodine in acetonitrile overnight, followed by quenching with sodium metabisulfite. The solution was diluted with water and passed down a conditioned fluorous column with an acetonitrile:water eluent (1:1). Aliquots (3×5 mL) were collected and the products characterised using HPLC and mass spectrum.

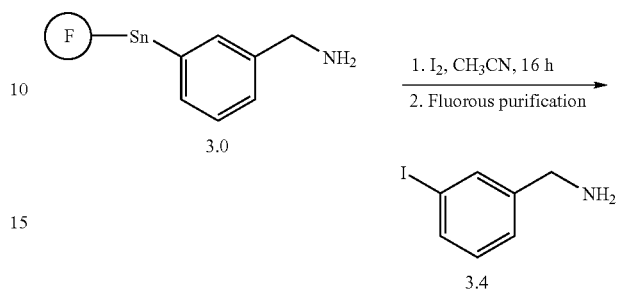

Scheme 17.
Iododestannylation of 3.0.

Figure 27:
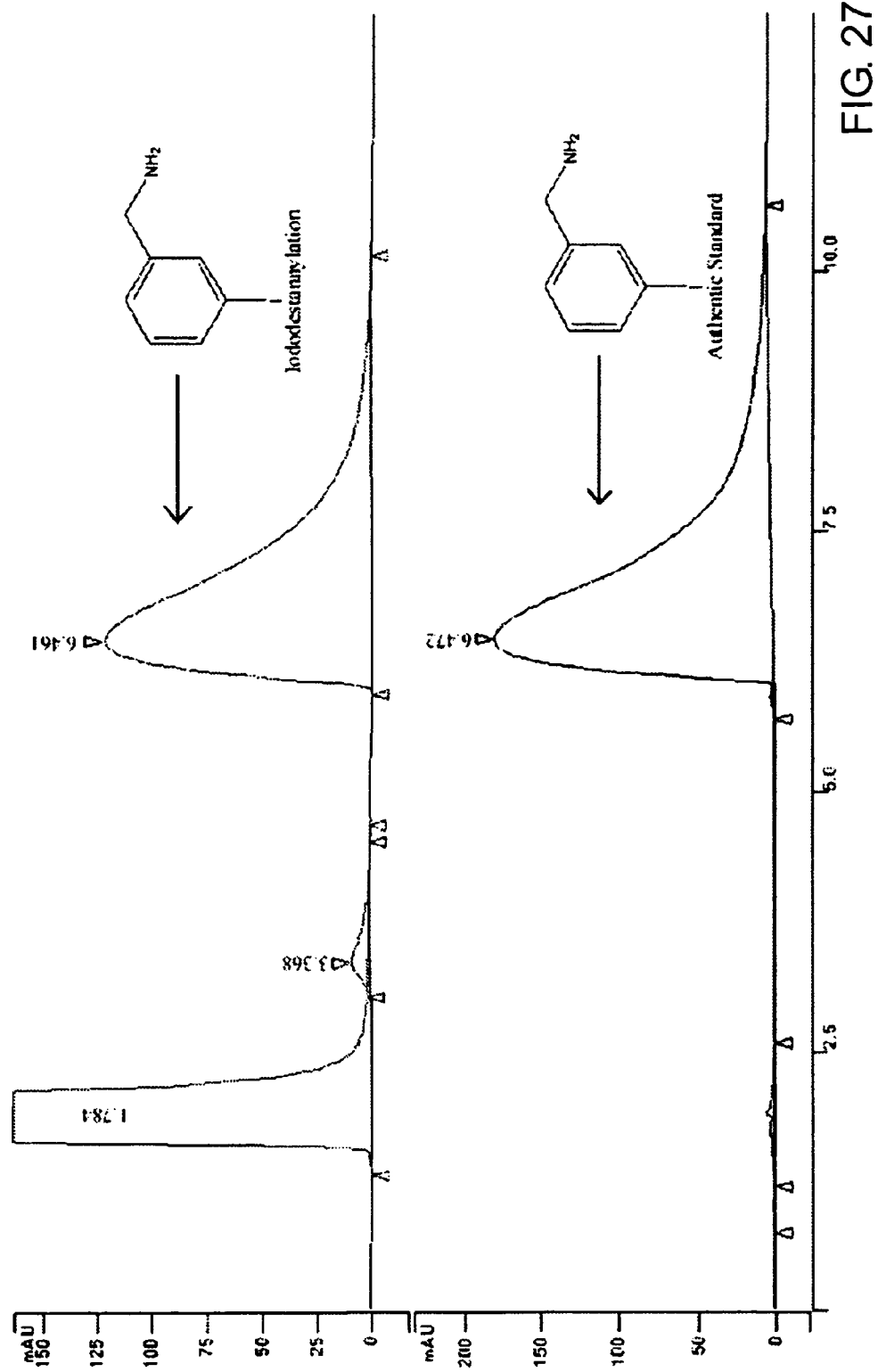
FIG. 27 depicts an HPLC chromatogram of authentic standard (lower) and 3.4 (upper).
Figure 28:
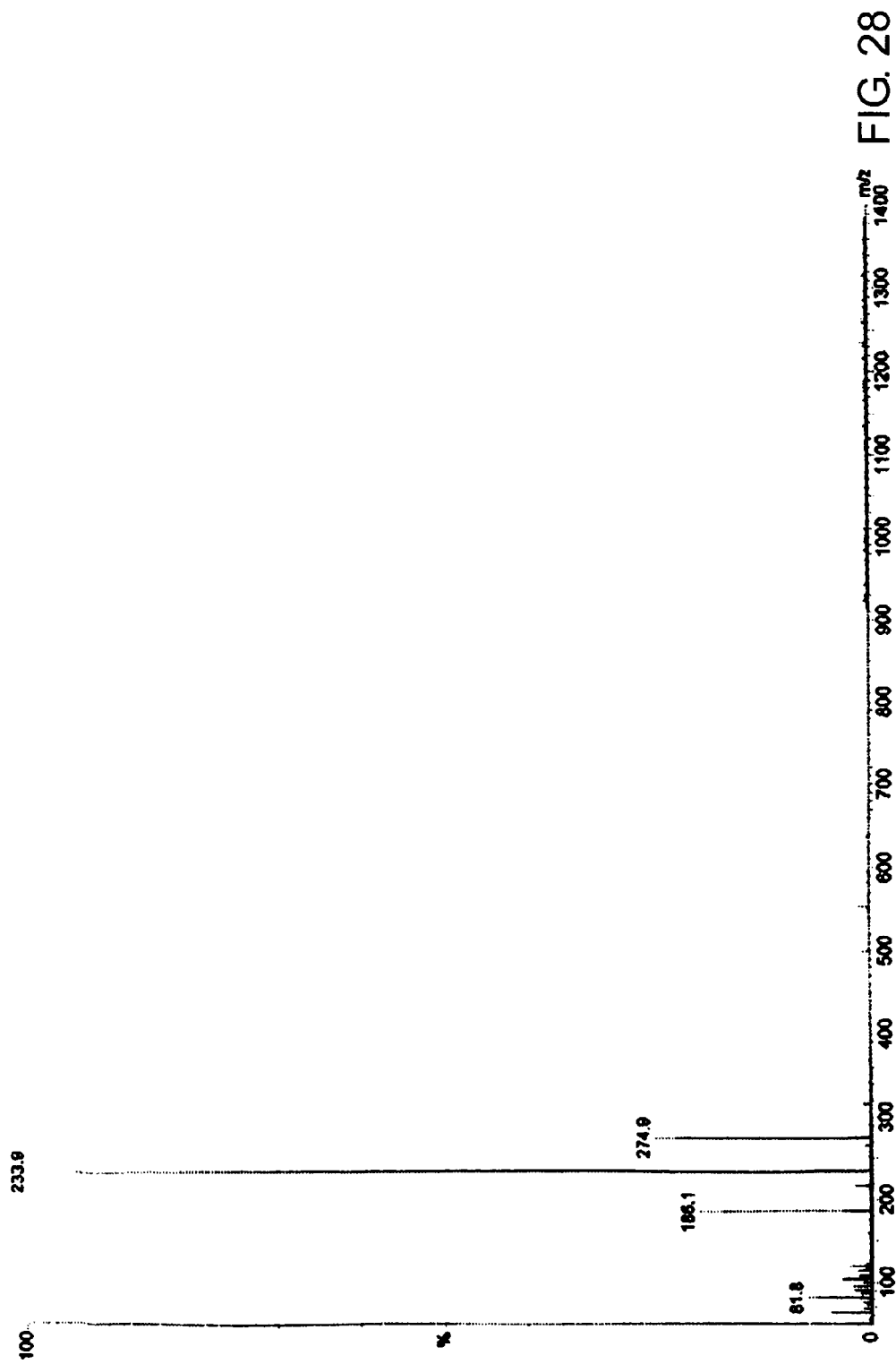
FIG. 28 depicts a positive ion electrospray mass spectrum of purified 3.4.

The HPLC chromatogram (FIG. 27) of the purified solution (3.4) generated two principle peaks at 1.78 and 6.46 minutes, corresponding to the solvent front and 3-iodobenzylamine, respectively. An authentic standard of 3-iodobenzylamine under similar elution conditions produced a peak at 6.47 minutes. Positive ion electrospray (FIG. 28) mass spectrum of the reaction solution produced a single peak at m/z=233.9 [M+H]$^+$, with no evidence of the fluorous impurity at approximately m/z>1200. These results are consistent with formation of 3.4.

Meta-iodobenzylguanidine

During the past two decades, radioiodinated MIBG (m-iodobenzylguanidine) has been used extensively in nuclear medicine.$^{33}$ It is used primarily for diagnostic scintigraphy and therapy of neural crest tumours such as phaeochromocytoma and neuroblastoma.$^{34}$ In addition, it is increasingly being used to assess the status of adrenergic nerves in the heart muscle.$^6$ The most widely employed synthesis method for production of [$^{123}$I] or [$^{131}$I] MIBG involves the Cu$^+$ catalyzed exchange process. Unfortunately, this method yields a low specific activity product (50 mCi/mg for [$^{123}$I]) necessitating an increased dose, which in turn results in poorer quality images.$^4$ Consequently, several routes to a no-carrier-added product have been investigated; however, none have found widespread application.$^{35}$ A fluorous strategy for the synthesis of MIBG may ameliorate the aforementioned synthetic limitations. Furthermore, if a convenient labelling method were available, there is substantial interest in generating a positron emitting MIGB-related radiopharmaceutical. For example, Zalutsky et al. synthesised meta-[$^{18}$F]fluorobenzylguanidine and para-[$^{18}$F]fluorobenzylguanidine in three steps with a fluoro for nitro exchange reaction. They reported lower than desirable radiochemical yields of 10-15% ([$^{18}$F]MFBG) and 50-55% [$^{18}$F]PFBG, and difficulty removing impurities.$^{36}$ The next section describes the development of a fluorous strategy for the preparation of [*I]MIBG and [$^{18}$F]MFBG.

Synthesis of tris(perfluorohexylethyl)tin-3-benzylguanidinium (3.5)

In order to produce tris(perfluorohexylethyl)tin-3-benzylguanidine, 3.5, several synthetic routes were attempted. The first approach, approach A (Scheme 18), applied the method developed by Wieland et al. for synthesis of 3.5.$^{37}$ Wieland's method involves the reaction of m-iodobenzylamine with cyanimide at 100° C. for 4 hours. Unfortunately, the synthesis of 3.5 through various adapted procedures would only yield trace amounts of the product, as indicated by electrospray mass spectrometry.

Scheme 18.
Attempted synthesis of 3.5 using cyanimide

Approach A)

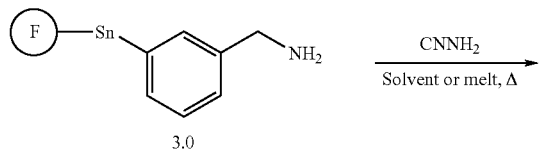

3.0

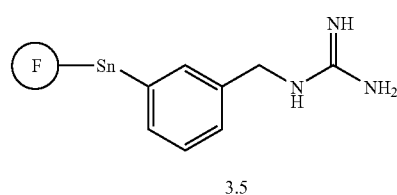

3.5

The failure of this reaction method to generate 3.5 is likely a result of the precursor 3.0 not being protonated. Although hydrolysis of the silicon-protecting group to generate 3.0 occurred at a pH of 3, the expected benzylammonium chloride was not formed. The benzylammonium chloride is necessary in order to activate cyanimide to nucleophilic attack (Scheme 19).

Scheme 19.
Mechanism of guanidine formation with cyanimide

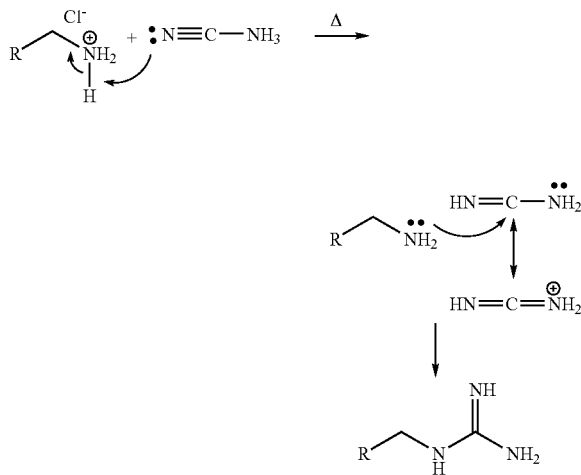

Any further attempts at protonating 3.0 resulted in protodestannylation. Similarly, the addition of catalytic amounts of HCl (0.05 eq) resulted in protodestannylation under the reaction conditions (54° C.). These results mirror the findings of Vaidyanathan et al., who were unable to convert 3-(tri-n-butylstannyl)benzylamine to the guanidine.[8] Rather, they were forced to synthesize [$^{131}$I]MIBG from radioiododestannylation of (trialkylstannyl)benzylamine, followed by its subsequent reaction with cyanimide.

Approach B entailed the adaptation of research by Jursic et al. for their preparation of N-formamidinylamino acids.[38] Here, the reaction of formamidinesulfinic acid [HN=C(NH$_2$)SO$_2$H] with a substituted amino acid (D,L-phenylalanine) in aqueous sodium hydroxide leads to the generation of D,L-N-formamidinephenylalanine (Scheme 20).

Scheme 20.
Attempted synthesis of 3.5 using foramidinesulfinic acid

Approach B)

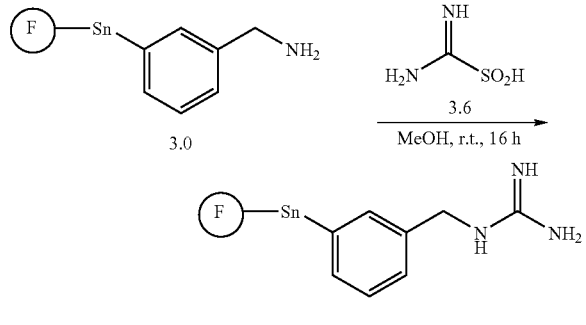

Figure 29:
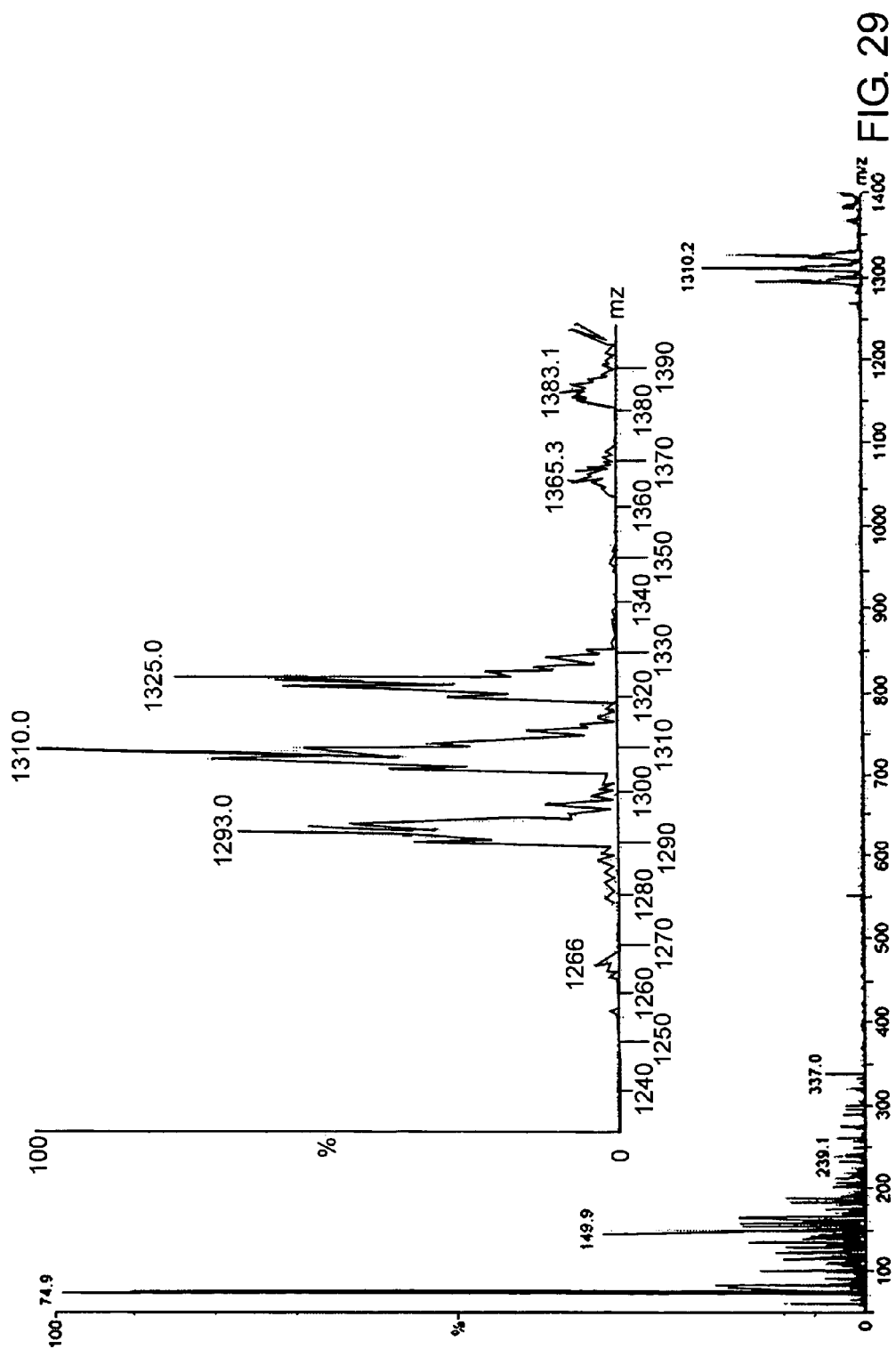
FIG. 29 depicts a positive ion electrospray mass spectrum of compound 3.5 (Appro.B).

Application of this approach towards 3.5 was found to be most successful when 3.0 was stirred with 2.0 equivalents of foramidinesulfinic acid in methanol overnight at room temperature. The methanol was removed on the rotary evaporator, prior to a triphasic extraction. The white viscous oil obtained following removal of FC-72® was heated in chloroform and subsequently decanted to remove any unreacted 3.0. The product, a viscous white oil, was obtained in good yield (86%). The positive ion electrospray mass spectrum of compound 3.5 (synthesised using foramidinesulfinic acid) showed a peak at m/z=1310.2 [M+H]$^+$, in addition to peaks at m/z=1325.1 and m/z=1293.1 (FIG. 29). The $^1$H NMR and $^{13}$C NMR for compound 3.5 could not be acquired, as no suitable solvent could be found.

Compound 3.5 was treated with cold I$_2$ and F$_2$, and a similar peak pattern in the elctrospray mass spectrum was found for the cleaved products. The peak associated with the product was typically the most intense, flanked on either side with a peak of +/−15 mass units. As the resulting peak pattern could not be rationalized, other routes to the synthesis of 3.5 were investigated.

3.3.2 Approach C

Approach C involved adaptation of the research by Mosher et al., who converted several primary amines to the corresponding guanidines.[39] The conversions were accomplished by reacting aminoimino-methanesulfonic acid with a primary amine for two hours at room temperature to generate the corresponding guanidine in moderate yield (22-80%). This method appeared applicable for the synthesis of 3.5, as a free amine could be converted to the guanidine under mild conditions (pH=3.1).

Aminoiminomethanesulfonic acid (H$_2$N—C(=NH)SO$_3$H) (3.7) was synthesized in high yield through reaction of foramidinesulfinic acid (3.6) with peracetic acid, following the procedure of Mosher (Scheme 21).[12] The melting point of compound 3.7 was consistent with literature findings of 125-126° C.[12]

Scheme 21.
Synthesis of aminoiminomethansulfonic acid (3.7)

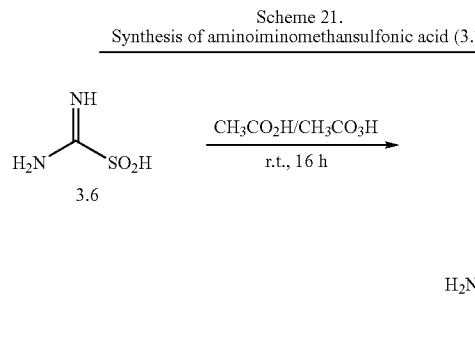

Compound 3.7 was first reacted with m-iodobenzylamine in order to assess the products formed and to obtain a standard sample of MIBG (Scheme 22). Equivalent molar quantities of 3.7 and 3.8 were combined in methanol and refluxed overnight. The resulting product (3.9) was characterized without further purification. The $^1$H NMR showed a singlet at 4.22 ppm, and aromatic peaks between 6.90-7.56 ppm. The $^{13}$C NMR showed a peak at 48.9 ppm, 99.3 ppm, 131.6 ppm, 135.7 ppm, 141.0 ppm, 141.9 ppm, 144.3 ppm, and 162.65 ppm. The positive ion electrospray mass spectrum showed a peak at m/z=276.1 [M+H]+corresponding to 3.9, and a extremely small peak at m/z=233.9 [M+H]+ corresponding to 3.8. The HPLC analysis of compound 3.9 generated only one principle peak at $t_R$=24.54 minutes (86% of total peak area). This data is consistent with literature reports, and confirms formation of the desired product.[40]

Scheme 22.
Synthesis of standard m-iodobenzylguanidine (3.9)

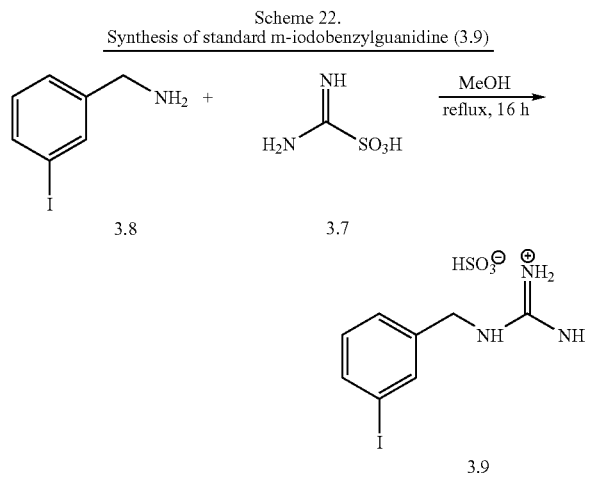

The synthesis of compound 3.9 using 3.7 prompted the application of this procedure toward the synthesis of 3.5 (Scheme 23, Approach C). Compound 3.0 was combined with 1.1 equivalents of 3.7 in methanol and refluxed overnight. Incomplete conversion occurred if the reaction was carried out at room temperature as suggested by Mosher et al.[12] Extraction of the crude reaction mixture into FC-72® from methanol generated the product as a milky white oil in acceptable yield (88%).

Scheme 23.
Successful synthesis of compound 3.5 following approach C.

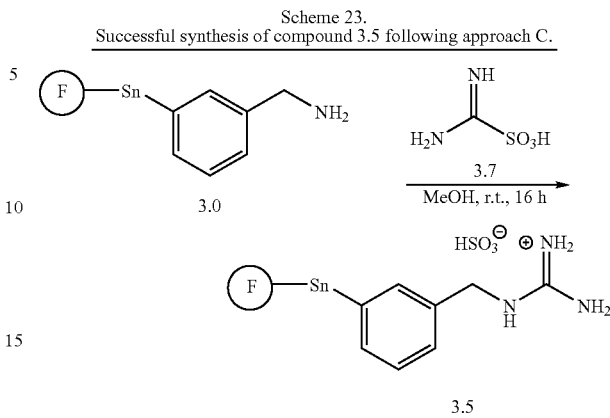

Figure 30:
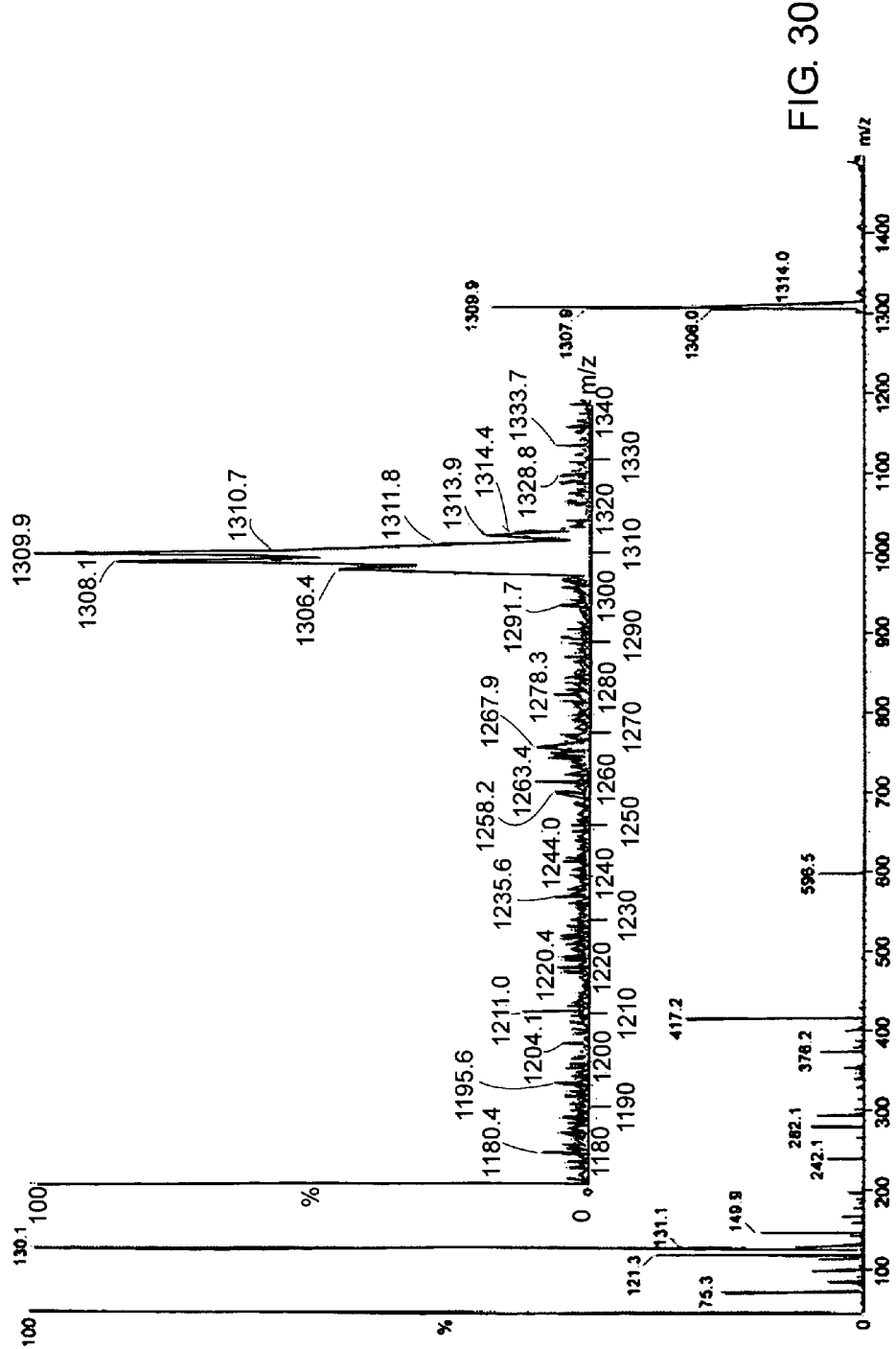
FIG. 30 depicts a positive ion electrospray mass spectrum of 3.5 via Approach C.

Positive ion electrospray mass spectrometry (FIG. 30) showed a single peak at m/z=1309.9 [M+H]+, which is consistent with the formation of 3.5. The electrospray spectrum did not show any peaks that were associated with the precursor (3.0), which had a m/z value of 1268, nor the peaks corresponding to m/z+/−15, which had been seen using approach B. Currently, resolved $^1$H NMR and $^{13}$C NMR spectra for compound 3.5 have not yet been obtained, a result of the compounds poor solubility.

Synthesis of Labelled MIBG (3.10)

The cold iodination of 3.5 was undertaken in order to assess the products and reaction conditions for eventual use of Na$^{125}$I (Scheme 24). A sample of 3.5 (3.90 μmol), synthesised through approach C, was dissolved in methanol. To the stirring solution was added NaI (4.6×10$^{-7}$ mmol), which was followed promptly by addition of the peracetic acid oxidant. The reaction was stirred for 2 hours and then quenched with 100 μL of a 10% sodium metabisulfite solution. Purification of the dilute reaction solution was not attempted, though it has been established that fluorous material can easily be removed from the cleavage products.

Scheme 24.
Cold labelling of MIBG with NaI (3.10).

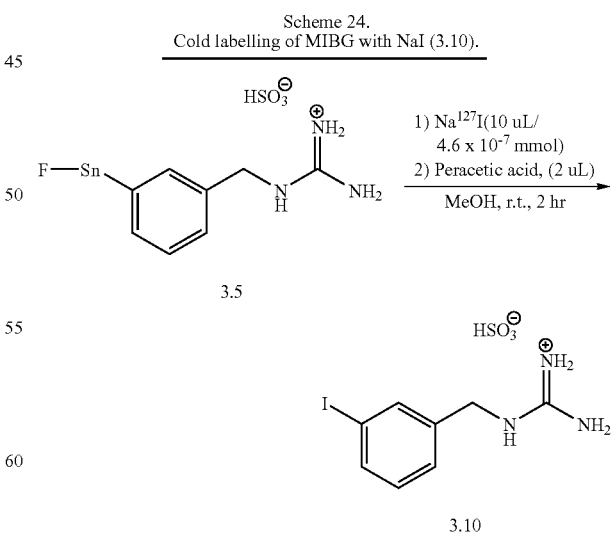

Figure 31:
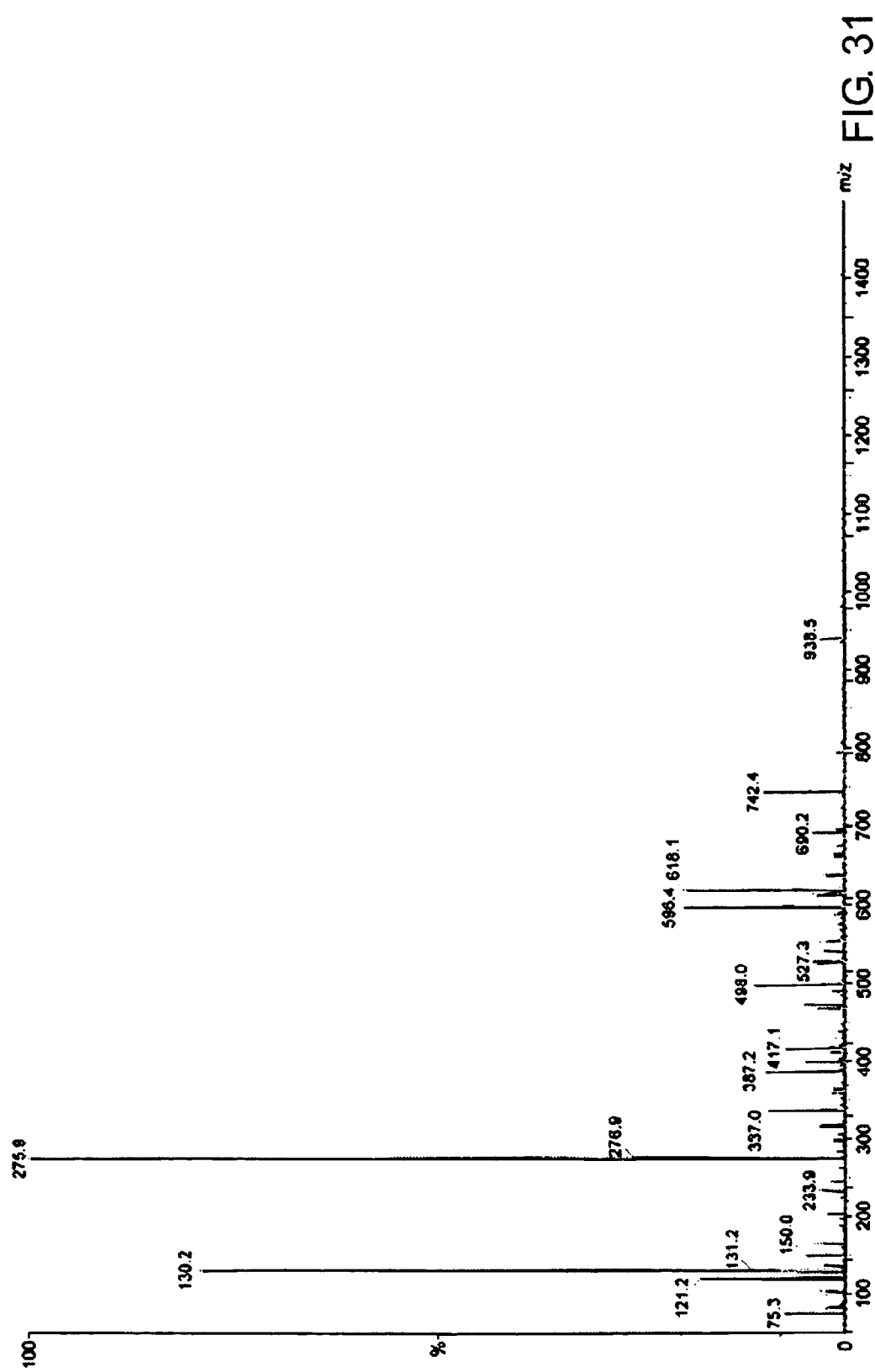
FIG. 31 depicts a positive ion electrospray mass spectrum of 3.10.
Figure 32:
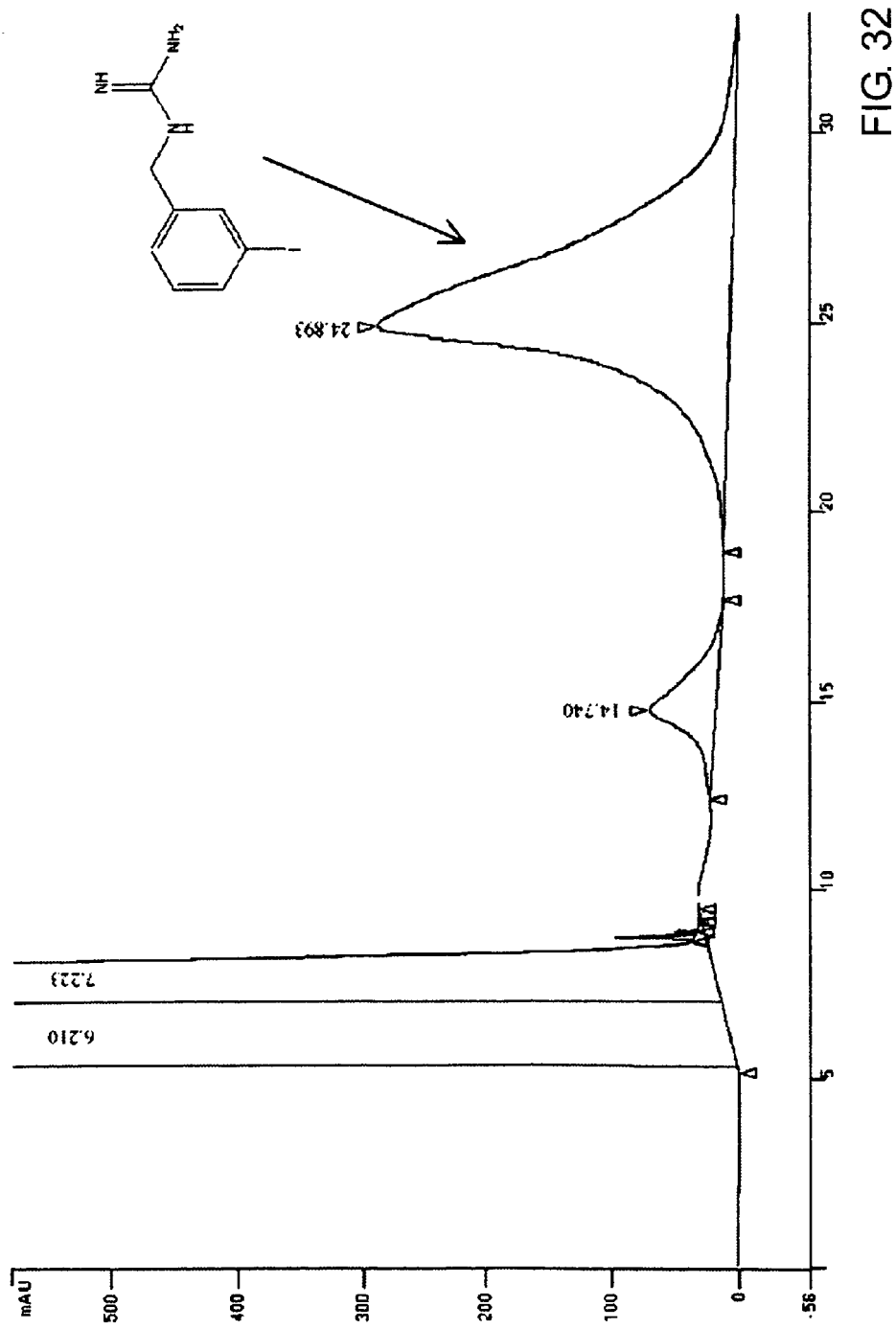
FIG. 32 depicts an HPLC chromatogram of 3.10.

The positive ion electrospray mass spectrum of compound 3.10 revealed a peak at m/z=275.9 [M+H]+which is consistent with the product (FIG. 31). HPLC a 100 μL aliquot of compound 3.10 showed peaks with retention times of 7.2, 14.7, and 24.9 minutes (FIG. 32). The peaks eluting at 7 minutes and 24.9 minutes were assigned to the solvent front and product 3.10, respectively. The standard preparation of MIBG eluted with a similar retention time of 24.5 minutes. The peak at 14.7 minutes accounted for <1% of total MIGB and the nature of the compound giving rise to the peak remains unknown.

Synthesis of MFBG (3.11)

The encouraging results for the iodine labelling of 3.5 prompted us to investigate the possibility of synthesising m-fluorobenzylguanidine (MFBG). The fluorodestannylation reaction for the synthesis of MFBG (3.11) is shown in Scheme 25. The cold fluorination reaction of compound 3.5 proceeded in a manner analogous to those of previous reactions (3-fluorobenzoic acid and 3-fluorobenzamide). To an FEP tube containing 3.5 dissolved in FC-72® at −93° C. was bubbled approximately 0.7 equivalents of $F_2$ (0.6% in Ne). Following the reaction, the FC-72® from the reaction along with methanol used to rinse the vessel were removed on rotary evaporator, prior to diluting with acetonitrile:water (1:1) and eluting down a conditioned fluorous column.

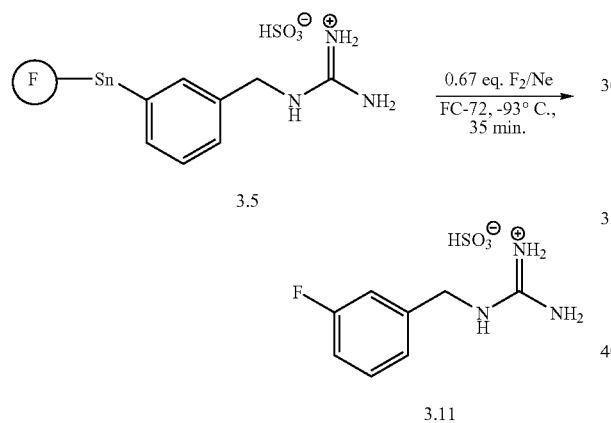

Scheme 25.
Synthesis of MFBG (3.11).

Figure 33:
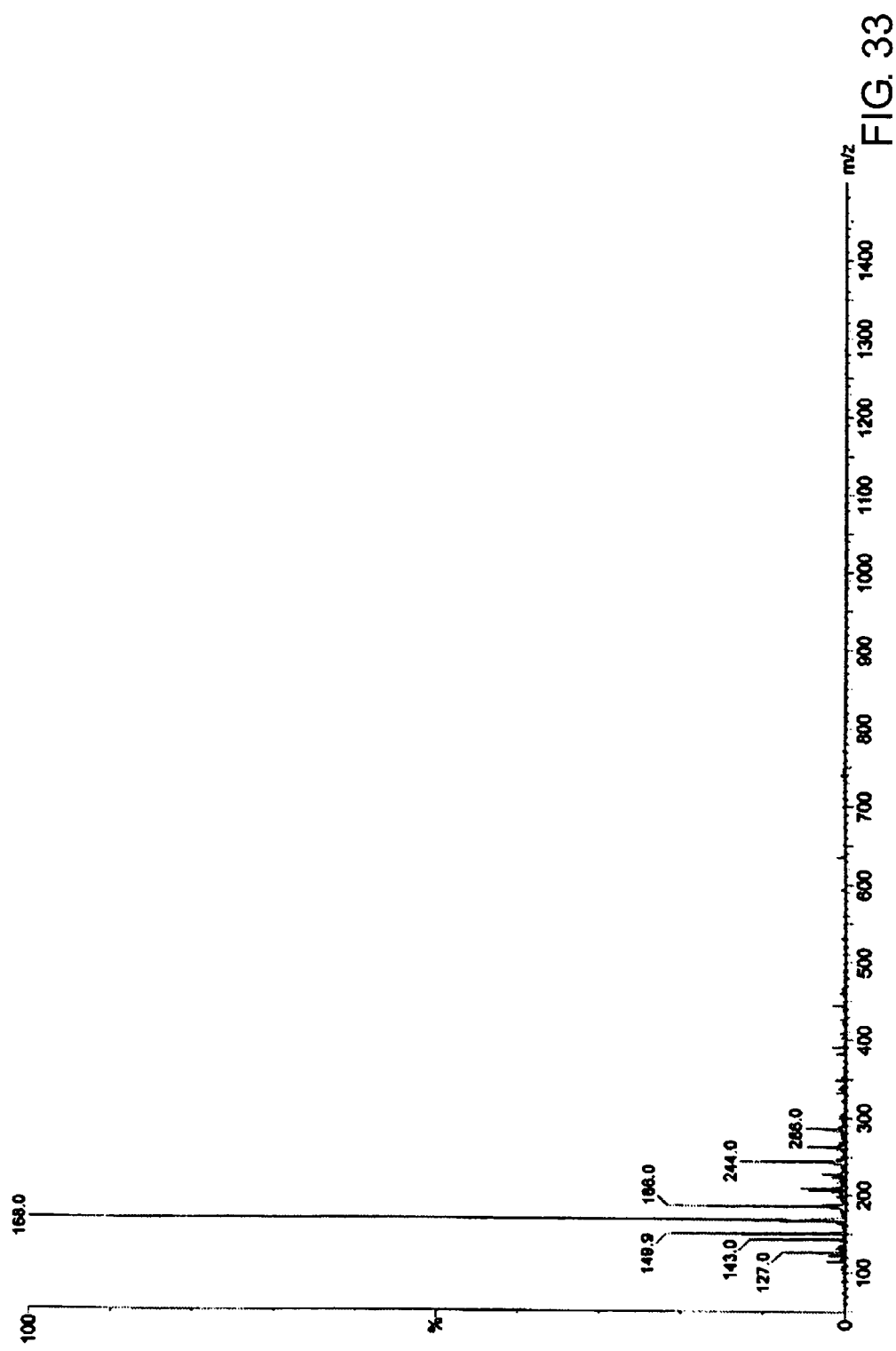
FIG. 33 depicts a positive ion electrospray mass spectrum of compound 3.11.

The positive ion electrospray mass spectrum for compound 3.11 showed a single peak at m/z=168.0 [M+H]+ (FIG. 33). The mass spectrum showed no evidence of any fluorous impurity at m/z>1000 or evidence of 3-fluorobenzylamine at m/z=126 [M+H]+.

Figure 34:
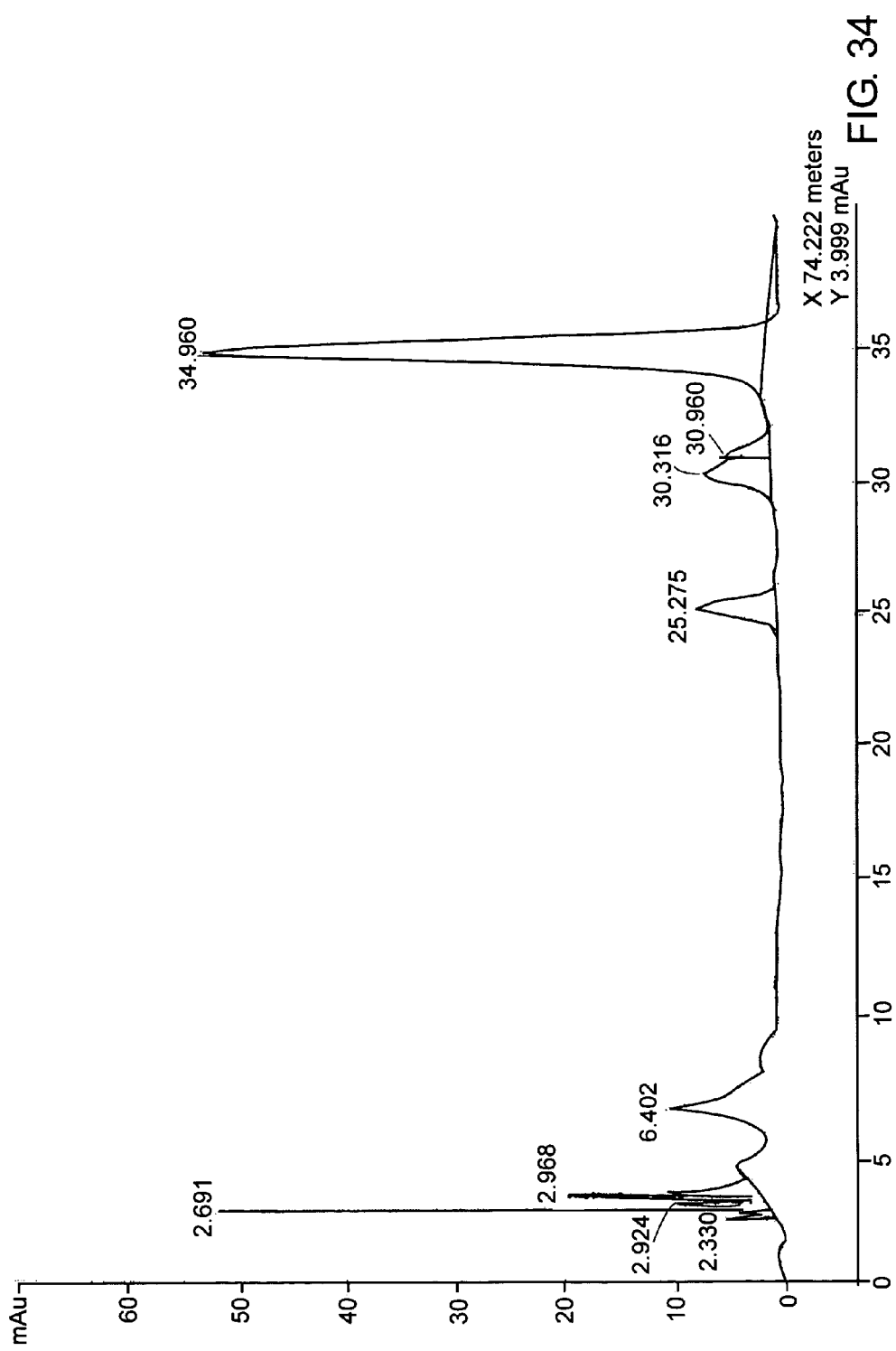
FIG. 34 depicts an HPLC chromatogram of MFBG (3.11).

The HPLC chromatogram of compound 3.11 contains peaks at the solvent front ($t_R$=2—6 min.) and peaks eluting at 25.3 min., 30.3 min., and 35.0 minutes (FIG. 34). There are no peaks corresponding to 3-fluorobenzylamine which has a retention time of 15.8 minutes under these elution conditions. The elution conditions are the same as those used for MIBG, and it is therefore surprising that the principle peak (61+%) eluting at 35 minutes is more highly retained than MIBG. The longer retention time might suggest a di-fluorinated or a bi-guanidinium species; however, peaks corresponding to these products are not found in the electrospray mass spectrum. Unfortunately, at the time of these experiments, an authentic standard of MFBG was not available to better interpret these results.

Figure 35:
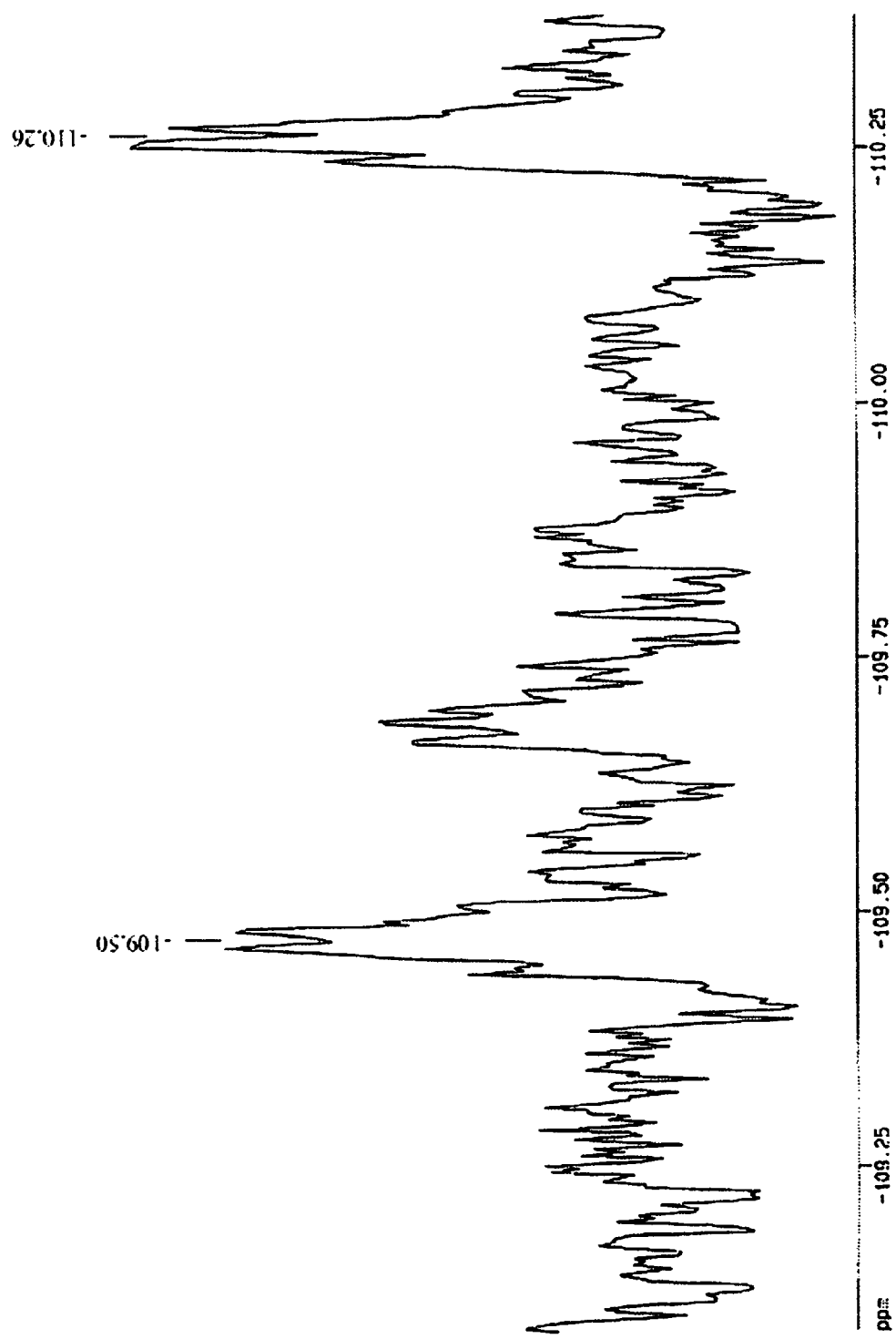
FIG. 35 depicts an $^{19}$F NMR [ACN:H$_2$O, 188 MHz] spectrum of compound 3.11.

The $^{19}$F NMR of compound 3.11 shows three peaks (FIG. 35). The two principle peaks are centred at −109.5 ppm and −110.3 ppm, with $^3J_{H,F}$ coupling of 9.2 Hz and 8.7 Hz respectively. These peak positions and coupling constants are consistent with a meta or para-fluorinated aryl compound. The smaller coupling constants initially suggest that a 1, 2 or 1,4 difluorinated species is not present. The varying peak positions, rather than being attributed to isomers, could be the results of varying protonation states, which has been shown to markedly affect fluorine shifts.[41] The poor resolution of the spectrum can be attributed to the dilute sample, obtained without further concentrating the eluent. Concentration of the sample on the lyophilizer was avoided as it appeared this resulted in loss of product on several occasions.

Coupling through tris(perfluorohexylethyl)tin-3-benzylamine

As mentioned in Chapter 2, short peptide sequences have been used to target radionuclides to specific receptors. For receptor specific agents of this type, it is important that all unreacted material is separated from the radiopharmaceutical. It would be advantageous therefore to develop the fluorous approach for labelling peptides. In this chapter preliminary steps towards these goals were taken. In particular, a method of coupling the carboxylic acid terminus of a model oligopeptide to the fluorous "tagged" benzylamine was developed.

The chemotactic peptide N-formyl-Met-Leu-Phe-Gly, 3.12 is a bacterial product which binds to polymorphonuclear leucocytes and mononuclear macrophages. Fischman et al. have shown that radiolabelled derivatives of this peptide are effective for imaging sites of abscesses and inflammation.[42] The severe toxicity of chemotactic peptides in higher doses has hampered their clinical application; consequently it is essential that any unlabelled material be removed.

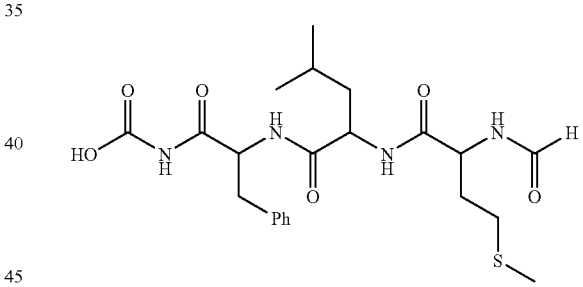

3.12
N-formyl-Met-Leu-Phe-Gly or GFLM(f) (3.12)

Synthesis of tris(perfluorohexylethyl)-3-benzylamine-GFLM(f) (3.13)

The coupling strategy developed for the synthesis of fluorous "tagged" benzamide should be applicable to the current objective. In this case, however, the peptides carboxylic acid terminus will be activated (HBTU) for nucleophilic attack by benzylamine (3.0).

Synthesis of compound 3.13 (Scheme 26) entailed combining 3.0 and 3.12 in DMF, followed by addition of the acylating reagent (HBTU) and base. The reaction was stirred at room temperature overnight, diluted with water, and extracted into FC-72®. The FC-72® layer was found to contain only a small quantity of product 3.13 along with unreacted 3.0, as determined by electrospray mass spectrometry. The majority of 3.13 was in fact partitioned between FC-72® and DMF/H$_2$O. Evidently, the polar nature of the peptide is significant enough to make the product no longer completely soluble in the fluorous solvent, while the fluorous "tag" prevents the peptide from dissolving in the H₂O phase. This result is somewhat favourable, as it permits facile purification of the fluorophobic product (3.13) from any unreacted fluorophilic precursor (3.0) by collecting the interfacial emulsion.

Isolating the resulting white emulsion was followed by re-extraction from FC-72® to remove any unreacted 3.0. The yield (33%) of the resulting thick, gummy, white solid was compromised so as to ensure the isolation of a pure sample.

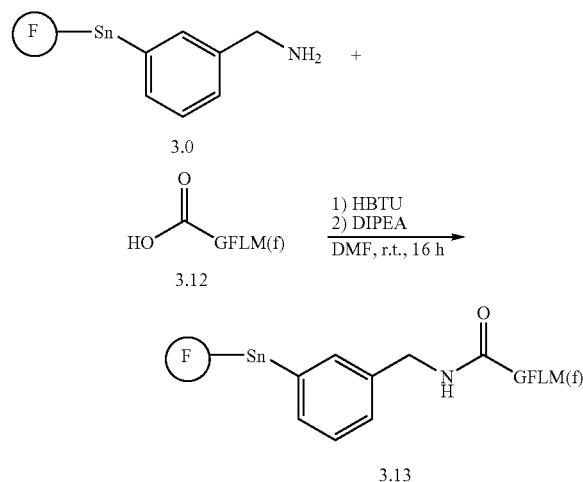

Scheme 26.
Coupling compound 3.0 to GFLM(f).

Figure 36:
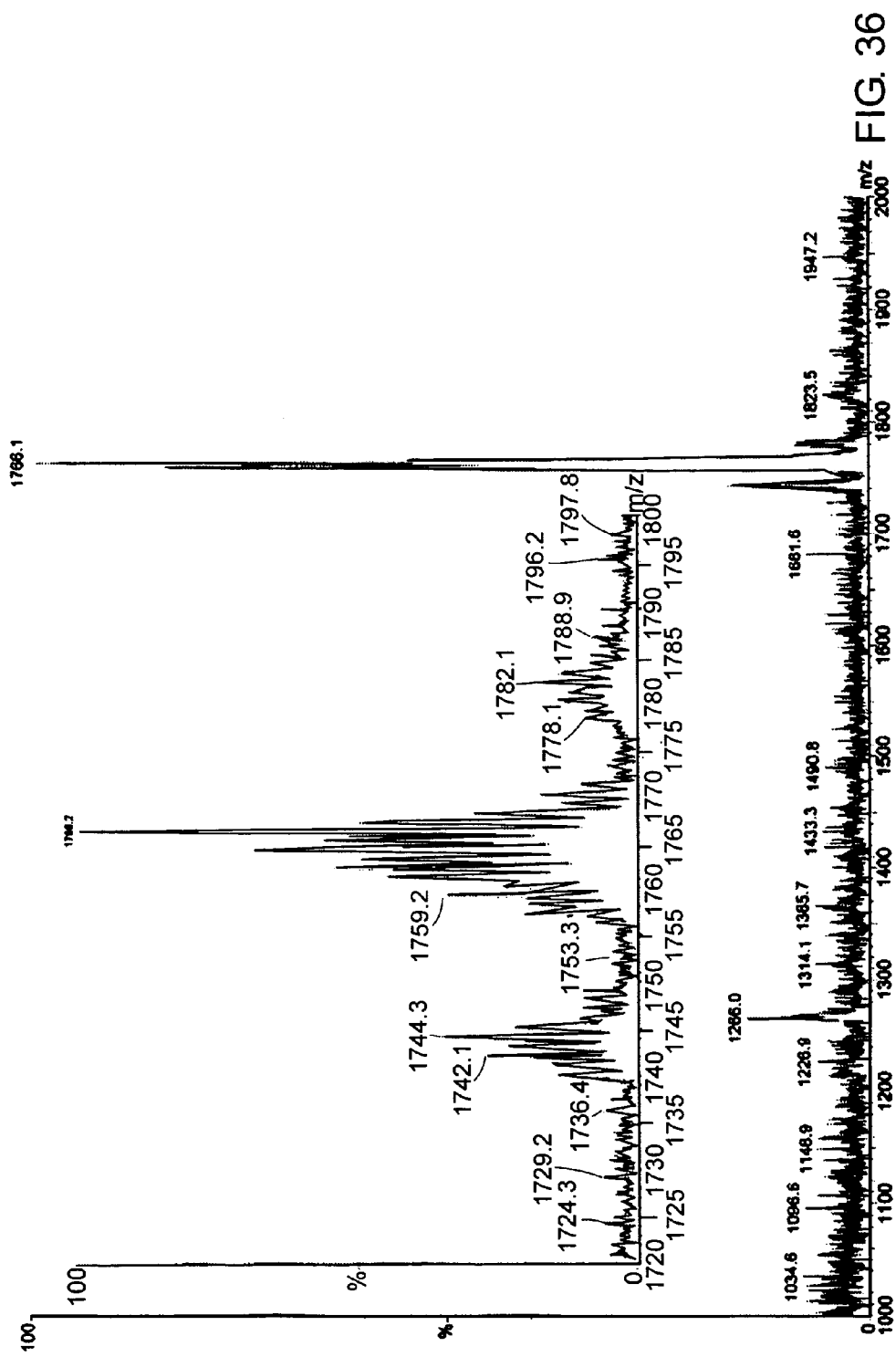
FIG. 36 depicts a positive ion electrospray mass spectrum of compound 3.13.

FIG. 36 shows the positive ion electrospray mass spectrum of compound 3.13. The peak pattern is characteristic of the product with m/z=1744 [M+H]⁺, m/z=1761 [M+NH₄]⁺, and m/z=1766 [M+Na]⁺. The spectrum revealed no peak at m/z=1268 corresponding to the precursor 3.0.

Iodine Labelling of Compound 3.13.

Figure 37:
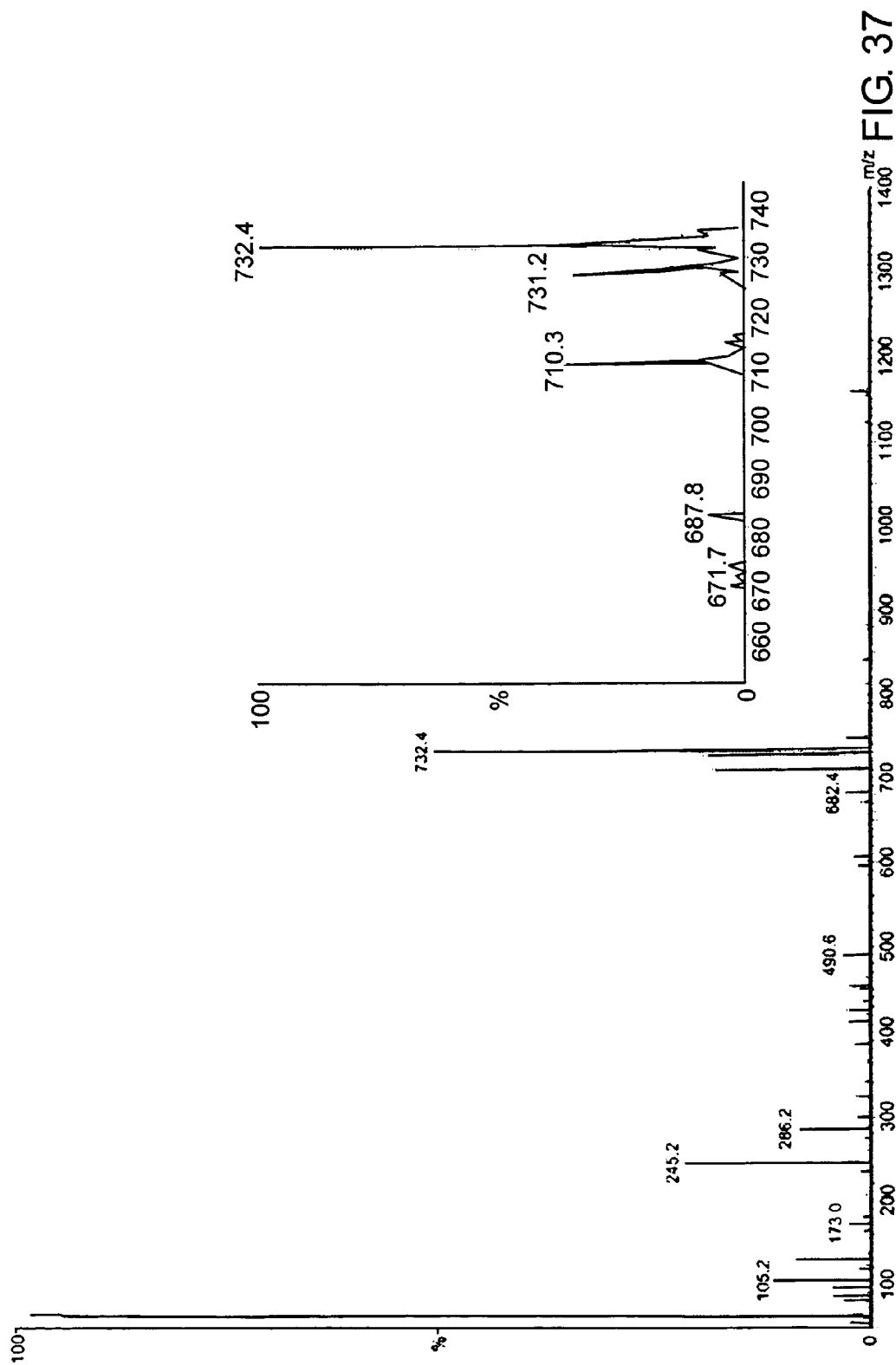
FIG. 37 depicts a positive ion electrospray mass spectrum of compound 3.14.
Figure 38:
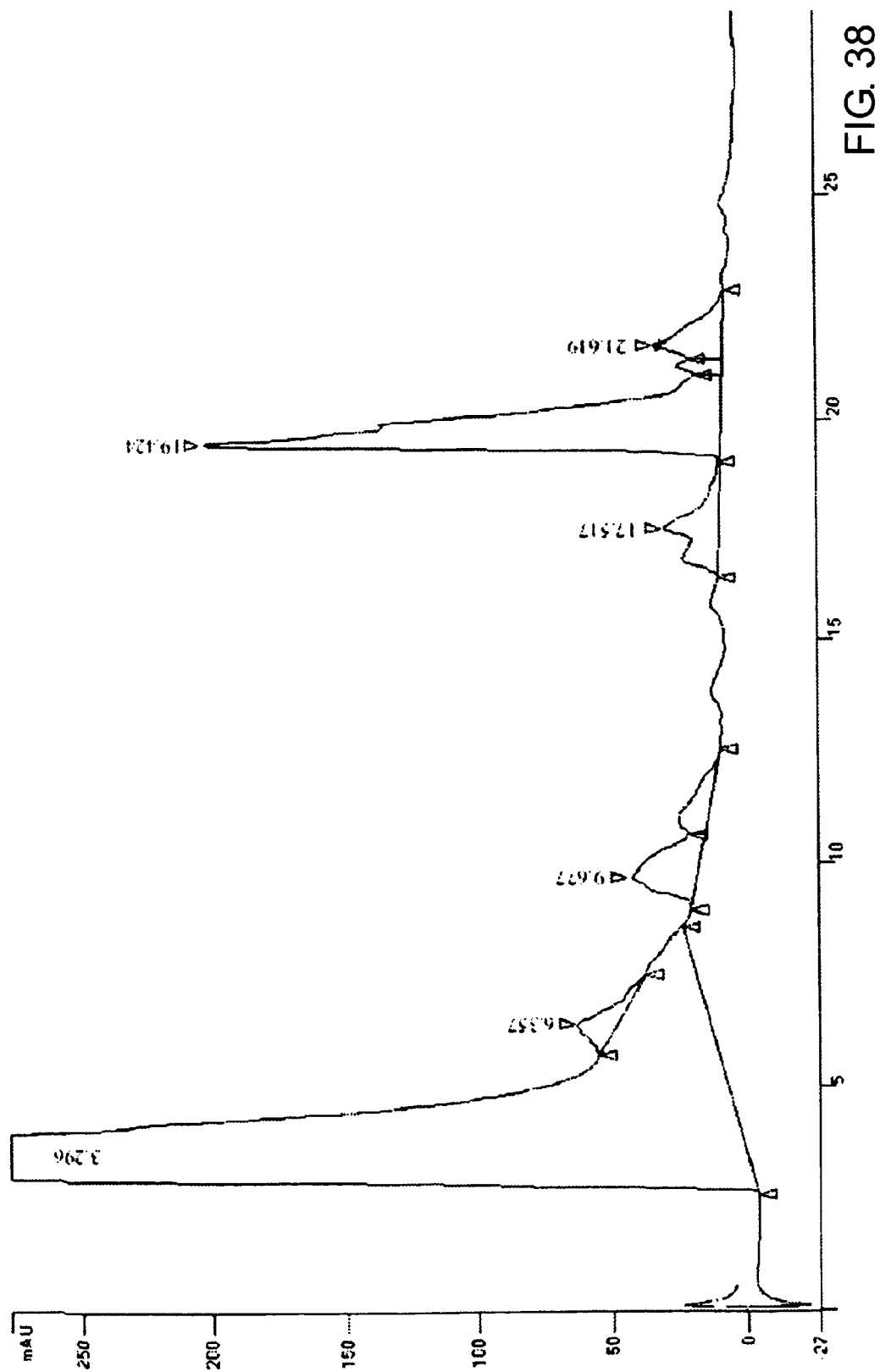
FIG. 38 depicts an HPLC chromatogram of compound 3.14.

In order to characterize the fluorous "tagged" compound (3.13) further, it was cleaved through an iodinolysis reaction (Scheme 27). A purified sample of 3.13 was reacted with excess iodine in methanol and chloroform overnight. The excess iodine was quenched with sodium metabisulfite and the solution was concentrated on the rotary evaporator. The resulting residue was diluted with acetonitrile:water (1:1) and characterised using electrospray (FIG. 37) and HPLC (FIG. 38).

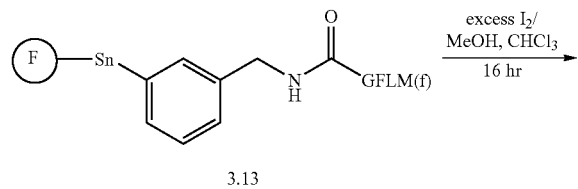

Scheme 27.
Iodinolysis of compound 3.13.

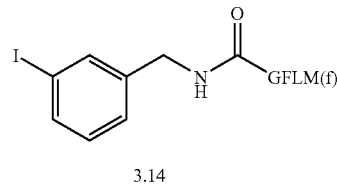

3.14

The positive ion mass spectrum of compound 3.14 reveals peaks corresponding to the desired product at m/z=710 [M+H]⁺, m/z=727 [M+NH₄]⁺, and m/z=732 [M+Na]³⁰. There is no peak corresponding to the possible impurity, 3-iodobenzylamine, at m/z=234. The HPLC chromatogram of compound 3.14 shows two sizeable peaks with retention times of 3.3 minutes and 19.4 minutes, presumably the solvent front and product respectively. The HPLC chromatogram of the GFLM(f) under the same elution conditions has a $t_R$=13.6 and 14.8 minutes, while an authentic standard of 3-iodobenzoic acid has a $t_R$=6.5 minutes. The chromatogram of 3.14 therefore seems to confirm product formation, with a longer retention time compared to GFLM(f) and no indication of the impurity at $t_R$=6.5 minutes.

Summary

The synthesis of tris(perfluorohexylethyl)tin-3-benzylamine (3.0) should facilitate the synthesis and labelling of a wider array of biomolecules. Initial results appear to confirm the successful synthesis of MIBG (3.10) and MFBG (3.11) through the corresponding fluorous "tagged" precursor (3.5). Further detailed characterisation of the precursor and products is required however, including expanding the labelling experiments to include [¹⁸F]F₂ and Na¹²⁵I.

The synthesis of fluorous "tagged" peptides through compound 3.0, has also been shown using standard coupling methodology. The differences in solubility allow for purification of the peptide coupled product (3.13) from any unreacted fluorous substrate by simple extraction. This coupling protocol should permit for a wide array of short peptides to be coupled to the fluorous support in the future. The preliminary labelling of 3.13 with iodine will have to be expanded to [¹⁸F]F₂ and Na¹²⁵I in the future.

The techniques presented herein can be used as a novel means of preparing radiopharmaceuticals. It allows for the facile synthesis of labelled compounds, without the need for extensive purification, in high radiochemical and chemical yields and in high specific activities. This is particularly important for receptor targeted radioimaging and therapy agents. This approach can also be used in pharmaceutical and radiopharmaceutical discovery research.

There are numerous advantages of the reported technology compared to traditional and resin-based labelling methods. The aforementioned techniques can be used to prepare radiolabelled compounds more efficiently, safely and more conveniently than traditional radiolabelling techniques. The approach can be adapted for a wide variety of isotopes including ⁹⁹ᵐTc, ⁹⁴ᵐTc, ¹⁸⁶Re, ¹⁰⁵Rh, ¹⁸F, ¹¹C, ¹²⁵I, ¹²³I, ¹³¹I, ⁷⁶Br, and ¹¹¹At and is easily automatable.

The fluorous-tagged compounds are readily soluble in per-fluorinated solvents. These solvents are particularly useful for carrying out labelling reactions because they are stable to reactive compounds like ¹⁸F-¹⁹F (i.e. F²). Furthermore, gases, such as ¹¹CO₂ and ¹¹CO, are highly soluble in perfluorinated solvents, which will lead to an increase in product yields compared to reactions carried out in conventional solvents. For example, it is possible to prepare carbon- 11 labelled benzophenone from a fluorous tin substrate as shown in Scheme 28. The reaction was complete in less than five minutes generating labelled benzophenone as the major product. This approach will be particularly applicable to drug development research where PET is being used to perform biodistribution studies.

Scheme 28.
Synthesis of labelled benzophenone.

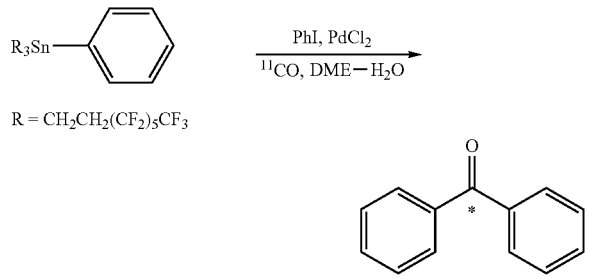

R = $CH_2CH_2(CF_2)_5CF_3$

The use of fluorous supports broadens the number of compounds that can be labelled compared to the approach using insoluble polymer supports. Conventional synthetic methods can be used to attach compounds to the fluorous supports without the need for forceful reaction conditions. Impurities can be removed (unlike polymer supported methods) using standard chemical techniques. Furthermore, fluorous-labelled substrates can be readily characterized using traditional methods, which is important when getting compounds and/or techniques approved for medical use. The reported approach can also be used to develop libraries of radiopharmaceuticals, which will facilitate the rate and efficiency with which new imaging agents are discovered.

EXEMPLICATION

The invention now being generally described, it will be more readily understood by reference to the following examples, which are included merely for purposes of illustration of certain aspects and embodiments of the present invention, and are not intended to limit the invention.

General Procedure

Analytical TLC was performed on silica gel 60-$F_{254}$ (Merck) with detection by long wavelength ultraviolet light. HPLC experiments (cold) utilized a Varian ProSTar HPLC system with a PDA detector and C-8 or C-18 reverse phase column (where mentioned). HPLC analysis of fluorine-18 labeled 3-fluorobenzoic acid employed a Waters 490E programmable multiwavelength detector and a Beckman radio-isotope detector (Model 170). Gradient or isocratic elution was performed as indicated with acetonitrile and distilled-deionized water as the mobile phase (buffered/acidified where indicated). $^1H$, $^{13}C$ and $^{19}F$ NMR spectra were recorded on the Bruker Avance AC-200 or DRX-500 spectrometers. The X-ray structure was collected using Mo Kα radiation on a Siemens rotating anode instrument fitted with a CCD detector. Electrospray mass spectrometry (ESMS) were performed on a Fisons Platform quadrupole instrument. Chemical ionisation mass spectra (CIMS) were measured at 70 eV with a source temperature of 200° C. on a VG Instruments analytical ZAB-E mass spectrometer equipped with a VG11-250 data system. IR spectra were run on a Bio-Rad F TS-40 FT FTIR spectrometer. Melting points were determined using a Fisher-John melting point apparatus. Fluorine-18 labelled $F_2$ was produced by the $^{18}O(p, n)^{18}F$ nuclear reaction using a Siemens RDS 112 proton cyclotron operating at 11 MeV by the "double shoot" method.[18]

Materials

All commercial reagents were used as supplied with the following exceptions: THF was distilled from sodium and benzophenone; toluene was distilled from calcium hydride. Enriched [$^{18}O$]$O_2$ ($^{18}O$, 95.87 at %, Eurisotope, St. Aubin, France), neon (99.999%, Air products), 1% $F_2$ in neon (Canadian Liquid Air), HPLC grade solvents (Calcdon), reagent grade FC-72® (3M corporation), and perfluorooctyliodide, phenyltintrichloride, 3-(ethoxycarbonyl)phenylzin solution, and benzotrifluoride were all purchased from Aldrich.

Tris[(2-Perfluorohexyl)ethyl]phenyltin (2.4). The procedure developed by Masahide et al. was followed.[43] To magnesium turnings 2.308 g (94.9 mmol) was added 22.501 g (47.5 mmol) of perfluorooctyliodide in 10 mL of dry ether. The reaction mixture was stirred at reflux for 25 min and then 1.95 mL (11.9 mmol) phenyltintrichloride was added in 20 mL of dry toluene. The reaction was stirred at 70° C. for 4 h and then at room temperature overnight. The reaction mixture was quenched with a 40 mL of ammonium chloride solution, and washed with three 200 mL portions of a 5% sodium thiolsulfate solution. The combined aqueous layers were additionally extracted with three 100 mL portions of diethylether. The combined organic fractions were then dried (MgSO$_4$) and concentrated under reduced pressure. Vacuum distillation removed the homocoupled impurity at 82° C. (≈0.2 mm Hg) and the residue was purified by flash chromatography on neutral alumina. Elution with hexane gave 2.4 as a colorless oil: yield 11.031 g (75%). TLC $R_f$ 0.89 (6:1 Hexanes-diethylether). $^1H$ NMR (200 MHz, CDCl$_3$): δ 1.23 (t, 6H) with Sn satellites ($^2J_{Sn,H}$=51.7 Hz), 2.24 (m, 6H), 7.33(s, 5H). $^{13}C$ NMR (50.3 MHz, CDCl$_3$): δ −1.49, 27.74 (t, $^3J_{F,C}$=23.5 Hz), 129.06, 129.65, 136.08. MS (ESMS), (IPA, 2 mM NH$_4$OAc): m/z 1297.0 [M+OAc-H]$^-$, m/z=1283.0 [M+OAc-CH$_3$]$^-$. IR (thin film): 2962, 2928, 2875, 2862, 1241, 1146, 497 cm$^{-1}$.

Bromotris[(2-Perfluorohexyl)ethyl]tin (2.3). To a solution containing 15.860 g (12.8 mmol) of 2.4 in 20 mL of diethylether at 0° C. was added slowly a solution containing 670 μL (13 mmol) of bromine in 20 mL of diethylether. The reaction solution was stirred at 0° C. for 2 h and then at room temperature overnight. The reaction solution was concentrated under diminished pressure. Vacuum distillation at 162° C. (≈0.2 mmHg) gave 2.3 as a colorless oil: yield 15.487 g (97%). $^1H$ NMR (500 MHz, CDCl$_3$): δ 1.57 (t, 6H) with Sn satellites ($^2J_{Sn,H}$=54.1 Hz), 2.46 (m, 6H). $^{13}C$ NMR (126 MHz, CDCl$_3$): δ 6.11 with Sn satellites ($^1J_{Sn,C}$=374 Hz), 27.60 (t, $^3J_{F,C}$=22.9 Hz), 108.86-120.71 (m, CF$_2$, CF$^3$). MS (ESMS,IPA 2mM NH$_4$OAc): m/z 1279.5 [M+OAc]$^-$. IR(thin film): 3472, 3417, 2949, 1442, 1146 cm$^{-1}$.

Synthesis of Tris[2-Perfluorohexylethyl]tin-4-bromobenzene (2.8). The procedure was adapted from that used by Lequan et al.[44] To 37 mg (1.52 mmol) of magnesium turnings was slowly added a solution containing 390 mg (1.66 mmol) p-dibromobenzene in 8 mL of THF. The reaction mixture was refluxed for 2 h at which time a solution containing 820 mg (0.662 mmol) of 2.3 in 6 mL of THF was added. The reaction solution was stirred overnight and then concentrated under reduced pressure. The residue was extracted with three (3 mL) portions of FC-72® from dichloromethane and water. The combined FC-720 layers were extracted again from dichloromethane and then concentrated under reduced pressure to give 2.8 as a clear colourless oil: yield 0.538 mmol (81%). $^1$H NMR (200 MHz, CDCl$_3$): δ 1.30 (t, 6H), 2.30 (m, 6H), 7.24 (d, 2H), 7.56 ppm (d, 2H). MS (ESMS): m/z 1375.0 [M+OAc]$^+$, and 1297.1 [M+OAc-Br]$^+$.

4-Bromobenzyloxazoline (2.9). The procedure was adapted from that used by Hughes, A. et al.[45] A mixture of 4.00 g (19.9 mmol) in 7.0 mL (96 mmol) thionyl chloride was refluxed for 2 h prior to concentration under reduced pressure. To the product dissolved in 10 mL of dichloromethane at 0° C. was slowly added 3.8 mL (40 mmol) of 2-amino-2-methyl-1-propanol in 10 mL of dichloromethane. The reaction solution was allowed to warm gradually overnight, filtered, and extracted from two 10 mL portions of water and dried over MgSO$_4$. The solution was concentrated under reduced pressure and to 4.850 g (17.82 mmol) of the solid was added 6 mL (80 mmol) of thionyl chloride. The reaction mixture was stirred for 45 min followed by addition of a large volume of diethylether to precipitate a white solid. The solid was filtered and extracted into diethylether from 3 N NaOH, and washed with an additional three 10 mL portions of 3 N NaOH. The combined organic layer was dried over MgSO$_4$, filtered and concentrated under reduced pressure to give 2.9 as a clear solid: yield 4.810 g (95%). $^1$H NMR (200 MHz, CDCl$_3$): δ 1.42 (s, 6H), 4.17 (s, 2H), 7.56 (d, 2H), 7.87 (d, 2H). $^{13}$C NMR (50.3 MHz, CDCl$_3$): δ 28.26, 67.58, 79.32, 125.99, 126.68, 129.80, 131.53, 161.48. Mass spectra (EI): m/z 254.

Synthesis of Tris[2-Perfluorohexylethyl]tin-benzyloxazoline (2.10). The procedure was adapted from that used by Milius et al.[46] To 215 mg (8.83 mmol) of magnesium turning was slowly added a solution containing 1.122 g (4.415 mmol) of 2.9 in 18 mL of THF. To the stirring mixture was added 1,2-dibromoethane (20 drops) and allowed to reflux for 1 h. This solution was added to a solution containg 547 mg (4.415 mmol) of 2.3 in 3 mL of FC-72® and 14 mL of benzotrifluoride. The reaction solution was stirred overnight at room temperature, and then concentrated under reduced pressure. The residue was extracted with three (3 mL) portions of F C-72® from dichloromethane and water. The combined FC-72®& layers were re-extracted with dichloromethane and concentrated under reduced pressure to give 2.10 as a clear colorless oil: yield 528 mg (90%). $^1$H NMR (200 MHz, CDCl$_3$): δ 1.32 (t, 6H), 1.40 (s, 6H), 2.30 (m, 6H), 4.14 (s, 2H), 7.44 (d, 2H, J=8.2 Hz), 7.97 (d, 2H, J=8.1 Hz). $^{13}$C NMR (50 MHz, CDCl$_3$): δ 1.25, 27.68 (t, $^3J_{F,C}$=23.4 Hz), 28.47, 67.71, 79.46, 128.36, 135.97. MS (ESMS): m/z 1394.2 [M+OAc]$^+$.

Tris[2-Perfluorohexylethyl]tin-3-ethylbenzoate (2.14). To a solution containing 8.523 g (6.879 mmol) of 2.3 in 10 mL of THF at 0° C. was slowly added 41.2 mL (20.6 mmol) of a 0.5 M 3-(ethoxycarbonyl)phenylzinc solution in THF. The solution was warmed to room temperature over 2 h and stirred overnight at r.t. The reaction solution was concentrated under diminished pressure. The residue was extracted with four 5 mL portions of FC-72® from 20 mL of methanol. The combined FC-72®, layers were concentrated under reduced pressure and dried under high vacuum to give 2.14 as a colorless oil: yield 8.903 g (98.9%). TLC R$_f$ 0.58 (6:1 hexane: diethylether). $^1$H NMR (500 MHz, CDCl$_3$): δ 1.35 (t, 6H), 1.39 (m, 3H), 2.33 (m, 6H), 4.39 (q, 2H, J=7.1 Hz), 7.49 (t, 1H, J=7.0 Hz), 7.57 (d, 1H, J=7.2 Hz), 8.05 (d, 1H), 8.07 (s, 1H). $^{13}$C N MR (50.3 M Hz, CDCl$_3$): 6-1.12, 14.20, 27.87 (t, $^3J_{F,C}$=23.3Hz), 61.17, 108.92-118.84 ppm (m, CF$_2$, CF$_3$), 128.90, 129.54, 130.79, 131.13, 131.84, 136.06, 136.97, 137.34, 140.30, 143.46, 166.67. MS(ESMS, IPA 2 mM NH$_4$OAc): m/z 1369.5 [M+OAc]$^-$, m/z=1279.4 [M-OEt]$^-$.

Tris[2-Perfluorohexylethyl]tin-3-benzoic acid (2.2). A mixture of 8.903 g (6.801 mmol) of 2.14 and 34 mL of 1N NaOH in 34 mL of methanol was refluxed for 24 h. Methanol was removed under diminished pressure and the residue was extracted with four 5 mL portions of FC-72®. The combined FC-72® layers were then extracted twice from 20 mL of dichloromethane and 10 mL of 1N HCl. The combined FC-72® layers were concentrated under diminished pressure to give 2.2 as a colourless oil: yield 8.584 g (98%). After several days 2.2 crystallised as a white solid. Dissolving approximately 100 mg of 2.2 in 1 mL of pentane followed by slow evaporation over one week gave 2.2 as colourless needles. TLC R$_f$ 0.21 (6:1 hexane-diethylether). $^1$H NMR (200 MHz, CDCl$_3$): δ 1.34 ppm (t, 6H) with Sn satellites ($^2J_{Sn,H}$=53.4 Hz), 2.31 (m, 6H), 7.51 (t, 1H, J=7.7 Hz), 7.62 (d, 1H, J=7.1 Hz), 8.11 (d, 1H), 8.12 (s, 1H). $^{13}$C NMR (126 MHz, CDCl$_3$): δ −1.53-1.06, 27.42 (t, $1J_{F,C}$=24.40 Hz), 108.49-118.51 (m, CF$_2$, CF$^3$), 128.66, 129.02, 129.73, 130.01, 130.39, 131.08, 131.34, 134.00, 135.906, 136.16, 137.53, 141.00, 141.23, 172.61, 172.04. MS (ESMS, IPA): m/z 1279.1 [M−H]$^{-1}$. IR (thin film): 3410, 2981, 2950, 1631, 1610, 1593 cm$^{-1}$.

General procedure: 3-Fluorobenzoic acid from F$_2$ reaction (2.15). To 0.191 g (0.149 mmol) of 2.2 in 1 mL of FC-72 g at −85° C. in a FEP tube was bubbled 118 μmol of 0.5% F$_2$ in Ne. The F$_2$ was steadily released into the solution over 35 min. The reaction solution along with three 3 mL portions of methanol used to rinse the vessel were concentrated in a large vial. The residue was washed with three 3 mL portions of 1:1 acetonitrile:water and eluted down a conditioned fluorous reverse phase column (1 g) to give 2.15. Yield 28.2 μmol (24%). HPLC analysis was carried out on an analytical (250 mm×4.6 mm) C$_8$ reversed-phase column. A retention time of 4.22 min. consistent with the standard was produced when flow rate=1 mL/min, eluent: 50% water (0.2% TFA): 50% acetonitrile (0.2% TFA), λ=280 nm. $^{19}$F NMR (188.16 MHz, MeOH:CHCl$_3$): δ −112.00 (d, $^3J_{F,H}$=5.65 Hz). MS [ESMS, 1:1 IPA:(ACN:H$_2$O)]: m/Z 139.1 [M−H]$^-$.

General procedure: [$^{18}$F]3-fluorobenzoic acid (2.16). To 0.124 g (97.2 μmol) of 2.2 in 1 mL FC-72® at −85° C. in a FEP tube was bubbled [$^{18}$F]F$_2$ (15-20 μmol) in Ne over 10 min. The reaction solution and two 2 mL portions of methanol used to rinse the vessel were combined and evaporated on a hot water bath under a stream of N$_2$. The residue was rinsed with three 3 mL portions of 1:1 acetonitrile: water and eluted down a fluorous reverse phase column (1 g). HPLC analysis was carried out on an analytical (250 mm×4.6 mm) C$_8$ reversed-phase column. A retention time of 4.18 min, consistent with the standard, was produced when flow rate=1 mL/min, eluent: 50% water (0.2% TFA):50% acetonitrile (0.2% TFA), λ=280 nm. The chromatogram using a γ detector produced a single peak with a retention time of 4.99 min, which is consistent with the delay times between instruments. $^{19}$F NMR (188.16 MHz, CH$_3$CN:H$_2$O): δ −110.10 (d,$^3J_{F,H}$=7.24 Hz). MS [ESMS, 1:1 IPA:(ACN:H$_2$O)]: m/z 139.0 [M−H]$^-$.

3-Iodobenzoic acid (I$_2$ reaction) (2.17). To a mixture containing 0.127 g (99.1 μmol) of 2.2 in 2 mL acetonitrile was added 1 mL (0.1 mmol) iodine in methanol. The reaction mixture was stirred for 16 hr and then quenched with a crystal of sodium metabisulfite. The reaction was diluted with 2.5 mL of distilled deionized water and the total volume added to a fluorous column (3.9 g), pre-conditioned with 1:1 acetonitrile:water. The column was eluted with 25 mL of 1:1 acetonitrile:water to give 2.17 in solution. HPLC analysis was carried out on an analytical (250 mm×4.6 mm) $C_8$ reversed-phase column. A retention time of 9.90 minutes, which is consistent with a standard of 3-iodobenzoic acid, was observed when the flow rate=1 mL/min, eluent: 80% water (0.1% HFBA):20% acetonitrile, λ=254 nm). Alternatively, varying elution conditions to a flow rate=1 mL/min: 80% water (pH=7.4): 20% acetonitrile, λ=254 nm resulted in elution of 2.17 at 2.9 minutes, also consistent with the authentic standard. MS (ESMS), m/z 246.9 [M–H]$^+$.

3-Iodobenzoic acid (Na$^{127}$I reaction) (2.18). To a solution containing 5.4 mg (4.15 μmol) of 2.2 in 200 μL of methanol was added 4 μL (0.184 nmol) NaI in 0.1 N NaOH, followed by 2 μL of peracetic acid (32% in acetic acid). The reaction was quenched at 2 h with 100 μL of a 10% sodium metabisulfite solution and diluted to 1 mL with distilled deionized water. HPLC analysis was carried out on an analytical (250 mm×4.6 mm) $C_{18}$ reversed-phase nucleosil column. HPLC analysis of a 100 μL aliquot gave a retention of 10.2 minutes, analogous to an authentic standard (flow rate=1 mL/min: 50% water (0.2% formic acid): 50% acetonitrile (0.2% formic acid), λ=254 nm).

[$^{125}$I]3-Iodobenzoic acid (Na$^{125}$I reaction) (2.19—no impurities). To a solution containing 1.4 mg (1.07 μmol) of 2.2 in 200 μL of methanol was added 5 μL (32 μCi) Na$^{125}$I in 0.01 N NaOH, followed by 2 μL of peracetic acid (32% in acetic acid). The reaction was stirred for 47 min followed by quenching with 20 μL of a 10% solution of sodium metabisulfite and dilution with 300 μL of distilled-deionized water. HPLC analysis was carried out on an analytical (250 mm×4.6 mm) $C_{18}$ reversed-phase nucleosil column. HPLC analysis of a 20 μL aliquot gave a retention time of 16.91 min on the chromatogram using the γ detector. There was no visible UV absorbance other than the solvent front. The retention time was consistent with an authentic standard of 3-iodobenzoic acid (flow rate=0.5 mL/min, 50% water (0.2% formic acid):50% acetonitrile (0.2% formic acid), λ=254 nm).

The solution was diluted with 1 mL of distilled deionized water and eluted through a Waters $C_{18}$ Sep-Pak previously conditioned with water. The column was eluted with an additional 1.5 mL of distilled deionized water and the combined fractions showed an activity of 3 μCi. The column was then washed with 2 mL of HPLC grade acetonitrile and released 23 μCi of activity. An additional washing of the column with 1 mL of acetonitrile resulted in only 1 μCi of activity being released. The remaining activity was found in the Sep-Pak (4 μCi) and original reaction vessel (1 μCi). HPLC analysis was carried out on an analytical (250 mm×4.6 mm) $C_{18}$ reversed-phase nucleosil column. HPLC analysis of a 20 μL aliquot gave a retention time of 16.586 min on the γ detector and no visible UV peak. The retention time was consistent with an authentic standard of 3-iodobenzoic acid (flow rate=0.5 mL/min: 50% water (0.2% formic acid): 50% acetonitrile (0.2% formic acid), λ=254 nm).

Modification of the elution conditions to a flow rate=1 mL/min: 100% acetonitrile, and λ=254 nm resulted in a peak at 4.458 min on the γ detector and two peaks at 6.379 min and 6.720 m in on the UV chromatogram. These two peaks have a similar retention time as 2.2, 6.613 min, under similar elution conditions.

The acetonitrile solution (approx. 2 mL) was diluted with 2 mL of distilled deionized water and passed down a Fluorous technologies® Sep-Pak. A total of 9 μCi was released in the eluting volume. Washing the column with an additional 4 mL of (1:1) acetonitrile:water yielded a total 19 μCi when combined with the previous fraction. No additional activity was found in either the Fluorous Sep-Pak or previous vial. HPLC analysis was carried out on an analytical (250 mm×4.6 mm) $C_{18}$ reversed-phase nucleosil column. HPLC analysis of a 20 μL aliquot gave a small peak at 6.532 min UV chromatogram (flow rate=1.0 mL/min: 100% acetonitrile, and λ=254 nm).

Tris[2-Perfluorohexylethyl]tin-3-benzamide (2.21). To a reaction solution containing 294 mg (226 μmol) of 2.2 in 2.5 mL of DMF was added 0.130 g (344 μmol) of HBTU, followed by 90 μL (517 μmol) diisopropylethylamine (DIPEA). The reaction solution was stirred for 5 min prior to addition of 251 μL (2.29 mmol) of N,N-dimethylethylenediamine and 400 μL (2.30 mmol) of DIPEA. The reaction solution was then stirred for 16 h. The solution was diluted with 20 mL of water and extracted into 50 mL of dichloromethane and 10 mL of FC-720. The FC-72® layer was re-extracted with three additional 10 mL portions of dichloromethane. The combined organic layers were re-extracted with 20 mL of water prior to concentration under reduced pressure to give 2.21 as a dark orange oil: yield 227 mg (74%). TLC $R_f$ 0.00 (6:1 hexane-diethylether). $^1$H NMR (CDCl$_3$, 200 MHz): δ 1.31 (t, 6H) with Sn satellites ($^2J_{Sn,H}$=54.8 Hz), 2.31 (6H), 2.33 (m, 6H), 2.59 (dt, 2H), 3.55 (q, 2H), 7.14-7.90 (m, 4H). $^{13}$C NMR (CDCl$_3$, 50.3 MHz): 6-1.43, 27.55 (t, $^3J_{F,C}$=23.4 Hz), 37.11, 44.87, 57.75, 104.80-120.03 (m, CF$_2$, CF$_3$), 127.04, 127.71, 128.66, 134.70, 134.82, 136.01, 137.53, 138.69, 167.16, 167.41. IR (thin film): 3338, 2950, 2831, 1650 cm$^{-1}$. MS (ESMS), m/z 1353.0 [M+H]$^+$.

3-Iodobenzamide (I$_2$ reaction of 2.21) (2.20). To a solution containing 3.2 mg (2.37 μmol) of 2.21 in 200 μL methanol was added 30 μL (3.0 μmol) of 0.1 M iodine. The reaction solution was stirred for 1 h prior to quenching with 100 μL of a 10% solution of sodium metabisulfite. The solution was diluted with 700 μL of distilled-deionized water and analysed on a nucleosil $C_{18}$ reversed-phase column. A retention time of 16.6 min and 18.9 min was observed (flow rate=2 mL/min, 80% H$_2$O (0.01 M NaH$_2$PO$_4$):20% CH$_3$CN, and %=254 μm). MS (ESMS), m/z 319 [M+H]$^+$.

3-Fluorobenzamide (F$_2$ reaction of 2.21). To 180 mg (133 μmol) of 2.21 in 1 mL of FC-728 at –90° C. in a FEP tube was bubbled 131 μmol of 0.5% F$_2$ in Ne. The F$_2$ was steadily released into the solution over 25 min. The reaction solution along with two 3 mL portions of FC-72® used to rinse the vessel were concentrated in a large vial. The residue was washed with three 3 mL portions of acetonitrile and eluted down a conditioned fluorous reversed-phase column (1 g). MS (ESMS), m/z 211.1 [M+H]$^+$, 193.1 [M-F+H]$^+$.

Tris[2-Perfluorohexylethyl]tin-3-benzylamine (3.0). A mixture containing 3.990 g (2.84 mmol) of 3.3 in 125 mL of 9:1 methanol: water with sufficient 0.5 N HCl to give a pH=3.07 was stirred overnight. To the reaction mixture was added 20 mL 1 N NaOH solution, which was followed by removal of methanol under reduced pressure. The reaction mixture was subsequently extracted with four (3 mL) portions of FC-726. The FC-72® layers were combined and re-extracted from 5 mL of dichloromethane. The solvent was concentrated under reduced pressure to give 3.0 as a light yellow oil: yield 3.482 g (97%). TLC $R_f$ 0.22 (6:1 hexane-diethylether). $^1$H NMR (200 MHz, CDCl$_3$): δ 1.31 (t, 6H) with Sn satellites ($^2J_{Sn,H}$=54.2 Hz), 2.31 (m, 6H), 3.88 (s, 2H), 7.22-7.46 (m, 4H). $^{13}$C NMR (126 MHz, CDCl$_3$): δ –1.37 with Sn satellites ($^1J_{Sn,C}$=347 Hz), 27.94 (t, $^1J_{F,C}$=23.4 Hz), 46.62, 106.17-121.17 (m, CF$_2$, CF$_3$), 128.63, 129.19, 129.72, 134.60, 134.90, 135.56, 135.66, 136.96, 138.42, 140.08, 143.89, 162.09. IR (thin film), 3386, 2944, 2870, 1647, 1250 cm$^{-1}$. MS (ESMS, IPA): m/z 1268.5 [M+H]$^+$.

1-(3-Bromobenzyl)-2,2,5,5-tetramethyl-1,2,5-azadisilolidine (3.1). The procedure developed by Magnus et al. was followed.[5] To a solution containing 2.228 g (11.98 mmol) of 3-bromobenzylamine in 10 mL of dichloromethane was added 3.4 mL (24 mmol) of triethylamine. The solution was stirred for 30 min and then treated with a solution containing 2.579 g (11.98 mmol) of 1,1,4,4-tetramethyl-1,4-dichlorosilethylene in 5 mL of dichloromethane. The reaction mixture was stirred for 3 h and then poured into 100 mL of saturated sodium dihydrogen phosphate. The reaction mixture was extracted with three 50 mL portions of dichloromethane, then dried (MgSO$_4$), and concentrated under reduced pressure. The residue was distilled at 160° C. to give 3.1 as a clear colourless oil: yield 2.510 g (64%). $^1$H NMR (200 MHz, acetone-d$_6$): δ 0.00 (s, 12H), 0.78 (s, 4H), 4.06 (s, 2H), 7.20-7.48 (m, 4H). $^{13}$C NMR (50.3 MHz, Acetone-d6): δ −0.26, 8.01, 45.59, 122.15, 126.10, 129.35, 129.53, 130.69, 146.01. IR (thin film): 3388, 2953, 1666, 1251, and 1132 cm$^{-1}$. MS (CI): m/z=312.

Tris[2-Perfluorohexylethyl]tin-(3-bromobenzyl)-2,2,5,5-tetramethyl-1,2,5-azadisilolidine (3.3). To a solution containing 4.301 g (13.1 mmol) of 3.1 in 30 mL of THF at −78° C. was slowely added 5.24 mL (13.1 mmol) of 2.5 M n-BuLi. The reaction solution was stirred for 40 minutes, followed by addition of a solution containing 4.3662 g (3.521 mmol) of 2.3 in 20 mL of THF. The reaction solution was stirred at −78° C. for 2 h and then diluted with 5 mL of FC-72® and 30 mL of methanol. The reaction solution was extraction with three 4 mL portions of FC-72®. The combined fluorous layers were concentrated under reduced pressure to give 3.3 as a light yellow oil: yield 4.732 g (96%). $^1$H NMR (200 MHz, CDCl$_3$): δ 0.01-0.21 (s,12H), 0.80 (s, 4H), 1.34 (t, 6H, $^2J_{Sn,CH}$=27.5 Hz), 2.35 (m, 6H), 3.96-4.06 (s, 2H), 7.28-7.39 (m, 4H). IR (thin film), 3354, 2955, 2849, 1256, and 442 cm$^{-1}$. MS (ESMS, IPA): m/z 1268.3 [M-(2,2,5,5-tetramethyl-1,2,5-azadisilolidine+H]$^+$.

3-Iodobenzylamine (12 reaction with 3.0) (3.4). To a mixture of 0.164 g (129 μmol) of 3.0 in 2 mL of acetonitrile was added 1.5 mL of 0.1 M iodine in methanol. The reaction mixture was stirred for 16 h prior to quenching with a crystal of sodium thiosulfate and dilution with 3 mL of deionized distilled water. The reaction mixture was purified by flash chromatography using silicycle® fluorous silica (3.9 g). Elution with 1:1 acetonitrile-water and collection of four 5 mL fractions gave 3.4 in solution. HPLC analysis was carried out on an analytical (250 mm×4.6 mm) C$_8$ reversed-phase column. A retention time of 6.461 min, consistent with a standard, was generated when the column was eluted with 80% H$_2$O (pH>7.4): 20% CH$_3$CN at a flow rate of 1.5 mL/min and λ=254 nm. MS (ESMS), m/z 233.9 [M+H]$^+$.

Tris[2-Perfluorohexylethyl]tin-3-benzylguanidine using formamidine sulfinic acid (3.5—Approach B). To a mixture containing 1.964 g (1.549 mmol) of 3.0 in methanol (15 mL) was added 0.184 g (1.704 mmol) of 3.7. The reaction mixture was stirred for 16 h and then methanol was decanted from the resulting viscous oil. The oil was washed with three (10 mL) portions of hot chloroform and then two portions of hot water. The residue was extracted into 5 mL of FC-72® from dichloromethane and residual water. The solvent was concentrated to give 3.5 as a clear orange oil: yield 1.654 g (82%). Mass spectrum (ESMS), m/z 1310.2 [M+H]$^+$, 1293.0 [M+H-15]$^+$, and 1325.0 [M+H$^+$15]$^+$.

Tris[2-Perfluorohexylethyl]tin-3-benzlguanidine using aminoimino-methanesulfinic acid (3.5—Approach C). To a mixture containing 518 mg (409 μmol) of 3.0 in 1 mL of methanol was added 55.8 mg (450 μmol) of aminoiminomethanesulfonic acid. The reaction mixture was then refluxed for 16 h. The reaction mixture was extracted into 5 mL of FC-72® from 10 mL of methanol. The solvent was concentrated under reduced pressure to give 3.5 as an orange oil: yield 468 mg (88%). TLC R$_f$ 0.25 (6:1 hexane-diethyl-ether). IR (thin film), 3349, 3197, 2946, 1647, 1449, 1239, 446 cm$^{-1}$. Mass spectrum (ESMS), m/z 1309.9 [M+H]$^+$.

Aminoiminomethanesulfonic acid (3.7). The procedure developed by Mosher et al. was followed.[12] To a mixture containing 0.633 g (5.85 mmol) of 3.6 in 3.0 mL of glacial acetic acid at 0° C. was slowly added 1.56 mL of 32% peracetic acid. The reaction mixture was then stirred for 16 h at room temperature. The precipitate was filtered and washed with five 5 mL portions of absolute ethanol and dried to give 3.7 as a white crystalline solid: yield 596 mg (82%).mp 125-126° C.

3-Iodobenzylguanidine (3.9). To a solution containing 168 mg (721 μmol) of 3.8 in 1 mL of methanol was added 90.1 mg (726 μmol) of 3.7. The reaction solution was refluxed for 16 h and then concentrated under reduced pressure to give 3.9 as a viscous yellow gum: yield 258 mg. HPLC analysis was preformed using a nucleosil C$_{18}$ reversed-phase column. A retention time of 24.54 min was generated when the column was eluted with 80% H$_2$O (0.01 M NaH$_2$PO$_4$): 20% CH$_3$CN at a flow rate of 2.0 mL/min and λ=231 nm. $^1$H NMR (MeOH, 200 MHz): δ 4.22 (s, 2H), 6.99 (t, 1H), 7.22 (d, 1H), 7.49 (d, 1H), 7.56 (s, 1H). $^{13}$C NMR (MeOH, 50.3 MHz): δ 48.95, 99.31, 131.64, 135.72, 141.05, 141.93, 144.30, 162.65. IR (thin film): 3407, 3192, 1653, 1115 cm$^{-1}$. MS (ESMS, methanol), m/z 276.1 [M+H]$^+$.

3-Iodobenzylguanidine (NaI reaction with 3.5) (3.10). To a reaction mixture containing 5.1 mg (3.90 μmol) of 3.5 in 200 μL of methanol was added 10 μL (0.460 nmol) of NaI followed by 2 μL of solution of peracetic acid (35% in acetic acid). The reaction mixture was stirred for 2 h and then quenched with 100 μL of sodium metabisulfite (10%) solution, prior to dilution to 1 mL with distilled deionized water. HPLC analysis was performed with a nucleosil C$_{18}$ analytical column. A retention time of 24.89 min was observed (80% H$_2$O (0.01 M NaH$_2$PO$_4$): 20% CH$_3$CN at a flow rate of 2.0 mL/min and λ=231 nm). MS (ESMS), m/z 276.0 [M+H]$^+$.

Fluorination of 3.5 using [F$_2$] (3.11). To 0.334 g (0.255 mmol) of 3.5 in 1 mL of FC-72® at −95° C. in a FEP tube was bubbled 172 μmol of 0.63% F$_2$ in Ne. The F$_2$ was steadily released into the solution over 35 min. The reaction solution along with two 3 mL portions of FC-72® used to rinse the vessel were concentrated in a large vial. The residue was washed with three 3 mL portions of 1:1 acetonitrile:water and eluted down a conditioned fluorous reversed-phase column (1 g) to give 3.11 in solution. HPLC analysis was carried out on a nucleosil analytical (250 mm×4.6 mm) C$_{18}$ reversed-phase column. A retention time of 34.98 min was observed (80% H$_2$O (0.01 M NaH$_2$PO$_4$): 20% CH$_3$CN at a flow rate of 2.0 mL/min and λ=231 nm). $^{19}$F NMR (ACN:H$_2$O, 470.493 Hz): 6-110.3 ($^3J_{F,H}$=8.7 Hz), −109.5 ($^3J_{F,H}$=9.2 Hz). MS (ESMS), m/z 168.0 [M+H]$^+$.

Tris[2-Perfluorohexylethyl]-3-benzylamine-GFLM(f) (3.13). To a reaction solution containing 137 mg (108 μmol) of 3.0 and 84 mg (170 μmol) of GFLM(f) in 5 mL of DMF was added 71 mg (187 μmol) HBTU. To the reaction solution was added 97 μL of DIPEA and allowed to stir at for 16 h. The solution was diluted with 20 mL of water and extracted with 5 mL of FC-72®. The emulsion partitioning FC-72® and the aqueous layer was extracted and washed with three 3 mL portions of FC-72®. The residual solvent was removed under reduced pressure to give 3.12 as a milky white oil: yield 63 mg (33%). MS (ESMS), m/z 1744 [M+H]$^+$, 1761 [M+NH$_4$]$^+$, 1766 [M+Na]$^+$.

3-Iodobenzyl-GFLM(f) (I$_2$ reaction with 3.13) (3.14). To a reaction mixture containing 50 mg (28.7 μmol) of 3.13 in 3 mL of chloroform was added 1.5 mL (150 μmol). The reaction mixture was stirred for 16 h prior to quenching with a sodium thiosulfate solution. The chloroform was removed under reduced pressure, and the mixture was diluted with 10 mL of 5:1 acetonitrile:water. The reaction solution was washed with three 1.5 mL portions of FC-72® and the aqueous layer was isolated and assessed for the presence of 3.14. HPLC analysis was carried out on a nucleosil C$_{18}$ reversed-phase analytical column (250 mm×4.6 mm). A retention time of 19.4 min was observed (80% H$_2$O (0.01 M NaH$_2$PO$_4$): 20% CH$_3$CN at a flow rate of 2.0 mL/min and λ=254 nm). MS (ESMS), m/z 319 [M+H]$^+$.

Synthesis and purification of N-hydroxysuccinimidyl 3-iodobenzoate. The N-hydroxysuccinimidyl tri(fluoroalkyl)stannylbenzoate, which was prepared following the method shown below in the Scheme, was reacted with $^{125}$I$^-$ in the presence of chloramine-T following the method of L indegren et al. L indegren, S.; Skamemark, G.; Jacobsson, L.; Karlsson, B. *Nuc. Med. Biol.* 1998, 25, 659.

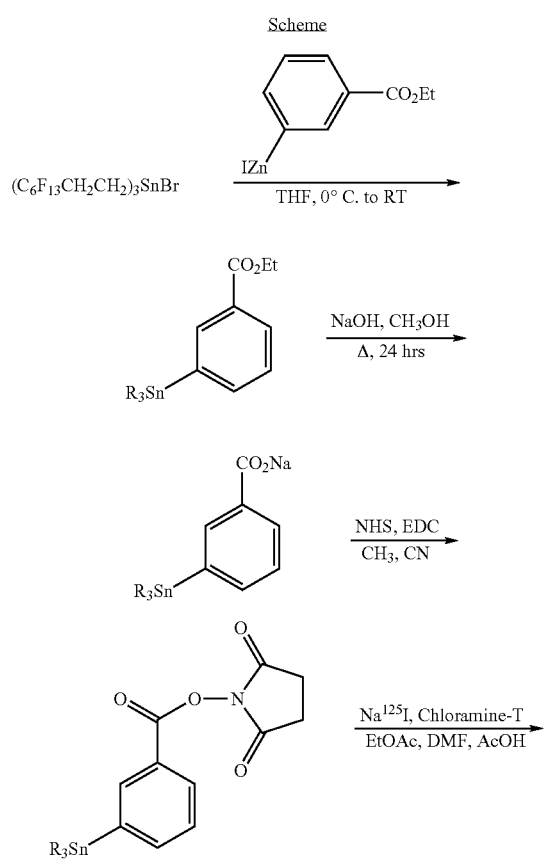

Scheme

-continued

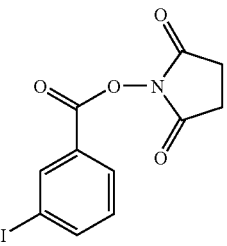

Figure 39:
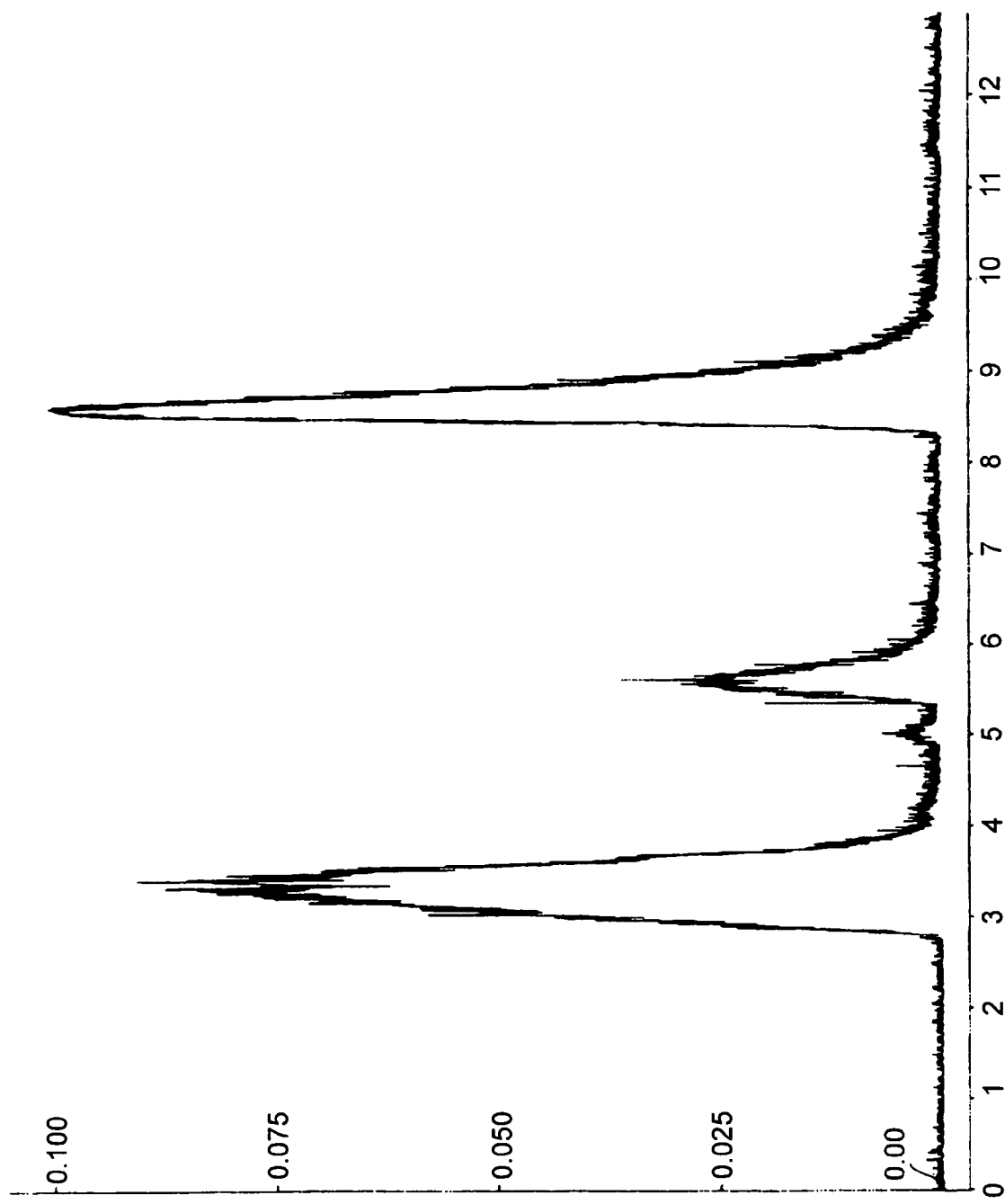
FIG. 39 depicts an HPLC chromatogram of N-hydroxysuccinimidyl 3-iodobenzoate purified using an extraction protocol.
Figure 40:
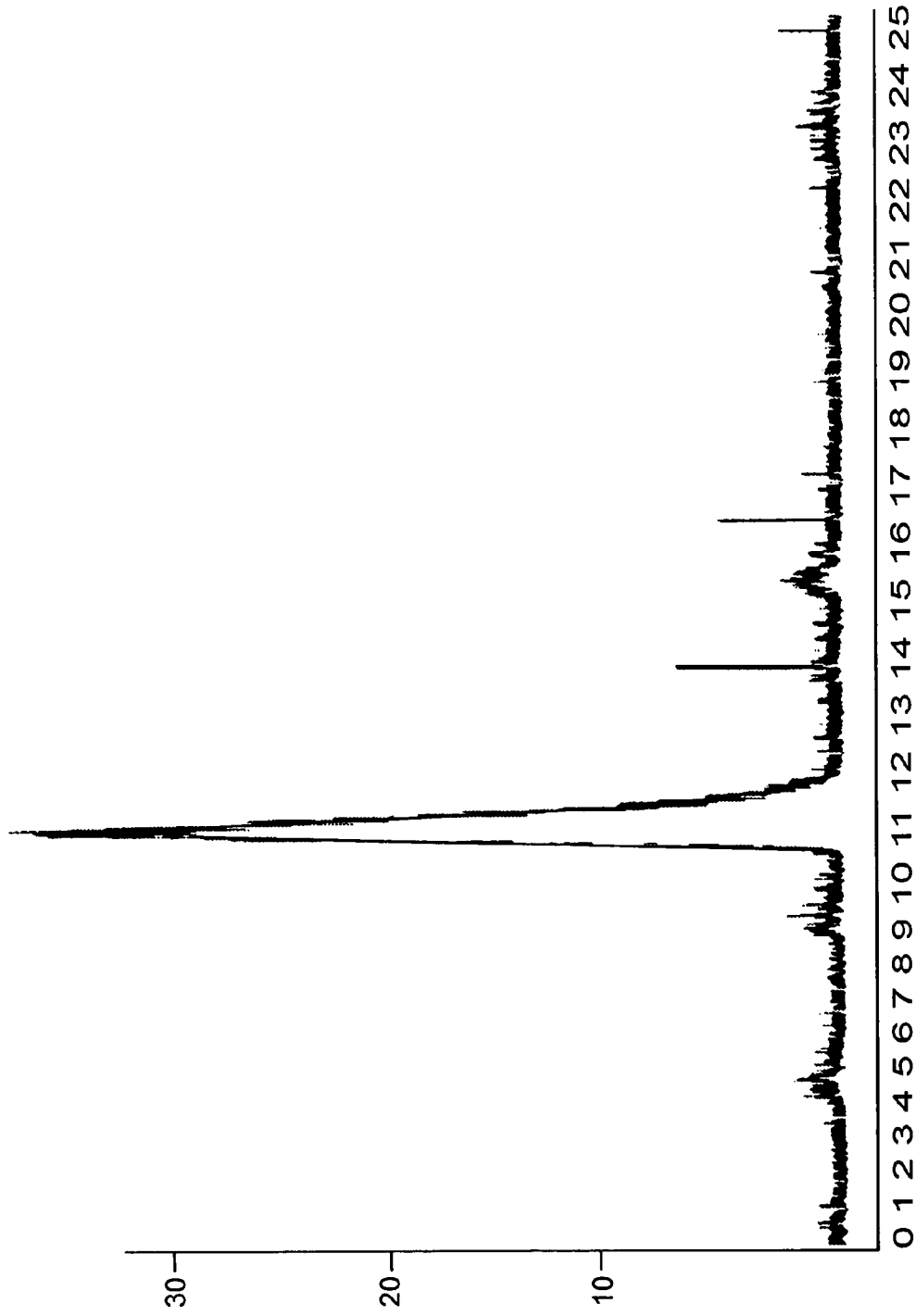
FIG. 40 depicts an HPLC chromatogram of N-hydroxysuccinimidyl 3-iodobenzoate purified using a fluorous sep-pak protocol of the present invention.

The reaction was stopped prematurely to compare the ability of two separate purification methods to remove impurities. The initial method involved extraction with perflourinated hexanes (FC-72) following dilution of the reaction mixture with water. The HPLC trace of the aqueous layer (FIG. 39) showed the desired product, its hydrolysis product m-[$^{125}$I]iodobenzoic acid and some unreated $^{125}$I$^-$. The second purification method, which is more convenient and more easily automated than extraction, involved passing the reaction mixture down a commercially available fluorous Sep-Pak. The purification protocol involved washing with 100% water to remove unreacted iodide, which was immediately followed with 80/20 methanol-water which caused the desired product to elute. The HPLC of the methanol-water eluent (FIG. 40) showed one major peak, which corresponds to the desired product. The fluorous labeling method has a number of advantages over traditional labeling methods, including ease of automation, sterilization and the fact that all of the precursors can be purified and characterized by traditional methods.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES CITED

[1] Blok, D.; Feitsma, R. I. J.; Vermeij, P.; Pauwels, E. J. K. *Eur J Nucl Med.* 1999, 26, 1511.
[2] Krenning, E. P.; Bakker, W. H.; Breeman, W. A. *Lancet.* 1989, 1, 242.
[3] Hunter, R. M.; Greenwood, F. C. *Nature.* 1962, 194, 495.
[4] Fracker, P. J.; Speck, J. C. *Biochem. Biophys. Res. Commun.* 1987, 80, 849.
[5] Bolton, A. M.; Hunter, R. M. *Biochem. J.* 1973, 133, 529.
[6] Okarvi, S. M. *Eur. J. Nucl. Med.* 2001, 28, 929.
[7] Okarvi, S. M. *Eur. J. Nucl. Med.* 2001, 28, 929.
[8] Hoshino, M.; Degenkolb, P.; Curran, D. P. *J. Org. Chem.* 1997, 62, 8341.
[9] Studer, A; Jeger, P.; Wipf, P.; Curran, D. P. *J. Org. Chem.* 1997, 62, 2917.
[10] Lequan, M.; Meganem, F. *J. Organometallic Chem.* 1975, 94, C1-C2.
[11] Milius, R. A.; McLaughlin, W. H.; Lambrecht, R. M.; Wolk, A. P.; Carroll, J. J.; Adelstein, S. J.; Bloomer, W. D. *Appl. Radiat. Isot.* 1986, 37, 799.

[12]Hughes, A. B.; Melvyn, V. *J. Chem. Soc. Perkin. Trans.* 1989, 1, 1787.

[13]Ishibashi, K.; Nakajima, K.; Nishi, T. Heterocycles. 1998, 48, 2669.

[14]Xizhen, Z.; Blough, B. E.; Carroll, F. I. *Tetrahedron Letters.* 2000, 41, 9222.

[15]Gutowsky, H. S.; Hoffman, C. J. *J. Chem. Phys.* 1951, 19, 1259.

[16]Taft, R. W. *J. Phys. Chem.* 1960, 64, 1805.

[17]Chirakal, R.; Adams, R. M.; Fimau, G.; Schrobilgen, G. J.; Coates, G.; Garnette, E. S. *Nucl. Med. Biol.* 1995, 22, 111.

[18]DeVries, E. F. J.; Luurtsema, G.; Brussermann, M.; Elsinga, P. H.; Vallburg, W. *Appl. Radiat. Isot.* 1999, 51, 389.

[19]Namavari, M.; Bishop, A.; Satyamurthy, N.; Bida, G.; Barrio, J. R. *Appl. Radiat. Isot.* 1992, 43, 989.

[20]Lemaire, C.; Guillaume, M.; Cantineau, R.; Plenevaux, A.; Christiaens, L. *Appl. Radiat. Isot.* 1991, 42, 629.

[21]Chirakal, R.; Finau, G.; Garnett, E. S. *J. Nucl. Med.* 1986, 27, 417.

[22]Katsifis, A; Mattner, F.; Zhang, Z., et al. *J. Labelled Compds Radiopharm.* 2000, 43, 385.

[23]Hunter, D. H.; Zhu, X. *J. Labelled Cpd. Radiopharm.* 1999, 42, 653.

[24]Auzeloux, P.; Papon, J.; Azim, E. M.; Borel, M.; Pasqualini, R.; Veyre, A.; Madelmont, J-C. *J. Med. Chem.* 2000, 43, 190.

[25]Laulumaa, V.; Kuikka, J. T.; Soininen, H.; Bergstrom, K.; Lansimies, E.; Riekkinen, P. *Arch. Neurol.* 1993, 50, 509.

26Moreau, M. F.; Labarre, P.; Foucaud, A.; Seguin, H.; Bayle, M.; Papon, J.; Madelmont, J. C. *J. Labelled Cpd. Radiopharm.* 1998, XLI, 965.

[27]Li, W-R.; Chou, H-H. *Synthesis.* 2000, 1, 84.

[28]Kuhnast, B; Dolle, F; Terrazzino, S.; Rousseau, B.; Loc'h, C.; Vaufrey, F.; Hirmen, F.; Doignon, I.; Pillon, F.; David, C; Crouzel, C.; Tavitian, B. *Bioconjugate Chem.* 2000, 11, 627.

[29]Wafelman, A. R.; Konings, M. C. P; Hoefniagel, C. A.; Maes, R. A. A.; Beijnen, J. H. *Appl. Radiat. Isot.* 1994, 10, 997.

[30]Vaidyanathan, G.; Zalutxky, M. R.; DeGrado, T. R. *Bioconjugate Chem.* 1998, 9, 758.

[31]Hunter, D. H.; Zhu, Xizhen. *J. Labelled Cpd. Radiopharm.* 1999, 42, 653.

[32]Djuric, S.; Venit, J.; Magnus, P. *Tetrahedron Letters.* 1981, 22, 1787.

[33] Amartey, J. K.; Al-Jammaz, I.; Lambrecht, R. M. *Appl. Radiat. Isot.* 2001, 54, 711.

[34]Vaidyanathan, G.; Affleck, D. J.; Zalutsky, M. R. *Bioconjugate Chem.* 1996, 7, 102.

[35]Vaidyanathan, G.; Zalutsky, M. R. *Appl. Radiat. Isot.* 1993, 3, 621.

[36]Grag, P. K.; Garg, S.; Zalutsky, M. R. *Nucl. Med. Biol.* 1994, 21, 97.

[37]Wieland, D. M.; Wu, J-I.; Brown, L. E.; Mangner, T. J.; Swanson, D. P.; Beirwaltes, W. H. *J. Nucl. Med.* 1980, 21, 349.

[38]Jursic, B. S.; Neumann, D.; McPherson, A. *Synthesis.* 2000, 12, 1656.

[39]Kim, K.; Lin, Y-T.; Mosher, H. S. *Tetrahedron Lett.* 1988, 29, 3183.

[40]Wafelman, A. R.; Konnings, M. C. P.; Hoefniagel, C. A.; Maes, R. A. A.; Beijnen, J. H. *Appl. Radiat. Isot.* 1994, 45, 997.

[41]Taft, R. W.; Price; E.; Fox, I. R.; Lewis, I. C.; Anderson, K. K.; Davis, G. T. *J. Am. Chem. Soc.* 1963, 85, 3146.

[42]Fischman, A. J.; Pike, M. C.; Kroon, D. *J Nucl Med.* 1991, 32, 483.

[43]Masahide, H.; Degenkolb, P.; Curran, D. P. *J. Org. Chem.* 1997, 62, 8342.

[44]Lequan, M.; Meganem, F. *J. Organometallic Chem.* 1975, 94, C1-C2.

[45]Hughes, A. B., Sargent, Melvyn, V. *J. Chem. Soc. Perkin. Trans.* 1989, I, 1787.

[46]Milius, R. A.; McLughlin, W. H.; Lambrecht, R. M.; Wolk, A. P.; Carroll, J. J.; Adelstein, S. J.; Bloomer, W. D. *Appl. Radiat. Isot.* 1986, 37, 799.

What is claimed is:

1. A method of purifying radiolabelled compounds, comprising:
   a) loading onto a fluorous silica a radiolabelled compound precursor comprising a fluoroalkyl tin moiety;
   b) reacting the radiolabelled compound precursor with a radiolabel delivering compound to give a radiolabelled compound, wherein the fluoroalkyl tin moiety is replaced by a radiolabel; and
   c) eluting the radiolabelled compound from the fluorous silica.

2. The method of claim 1, wherein the radiolabelled compound comprises an aryl moiety.

3. The method of claim 1, wherein the radiolabelled compound comprises an aryl acid.

4. The method of claim 1, wherein the radiolabelled compound is a benzoic acid.

5. The method of claim 1, wherein the radiolabelled compound is a benzamide.

6. The method of claim 5, wherein the benzamide is an N-(2-diethylaminoethyl)benzamide.

7. The method of claim 1, wherein the radiolabelled compound is a benzylamine.

8. The method of claim 1, wherein the radiolabelled compound is a benzylguanidine.

9. The method of claim 1, wherein the radiolabelled compound is a benzylamin-GFLM(f).

10. The method of claim 1, wherein the fluoroalkyl tin moiety is tris(perfluorohexylethyl)tin.

11. The method of claim 1, wherein the radiolabel is selected from the group consisting of $^{99m}$Tc, $^{94m}$Tc, $^{186}$Re, $^{105}$Rh, $^{18}$F, $^{11}$C, $^{125}$I, $^{123}$I, $^{131}$I, $^{76}$Br, and $^{111}$At.

12. The method of claim 1, wherein the radiolabel is selected from the group consisting of $^{18}$F, $^{125}$I, $^{123}$I, and $^{131}$I.

13. The method of claim 1, wherein the radiolabelled compound is a benzoic acid, the fluoroalkyl tin moiety is tris(perfluorohexylethyl)tin, and the radiolabel is $^{18}$F.

14. The method of claim 1, wherein the radiolabelled compound is a benzoic acid, the fluoroalkyl tin moiety is tris(perfluorohexylethyl)tin, and the radiolabel is $^{125}$I.

15. The method of claim 1, wherein the radiolabelled compound is an N-(2-diethylaminoethyl) benzamide, the fluoroalkyl tin moiety is a tris(perfluorohexylethyl)tin, and the radiolabel is $^{123}$I.

16. The method of claim 1, wherein the radiolabelled compound is benzylaamine, the fluoroalkyl tin moiety is tris(perfluorohexylethyl)tin, and the radiolabel is selected from the group consisting of $^{123}$I and $^{131}$I.

17. The method of claim 1, wherein the radiolabelled compound is a benzylguanidine, th fluoroalkyl tin moiety is is(perfluorohexylethyl)tin, and the radiolabel is selected from the group consisting of $^{123}$I and $^{131}$I.

18. The method of claim 1, wherein the radiolabelled compound is a benzylamine-GFLM(f), the fluoroalkyl tin moiety is tris(perfluorohexylethyl)tin, and the radiolabel is selected from the group consisting of $^{123}$I and $^{131}$I.

* * * * *